US012595302B2

(12) United States Patent
Tan et al.

(10) Patent No.: US 12,595,302 B2
(45) Date of Patent: Apr. 7, 2026

(54) CLDN18.2 BINDING MOLECULE

(71) Applicant: SANYOU BIOPHARMACEUTICALS CO., LTD., Shanghai (CN)

(72) Inventors: Yongcong Tan, Shanghai (CN); Guojun Lang, Shanghai (CN); Chao Kong, Shanghai (CN); Chanjuan Liu, Shanghai (CN); Min Deng, Shanghai (CN); Qi Wu, Shanghai (CN); Jing Zhang, Shanghai (CN); Wenhai Zhang, Shanghai (CN); Baoguo Fan, Shanghai (CN)

(73) Assignee: SANYOU BIOPHARMACEUTICALS CO., LTD., Shanghai (CN)

( * ) Notice: Subject to any disclaimer, the term of this patent is extended or adjusted under 35 U.S.C. 154(b) by 1143 days.

(21) Appl. No.: 17/613,440

(22) PCT Filed: May 21, 2020

(86) PCT No.: PCT/CN2020/091441
§ 371 (c)(1),
(2) Date: Nov. 22, 2021

(87) PCT Pub. No.: WO2020/238730
PCT Pub. Date: Dec. 3, 2020

(65) Prior Publication Data
US 2022/0396616 A1     Dec. 15, 2022

(30) Foreign Application Priority Data

May 24, 2019   (CN) ......................... 201910437800.2
May 24, 2019   (CN) ......................... 201910437806.X

(51) Int. Cl.
| | |
|---|---|
| *C07K 16/28* | (2006.01) |
| *A61K 39/00* | (2006.01) |
| *A61P 35/00* | (2006.01) |
| *C07K 16/30* | (2006.01) |
| *C12N 15/70* | (2006.01) |
| *C12N 15/81* | (2006.01) |
| *C12N 15/85* | (2006.01) |

(52) U.S. Cl.
CPC ............. *C07K 16/28* (2013.01); *A61P 35/00* (2018.01); *A61K 39/00* (2013.01); *C07K 2317/24* (2013.01); *C07K 2317/565* (2013.01); *C07K 2317/569* (2013.01)

(58) Field of Classification Search
CPC ............... C07K 16/28; C07K 2317/24; C07K 2317/565; C07K 2317/569; C07K 16/30; C07K 2317/22; C07K 2317/33; C07K 2317/34; C07K 2317/64; C07K 2317/732; C07K 2317/734; C07K 2317/76; C07K 2317/77; C07K 2317/92; A61P 35/00; A61K 39/00; A61K 2039/505; C12N 15/70; C12N 15/81; C12N 15/85
See application file for complete search history.

(56) References Cited

U.S. PATENT DOCUMENTS

| | | | |
|---|---|---|---|
| 8,168,427 | B2 | 5/2012 | Sahin et al. |
| 10,137,195 | B2 | 11/2018 | Sahin et al. |
| 10,421,817 | B1 | 9/2019 | Hu et al. |
| 2016/0347815 | A1 | 12/2016 | Sahin et al. |
| 2018/0319891 | A1 | 11/2018 | Sahin et al. |
| 2019/0233511 | A1 | 8/2019 | Wang et al. |

FOREIGN PATENT DOCUMENTS

| | | |
|---|---|---|
| AU | 2014208256 A1 | 9/2014 |
| CN | 101687929 A | 3/2010 |
| CN | 103509114 A | 1/2014 |
| CN | 104321345 A | 1/2015 |
| CN | 108047331 A | 5/2018 |
| CN | 109762067 A | 5/2019 |
| CN | 109790222 A | 5/2019 |
| EP | 2852408 A1 | 4/2015 |
| JP | 2009-517354 A | 4/2009 |
| JP | 2010-528075 A | 8/2010 |
| JP | 2015-518838 A | 7/2015 |
| JP | 2015-522543 A | 8/2015 |
| WO | 2007/059997 A1 | 5/2007 |
| WO | 2008/145338 A2 | 12/2008 |
| WO | 2013/167259 A1 | 11/2013 |
| WO | 2013/174509 A1 | 11/2013 |
| WO | 2013/174510 A1 | 11/2013 |
| WO | 2018/006882 A1 | 1/2018 |
| WO | 2018/157147 A1 | 8/2018 |

OTHER PUBLICATIONS

Hana et al. Int J Mol Sci. Apr. 24, 2024;25(9):4634. PMID: 38731853 (Year: 2024).*
Sahin et al. Eur J Cancer. Sep. 2018; 100:17-26. PMID: 29936063 (Year: 2018).*
Shitara et al. N Engl J Med. Sep. 26, 2024;391(12):1159-1162. PMID: 39282934 (Year: 2024).*
Allegra et al., Nanobodies and Cancer: Current Status and New Perspectives. Cancer Invest. Apr. 21, 2018;36 (4):221-237.
Bannas et al., Nanobodies and Nanobody-Based Human Heavy Chain Antibodies as Antitumor Therapeutics. Front Immunol. Nov. 22, 2017;8:1603, 13 pages.

(Continued)

*Primary Examiner* — Misook Yu
*Assistant Examiner* — James Lyle McLellan
(74) *Attorney, Agent, or Firm* — McCarter & English, LLP

(57) ABSTRACT

Disclosed is a novel CLDN18.2 binding molecule. Also disclosed are a nucleic acid molecule encoding the CLDN18.2 binding molecule, an expression vector and a host cell for expressing the CLDN18.2 binding molecule. Further disclosed are a method for producing the CLDN18.2 binding molecule and use thereof.

12 Claims, 22 Drawing Sheets

Specification includes a Sequence Listing.

(56) References Cited

OTHER PUBLICATIONS

Natsume et al., Improving effector functions of antibodies for cancer treatment: Enhancing ADCC and CDC. Drug Des Devel Ther. Sep. 21, 2009;3:7-16.

Rudikoff et al., Single amino acid substitution altering antigen-binding specificity. Proc Natl Acad Sci U S A. Mar. 1982;79(6):1979-83.

Sahin et al., Claudin-18 splice variant 2 is a pan-cancer target suitable for therapeutic antibody development. Clin Cancer Res. Dec. 1, 2008;14(23):7624-34.

Tureci et al., Characterization of zolbetuximab in pancreatic cancer models. Oncoimmunology. 2019;8(1):e1523096, 10 pages.

Woll et al., Claudin 18.2 is a target for IMAB362 antibody in pancreatic neoplasms. Int J Cancer. Feb. 1, 2014;134 (3):731-9.

Xu et al., Advances of CLDN18.2 protein in the therapy of malignant tumors. Chin J Clin Oncol. 2019;46(6):311-315.

Ishii et al., Dawn of precision medicine on gastric cancer. Int J Clin Oncol. Jul. 2019;24(7):779-788.

Singh et al., Anti-claudin 18.2 antibody as new targeted therapy for advanced gastric cancer. J Hematol Oncol. May 12, 2017;10(1):105, 5 pages.

International Search Report and Written Opinion for Application No. PCT/CN2020/091441, dated Aug. 19, 2020, 20 pages.

\* cited by examiner

Binding of candidate antibody on human
CLDN18.2-HEK293T cells

Binding of candidate antibody on human
CLDN18.2-KATO III cells

Binding of candidate antibody on human
CLDN18.2-HEK293T cells

Binding of candidate antibody on human
CLDN18.2-HEK293T cells

Binding of candidate antibody on human
CLDN18.2-KATOIII cells

CDC experiment of NA1-S on human
CLDN18.2-HEK293T cells

CDC experiment of NA1-S on human
CLDN18.2-KATOIII cells

CDC experiment of NA3-S on human
CLDN18.2-HEK293T cells

CDC experiment of NA5-S on human
CLDN18.2-HEK293T cells

CDC experiment of NA6-S on human
CLDN18.2-HEK293T cells

CDC experiment of NA3-S on human
CLDN18.2-KATOIII cells

ADCC experiment of NA1-S on human
CLDN18.2-HEK293T cells

ADCC experiment of NA1-S on human
CLDN18.2-KATOIII cells

ADCC experiment of NA3-S on human
CLDN18.2-HEK293T cells

ADCC experiment of NA3-S on human
CLDN18.2-KATOIII cells

Binding assays of NA3-S before and after
humanization on CLDN18.2-HEK293T cells Comparison of binding strength of NA3S-H1 and IMAB362
at different concentrations on CLDN18.1-HEK293T cells Comparison of positive rate of cell binding of 100 μg/mlNA3S-H1
and IMAB362 on CLDN18.1-HEK293T cells CDC cell killing experiment of NA3S-H1 on human
CLDN18.2-KATOIII gastric cancer cells

SEQUENCE LISTING

```
<160> NUMBER OF SEQ ID NOS: 68

<210> SEQ ID NO 1
<211> LENGTH: 8
<212> TYPE: PRT
<213> ORGANISM: Artificial Sequence
<220> FEATURE:
<223> OTHER INFORMATION: Synthesized peptide

<400> SEQUENCE: 1

Gly Asn Ile Phe Arg Ile Asp Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthesized peptide

<400> SEQUENCE: 2

Ile Ser Arg Gly Gly Thr Thr
1               5

<210> SEQ ID NO 3
<211> LENGTH: 15
<212> TYPE: PRT
<213> ORGANISM: Artificial Sequence
<220> FEATURE:
<223> OTHER INFORMATION: Synthesized peptide

<400> SEQUENCE: 3

Asn Ala Gln Ala Trp Asp Pro Gly Thr Phe Arg Tyr Leu Glu Val
1               5                   10                  15
```

```
<210> SEQ ID NO 4
<211> LENGTH: 7
<212> TYPE: PRT
<213> ORGANISM: Artificial Sequence
<220> FEATURE:
<223> OTHER INFORMATION: Synthesized peptide

<400> SEQUENCE: 4

Ile Ser Arg Gly Gly Ser Thr
1               5

<210> SEQ ID NO 5
<211> LENGTH: 15
<212> TYPE: PRT
<213> ORGANISM: Artificial Sequence
<220> FEATURE:
<223> OTHER INFORMATION: Synthesized peptide

<400> SEQUENCE: 5

Asn Ala Gln Ala Trp Asp Pro Gly Thr Ile Arg Tyr Leu Glu Val
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthesized peptide

<400> SEQUENCE: 6

Asn Ala Gln Ala Trp Asp Val Gly Thr Ile Arg Tyr Leu Glu Val
1               5                   10                  15

<210> SEQ ID NO 7
<211> LENGTH: 121
<212> TYPE: PRT
<213> ORGANISM: Artificial Sequence
<220> FEATURE:
<223> OTHER INFORMATION: Synthesized peptide

<400> SEQUENCE: 7

Glu Val Gln Val Gln Glu Ser Gly Gly Gly Leu Val Gln Ala Gly Thr
1               5                   10                  15

Ser Leu Arg Leu Ser Cys Ala Ala Ser Gly Asn Ile Phe Arg Ile Asp
            20                  25                  30

Thr Met Gly Trp Tyr Arg Gln Ala Pro Gly Lys Gln Arg Glu Leu Val
            35                  40                  45

Ala Gly Ile Ser Arg Gly Gly Thr Thr Thr Tyr Ala His Ser Val Lys
        50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95

Ala Gln Ala Trp Asp Pro Gly Thr Phe Arg Tyr Leu Glu Val Trp Gly
                100                 105                 110

Gln Gly Thr Leu Val Thr Val Ser Ala
        115                 120

<210> SEQ ID NO 8
<211> LENGTH: 121
<212> TYPE: PRT
<213> ORGANISM: Artificial Sequence
```

-continued

```
<220> FEATURE:
<223> OTHER INFORMATION: Synthesized peptide

<400> SEQUENCE: 8

Glu Val Gln Val Gln Glu Ser Gly Gly Gly Leu Val Gln Pro Gly Gly
1               5                   10                  15

Ser Leu Arg Leu Ser Cys Ala Ala Ser Gly Asn Ile Phe Arg Ile Asp
            20                  25                  30

Thr Met Gly Trp Tyr Arg Gln Ala Pro Gly Lys Gln Arg Glu Leu Val
        35                  40                  45

Ala Gly Ile Ser Arg Gly Gly Thr Thr Thr Tyr Ala His Ser Val Lys
    50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95

Ala Gln Ala Trp Asp Pro Gly Thr Phe Arg Tyr Leu Glu Val Trp Gly
            100                 105                 110

Gln Gly Thr Leu Val Thr Val Ser Ala
        115                 120

<210> SEQ ID NO 9
<211> LENGTH: 121
<212> TYPE: PRT
<213> ORGANISM: Artificial Sequence
<220> FEATURE:
<223> OTHER INFORMATION: Synthesized peptide

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Arg Ile Asp
            20                  25                  30

Thr Met Gly Trp Tyr Arg Gln Ala Pro Gly Lys Gln Arg Glu Leu Val
        35                  40                  45

Ala Gly Ile Ser Arg Gly Gly Thr Thr Thr Tyr Ala His Ser Val Lys
    50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95

Ala Gln Ala Trp Asp Pro Gly Thr Phe Arg Tyr Leu Glu Val Trp Gly
            100                 105                 110

Gln Gly Thr Leu Val Thr Val Ser Ala
        115                 120

<210> SEQ ID NO 10
<211> LENGTH: 121
<212> TYPE: PRT
<213> ORGANISM: Artificial Sequence
<220> FEATURE:
<223> OTHER INFORMATION: Synthesized peptide

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Arg Ile Asp
            20                  25                  30
```

```
Thr Met Gly Trp Tyr Arg Gln Ala Pro Gly Lys Gln Arg Glu Phe Val
        35                  40                  45

Ala Gly Ile Ser Arg Gly Gly Ser Thr Asn Tyr Ala His Ser Val Lys
        50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95

Ala Gln Ala Trp Asp Pro Gly Thr Ile Arg Tyr Leu Glu Val Trp Gly
            100                 105                 110

Gln Gly Thr Leu Val Thr Val Ser Ser
        115                 120
```

<210> SEQ ID NO 11
<211> LENGTH: 121
<212> TYPE: PRT
<213> ORGANISM: Artificial Sequence
<220> FEATURE:
<223> OTHER INFORMATION: Synthesized peptide

<400> SEQUENCE: 11

```
Glu Val Gln Leu Gln Glu Ser Gly Gly Gly Leu Val Gln Pro Gly Gly
1                   5                   10                  15

Ser Leu Arg Leu Ser Cys Ala Ala Ser Gly Asn Ile Phe Arg Ile Asp
                20                  25                  30

Thr Met Gly Trp Tyr Arg Gln Ala Pro Gly Lys Gln Arg Glu Phe Val
        35                  40                  45

Ala Gly Ile Ser Arg Gly Gly Ser Thr Asn Tyr Ala His Ser Val Lys
        50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95

Ala Gln Ala Trp Asp Pro Gly Thr Ile Arg Tyr Leu Glu Val Trp Gly
            100                 105                 110

Gln Gly Thr Leu Val Thr Val Ser Ala
        115                 120
```

<210> SEQ ID NO 12
<211> LENGTH: 121
<212> TYPE: PRT
<213> ORGANISM: Artificial Sequence
<220> FEATURE:
<223> OTHER INFORMATION: Synthesized peptide

<400> SEQUENCE: 12

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Asn Ile Phe Arg Ile Asp
                20                  25                  30

Thr Met Gly Trp Tyr Arg Gln Ala Pro Gly Lys Gln Arg Glu Phe Val
        35                  40                  45

Ala Gly Ile Ser Arg Gly Gly Ser Thr Asn Tyr Ala His Ser Val Lys
        50                  55                  60

Glu Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Gly Tyr Tyr Cys Asn
                85                  90                  95
```

```
Ala Gln Ala Trp Asp Pro Gly Thr Ile Arg Tyr Leu Glu Val Trp Gly
            100                 105                 110

Gln Gly Thr Leu Val Thr Val Ser Ala
        115                 120

<210> SEQ ID NO 13
<211> LENGTH: 121
<212> TYPE: PRT
<213> ORGANISM: Artificial Sequence
<220> FEATURE:
<223> OTHER INFORMATION: Synthesized peptide

<400> SEQUENCE: 13

Glu Val Gln Val Val Glu Ser Gly Gly Gly Leu Val Gln Pro Gly Gly
1               5                   10                  15

Ser Leu Arg Leu Ser Cys Ala Ala Ser Gly Asn Ile Phe Arg Ile Asp
            20                  25                  30

Thr Met Val Trp Tyr Arg Gln Ala Pro Gly Lys Gln Arg Glu Leu Val
        35                  40                  45

Ala Gly Ile Ser Arg Gly Gly Thr Thr Asn Tyr Ala His Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Thr Tyr Tyr Cys Asn
            85                  90                  95

Ala Gln Ala Trp Asp Val Gly Thr Ile Arg Tyr Leu Glu Val Trp Gly
            100                 105                 110

Gln Gly Thr Leu Val Thr Val Ser Ala
        115                 120

<210> SEQ ID NO 14
<211> LENGTH: 121
<212> TYPE: PRT
<213> ORGANISM: Artificial Sequence
<220> FEATURE:
<223> OTHER INFORMATION: Synthesized peptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Arg Ile Asp
            20                  25                  30

Thr Met Val Trp Tyr Arg Gln Ala Pro Gly Lys Gln Arg Glu Leu Val
        35                  40                  45

Ala Gly Ile Ser Arg Gly Gly Thr Thr Asn Tyr Ala His Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Ser Glu Asp Thr Ala Thr Tyr Tyr Cys Asn
            85                  90                  95

Ala Gln Ala Trp Asp Val Gly Thr Ile Arg Tyr Leu Glu Val Trp Gly
            100                 105                 110

Gln Gly Thr Leu Val Thr Val Ser Ala
        115                 120

<210> SEQ ID NO 15
<211> LENGTH: 261
<212> TYPE: PRT
```

```
<213> ORGANISM: Homo sapiens

<400> SEQUENCE: 15

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 16
<211> LENGTH: 261
<212> TYPE: PRT
<213> ORGANISM: Homo sapiens

<400> SEQUENCE: 16

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
```

-continued

```
                    85               90               95
Ser Ile Phe Ala Leu Lys Cys Ile Arg Ile Gly Ser Met Glu Asp Ser
                100              105              110

Ala Lys Ala Asn Met Thr Leu Thr Ser Gly Ile Met Phe Ile Val Ser
            115              120              125

Gly Leu Cys Ala Ile Ala Gly Val Ser Val Phe Ala Asn Met Leu Val
        130              135              140

Thr Asn Phe Trp Met Ser Thr Ala Asn Met Tyr Thr Gly Met Gly Gly
145              150              155              160

Met Val Gln Thr Val Gln Thr Arg Tyr Thr Phe Gly Ala Ala Leu Phe
                165              170              175

Val Gly Trp Val Ala Gly Gly Leu Thr Leu Ile Gly Gly Val Met Met
                180              185              190

Cys Ile Ala Cys Arg Gly Leu Ala Pro Glu Glu Thr Asn Tyr Lys Ala
                195              200              205

Val Ser Tyr His Ala Ser Gly His Ser Val Ala Tyr Lys Pro Gly Gly
        210              215              220

Phe Lys Ala Ser Thr Gly Phe Gly Ser Asn Thr Lys Asn Lys Lys Ile
225              230              235              240

Tyr Asp Gly Gly Ala Arg Thr Glu Asp Glu Val Gln Ser Tyr Pro Ser
                245              250              255

Lys His Asp Tyr Val
                260

<210> SEQ ID NO 17
<211> LENGTH: 264
<212> TYPE: PRT
<213> ORGANISM: Mus musculus

<400> SEQUENCE: 17

Met Ser Val Thr Ala Cys Gln Gly Leu Gly Phe Val Val Ser Leu Ile
1               5               10               15

Gly Phe Ala Gly Ile Ile Ala Ala Thr Cys Met Asp Gln Trp Ser Thr
                20              25              30

Gln Asp Leu Tyr Asn Asn Pro Val Thr Ala Val Phe Asn Tyr Gln Gly
        35              40              45

Leu Trp Arg Ser Cys Val Arg Glu Ser Ser Gly Phe Thr Glu Cys Arg
        50              55              60

Gly Tyr Phe Thr Leu Leu Gly Leu Pro Ala Met Leu Gln Ala Val Arg
65              70              75              80

Ala Leu Met Ile Val Gly Ile Val Leu Gly Val Ile Gly Ile Leu Val
                85              90               95

Ser Ile Phe Ala Leu Lys Cys Ile Arg Ile Gly Ser Met Asp Asp Ser
                100              105              110

Ala Lys Ala Lys Met Thr Leu Thr Ser Gly Ile Leu Phe Ile Ile Ser
            115              120              125

Gly Ile Cys Ala Ile Ile Gly Val Ser Val Phe Ala Asn Met Leu Val
        130              135              140

Thr Asn Phe Trp Met Ser Thr Ala Asn Met Tyr Ser Gly Met Gly Gly
145              150              155              160

Met Gly Gly Met Val Gln Thr Val Gln Thr Arg Tyr Thr Phe Gly Ala
                165              170              175

Ala Leu Phe Val Gly Trp Val Ala Gly Gly Leu Thr Leu Ile Gly Gly
        180              185              190
```

-continued

```
Val Met Met Cys Ile Ala Cys Arg Gly Leu Thr Pro Asp Asp Ser Asn
        195                 200                 205

Phe Lys Ala Val Ser Tyr His Ala Ser Gly Gln Asn Val Ala Tyr Arg
        210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
                260

<210> SEQ ID NO 18
<211> LENGTH: 264
<212> TYPE: PRT
<213> ORGANISM: Mus musculus

<400> SEQUENCE: 18

Met Ala Thr Thr Thr Cys Gln Val Val Gly Leu Leu Leu Ser Leu Leu
1               5                   10                  15

Gly Leu Ala Gly Cys Ile Ala Ala Thr Gly Met Asp Met Trp Ser Thr
        20                  25                  30

Gln Asp Leu Tyr Asp Asn Pro Val Thr Ala Val Phe Gln Tyr Glu Gly
        35                  40                  45

Leu Trp Arg Ser Cys Val Gln Gln Ser Ser Gly Phe Thr Glu Cys Arg
        50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Val Ile Gly Ile Leu Val
                85                  90                  95

Ser Ile Phe Ala Leu Lys Cys Ile Arg Ile Gly Ser Met Asp Asp Ser
        100                 105                 110

Ala Lys Ala Lys Met Thr Leu Thr Ser Gly Ile Leu Phe Ile Ile Ser
        115                 120                 125

Gly Ile Cys Ala Ile Ile Gly Val Ser Val Phe Ala Asn Met Leu Val
        130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
                180                 185                 190

Val Met Met Cys Ile Ala Cys Arg Gly Leu Thr Pro Asp Asp Ser Asn
        195                 200                 205

Phe Lys Ala Val Ser Tyr His Ala Ser Gly Gln Asn Val Ala Tyr Arg
        210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
                260

<210> SEQ ID NO 19
<211> LENGTH: 53
<212> TYPE: PRT
<213> ORGANISM: Homo sapiens
```

-continued

<400> SEQUENCE: 19

```
Asp Gln Trp Ser Thr Gln Asp Leu Tyr Asn Asn Pro Val Thr Ala Val
1               5                   10                  15

Phe Asn Tyr Gln Gly Leu Trp Arg Ser Cys Val Arg Glu Ser Ser Gly
            20                  25                  30

Phe Thr Glu Cys Arg Gly Tyr Phe Thr Leu Leu Gly Leu Pro Ala Met
        35                  40                  45

Leu Gln Ala Val Arg
    50
```

<210> SEQ ID NO 20
<211> LENGTH: 232
<212> TYPE: PRT
<213> ORGANISM: Homo sapiens

<400> SEQUENCE: 20

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 21
<211> LENGTH: 14
<212> TYPE: PRT
<213> ORGANISM: Artificial Sequence
<220> FEATURE:
<223> OTHER INFORMATION: Synthesized peptide

<400> SEQUENCE: 21

```
Gly Phe Lys Ala Ser Thr Gly Phe Gly Ser Asn Thr Lys Asn
```

-continued

```
1              5              10
```

```
<210> SEQ ID NO 22
<211> LENGTH: 360
<212> TYPE: DNA
<213> ORGANISM: Artificial Sequence
<220> FEATURE:
<223> OTHER INFORMATION: Synthesized sequence

<400> SEQUENCE: 22
gaggtgcagg tgcaggagtc tggggggaggc ctggtacagg ctgggacctc tctgagactc      60
tcctgtgcag cctctggcaa catcttccgt atcgatacca tgggctggta ccgccaggct     120
ccaggaaagc agcgcgagtt ggtcgcaggt atttctcgtg gtggtacaac aacctatgca     180
cactccgtga aggaacgatt caccatctcc agagacaacg ccaagaacac gatgtatctg     240
caaatgaaca gcctgaaatc tgaggacacg gccggctatt attgtaatgc acaggcgtgg     300
gatcctggta catttcggta tctcgaagtt tggggccagg gcaccctggt cactgtctca     360

<210> SEQ ID NO 23
<211> LENGTH: 360
<212> TYPE: DNA
<213> ORGANISM: Artificial Sequence
<220> FEATURE:
<223> OTHER INFORMATION: Synthesized sequence

<400> SEQUENCE: 23
gaggtgcagt tggtggagtc tggggggaggc ttggtacagc ctgggggggtc tctgagactc      60 tcctgtgcag cctctggcaa catcttccgt atcgatacca tgggctggta ccgccaggct     120
ccaggaaagc agcgcgagtt cgtcgcaggt attagtcgtg gtggtagcac aaactatgca     180
cactccgtga aggaacgatt caccatctcc agagacaacg ccaagaacac gatgtatctg     240
caaatgaaca gcctgaaatc tgaggacacg gccggctatt attgtaatgc acaggcgtgg     300
gatcctggta caatccggta tctcgaagtt tggggccagg gcaccctggt cactgtctca     360

<210> SEQ ID NO 24
<211> LENGTH: 360
<212> TYPE: DNA
<213> ORGANISM: Artificial Sequence
<220> FEATURE:
<223> OTHER INFORMATION: Synthesized sequence

<400> SEQUENCE: 24
gaggtgcagg tgcaggagtc tggggggaggc ttggtacagc ctgggggggtc tctgagactc      60 tcctgtgcag cctctggcaa catcttccgt atcgatacca tgggctggta ccgccaggct     120
ccaggaaagc agcgcgagtt ggtcgcaggt atttctcgtg gtggtacaac aacctatgca     180
cactccgtga aggaacgatt caccatctcc agagacaacg ccaagaacac gatgtatctg     240
caaatgaaca gcctgaaatc tgaggacacg gccggctatt attgtaatgc acaggcgtgg     300
gatcctggta catttcggta tctcgaagtt tggggccagg gcaccctggt cactgtctca     360

<210> SEQ ID NO 25
<211> LENGTH: 363
<212> TYPE: DNA
<213> ORGANISM: Artificial Sequence
<220> FEATURE:
<223> OTHER INFORMATION: Synthesized sequence

<400> SEQUENCE: 25
caggtgcagc tcgtggagtc tggggggaggc ttggtacagc ctgggggggtc tctgagactc      60
```

```
tcctgtgcag cctctggcaa catcttccgt atcgatacca tgggctggta ccgccaggct        120
ccaggaaagc agcgcgagtt cgtcgcaggt attagtcgtg gtggtagcac aaactatgca        180
cactccgtga aggaacgatt caccatctcc agagacaacg ccaagaacac gatgtatctg        240
caaatgaaca gcctgaaatc tgaggacacg gccggctatt attgtaatgc acaggcgtgg        300
gatcctggta caatccggta tctcgaagtt tggggccagg gcaccctggt caccgtgtcc        360
tca                                                                       363
```

<210> SEQ ID NO 26
<211> LENGTH: 360
<212> TYPE: DNA
<213> ORGANISM: Artificial Sequence
<220> FEATURE:
<223> OTHER INFORMATION: Synthesized sequence

<400> SEQUENCE: 26

```
caggtgcagc tcgtggagtc tggggggaggc ttggtacagc ctggggggtc tctgagactc         60
tcctgtgcag cctctggcaa catcttccgt atcgatacca tgggctggta ccgccaggct        120
ccaggaaagc agcgcgagtt ggtcgcaggt atttctcgtg gtggtacaac aacctatgca        180
cactccgtga aggaacgatt caccatctcc agagacaacg ccaagaacac gatgtatctg        240
caaatgaaca gcctgaaatc tgaggacacg gccggctatt attgtaatgc acaggcgtgg        300
gatcctggta catttcggta tctcgaagtt tggggccagg gcaccctggt cactgtctca        360
```

<210> SEQ ID NO 27
<211> LENGTH: 360
<212> TYPE: DNA
<213> ORGANISM: Artificial Sequence
<220> FEATURE:
<223> OTHER INFORMATION: Synthesized sequence

<400> SEQUENCE: 27

```
gaggtgcagt tggtggagtc tggggggaggc ttggtacagc ctggggggtc tctgagactc         60
tcctgtgcag cctctggcaa catcttccgt atcgatacca tggtgtggta ccgccaggct        120
ccaggaaagc agcgcgagtt ggtcgcaggt atttctcgtg gtggtaccac aaactatgca        180
cactccgtga agggccgatt caccatctcc agagacaacg ccaagaacac gatgtatctg        240
caaatgaaca gcctgaaatc tgaggacacg gccacgtatt attgtaatgc acaggcgtgg        300
gatgttggta caatccggta tctcgaagtt tggggccagg gcaccctggt cactgtctca        360
```

<210> SEQ ID NO 28
<211> LENGTH: 360
<212> TYPE: DNA
<213> ORGANISM: Artificial Sequence
<220> FEATURE:
<223> OTHER INFORMATION: Synthesized sequence

<400> SEQUENCE: 28

```
gaggtgcagc tgcaggagtc tggggggaggc ttggtacagc ctggggggtc tctgagactc         60
tcctgtgcag cctctggcaa catcttccgt atcgatacca tgggctggta ccgccaggct        120
ccaggaaagc agcgcgagtt cgtcgcaggt attagtcgtg gtggtagcac aaactatgca        180
cactccgtga aggaacgatt caccatctcc agagacaacg ccaagaacac gatgtatctg        240
caaatgaaca gcctgaaatc tgaggacacg gccggctatt attgtaatgc acaggcgtgg        300
gatcctggta caatccggta tctcgaagtt tggggccagg gcaccctggt cactgtctca        360
```

-continued

```
<210> SEQ ID NO 29
<211> LENGTH: 360
<212> TYPE: DNA
<213> ORGANISM: Artificial Sequence
<220> FEATURE:
<223> OTHER INFORMATION: Synthesized sequence

<400> SEQUENCE: 29
gaggtgcagg tcgtggagtc tggggggaggc ttggtacagc ctggggggtc tctgagactc      60
tcctgtgcag cctctggcaa catcttccgt atcgatacca tggtgtggta ccgccaggct     120
ccaggaaagc agcgcgagtt ggtcgcaggt atttctcgtg gtggtaccac aaactatgca     180
cactccgtga agggccgatt caccatctcc agagacaacg ccaagaacac gatgtatctg     240
caaatgaaca gcctgaaatc tgaggacacg gccacgtatt attgtaatgc acaggcgtgg     300
gatgttggta caatccggta tctcgaagtt tggggccagg gcaccctggt cactgtctca     360

<210> SEQ ID NO 30
<211> LENGTH: 8
<212> TYPE: PRT
<213> ORGANISM: Artificial Sequence
<220> FEATURE:
<223> OTHER INFORMATION: Synthesized peptide

<400> SEQUENCE: 30

Gly Ser Ile Phe Asn Ile Pro Val
1               5

<210> SEQ ID NO 31
<211> LENGTH: 7
<212> TYPE: PRT
<213> ORGANISM: Artificial Sequence
<220> FEATURE:
<223> OTHER INFORMATION: Synthesized peptide

<400> SEQUENCE: 31

Ile Ser Thr Gly Gly Thr Thr
1               5

<210> SEQ ID NO 32
<211> LENGTH: 14
<212> TYPE: PRT
<213> ORGANISM: Artificial Sequence
<220> FEATURE:
<223> OTHER INFORMATION: Synthesized peptide

<400> SEQUENCE: 32

Asn Val Leu Val Val Ser Gly Ile Gly Ser Thr Leu Glu Val
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Synthesized peptide

<400> SEQUENCE: 33

Gly Ser Ile Phe Asn Leu Pro Val
1               5

<210> SEQ ID NO 34
<211> LENGTH: 8
<212> TYPE: PRT
<213> ORGANISM: Artificial Sequence
```

```
<220> FEATURE:
<223> OTHER INFORMATION: Synthesized peptide

<400> SEQUENCE: 34

Gly Thr Ile Phe Asn Ile Pro Val
1               5

<210> SEQ ID NO 35
<211> LENGTH: 8
<212> TYPE: PRT
<213> ORGANISM: Artificial Sequence
<220> FEATURE:
<223> OTHER INFORMATION: Synthesized peptide

<400> SEQUENCE: 35

Gly Ile Ile Phe Asn Ile Pro Val
1               5

<210> SEQ ID NO 36
<211> LENGTH: 8
<212> TYPE: PRT
<213> ORGANISM: Artificial Sequence
<220> FEATURE:
<223> OTHER INFORMATION: Synthesized peptide

<400> SEQUENCE: 36

Gly Thr Ile Phe Asn Leu Pro Val
1               5

<210> SEQ ID NO 37
<211> LENGTH: 14
<212> TYPE: PRT
<213> ORGANISM: Artificial Sequence
<220> FEATURE:
<223> OTHER INFORMATION: Synthesized peptide

<400> SEQUENCE: 37

Asn Val Leu Val Ile Ser Gly Ile Gly Ser His Leu Glu Val
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthesized peptide

<400> SEQUENCE: 38

Gly Ser Ile Leu His Ile Pro Val
1               5

<210> SEQ ID NO 39
<211> LENGTH: 8
<212> TYPE: PRT
<213> ORGANISM: Artificial Sequence
<220> FEATURE:
<223> OTHER INFORMATION: Synthesized peptide

<400> SEQUENCE: 39

Gly Ser Ile Phe His Ile Val Val
1               5

<210> SEQ ID NO 40
<211> LENGTH: 8
<212> TYPE: PRT
<213> ORGANISM: Artificial Sequence
<220> FEATURE:
```

<223> OTHER INFORMATION: Synthesized peptide

<400> SEQUENCE: 40

Gly Thr Phe Phe Asn Ile Pro Val
1               5

<210> SEQ ID NO 41
<211> LENGTH: 7
<212> TYPE: PRT
<213> ORGANISM: Artificial Sequence
<220> FEATURE:
<223> OTHER INFORMATION: Synthesized peptide

<400> SEQUENCE: 41

Met Ser Thr Gly Gly Thr Thr
1               5

<210> SEQ ID NO 42
<211> LENGTH: 119
<212> TYPE: PRT
<213> ORGANISM: Artificial Sequence
<220> FEATURE:
<223> OTHER INFORMATION: Synthesized peptide

<400> SEQUENCE: 42

Glu Val Gln Val Gln Glu Ser Gly Gly Gly Leu Val Gln Pro Gly Gly
1               5                   10                  15

Ser Leu Arg Leu Ser Cys Ala Ala Ser Gly Ser Ile Phe Asn Ile Pro
            20                  25                  30

Val Met Ser Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Ile Ser Gly Ile Gly Ser His Leu Glu Val Trp Gly Gln
            100                 105                 110

Gly Thr Leu Val Thr Val Ser
        115

<210> SEQ ID NO 43
<211> LENGTH: 119
<212> TYPE: PRT
<213> ORGANISM: Artificial Sequence
<220> FEATURE:
<223> OTHER INFORMATION: Synthesized peptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn Leu Pro
            20                  25                  30

Val Met Ser Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Ile Ser Gly Ile Gly Ser His Leu Glu Val Trp Gly Gln
            100                 105                 110

Gly Thr Leu Val Thr Val Ser
        115

<210> SEQ ID NO 44
<211> LENGTH: 119
<212> TYPE: PRT
<213> ORGANISM: Artificial Sequence
<220> FEATURE:
<223> OTHER INFORMATION: Synthesized peptide

<400> SEQUENCE: 44

Gln Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Asn Ile Pro
            20                  25                  30

Val Met Gly Trp Tyr Arg Gln Ala Pro Gly Lys Gln Arg Glu Leu Val
            35                  40                  45

Ala Gly Ile Ser Thr Gly Gly Thr Thr Asn Tyr Gly Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Ile Ser Gly Ile Gly Ser His Leu Glu Val Trp Gly Gln
            100                 105                 110

Gly Thr Leu Val Thr Val Ser
        115

<210> SEQ ID NO 45
<211> LENGTH: 119
<212> TYPE: PRT
<213> ORGANISM: Artificial Sequence
<220> FEATURE:
<223> OTHER INFORMATION: Synthesized peptide

<400> SEQUENCE: 45

Glu Val Gln Leu Gln Glu Ser Gly Gly Gly Leu Val Gln Pro Gly Gly
1               5                   10                  15

Ser Leu Arg Leu Ser Cys Ala Ala Ser Gly Ile Ile Phe Asn Ile Pro
            20                  25                  30

Val Met Ser Trp Tyr Arg Gln Ala Pro Gly Lys Gln Arg Glu Leu Val
            35                  40                  45

Ala Gly Ile Ser Thr Gly Gly Thr Thr Asn Tyr Gly Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Val Ser Gly Ile Gly Ser His Leu Glu Val Trp Gly Gln
            100                 105                 110

Gly Thr Leu Val Thr Val Ser
        115

<210> SEQ ID NO 46

<211> LENGTH: 119
<212> TYPE: PRT
<213> ORGANISM: Artificial Sequence
<220> FEATURE:
<223> OTHER INFORMATION: Synthesized peptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn Leu Pro
            20                  25                  30

Val Met Ser Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Val Ser Gly Ile Gly Ser His Leu Glu Val Trp Gly Gln
            100                 105                 110

Gly Thr Leu Val Thr Val Ser
        115

<210> SEQ ID NO 47
<211> LENGTH: 119
<212> TYPE: PRT
<213> ORGANISM: Artificial Sequence
<220> FEATURE:
<223> OTHER INFORMATION: Synthesized peptide

<400> SEQUENCE: 47

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Asn Ile Pro
            20                  25                  30

Val Met Gly Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Val Ser Gly Ile Gly Ser Thr Leu Glu Val Trp Gly Gln
            100                 105                 110

Gly Thr Leu Val Thr Val Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthesized peptide

<400> SEQUENCE: 48

Glu Val Gln Leu Gln Glu Ser Gly Gly Gly Leu Val Gln Pro Gly Gly
1               5                   10                  15

```
Ser Leu Arg Leu Ser Cys Ala Ala Ser Gly Thr Ile Phe Asn Leu Pro
            20                  25                  30

Val Met Ser Trp Tyr Arg Gln Ala Pro Gly Lys Gln Arg Glu Leu Val
            35                  40                  45

Ala Gly Ile Ser Thr Gly Gly Thr Thr Asn Tyr Gly Asp Ser Val Lys
            50                  55                  60

Gly Arg Phe Thr Ile Ser Arg Asp Asn Ala Arg Asn Thr Val Tyr Leu
65                      70                  75                  80

Gln Met Asn Ser Leu Lys Pro Glu Asp Thr Ala Val Tyr Tyr Cys Asn
                    85                  90                  95

Val Leu Val Val Ser Gly Ile Gly Ser His Leu Glu Val Trp Gly Gln
                    100                 105                 110

Gly Thr Leu Val Thr Val Ser
            115
```

```
<210> SEQ ID NO 49
<211> LENGTH: 120
<212> TYPE: PRT
<213> ORGANISM: Artificial Sequence
<220> FEATURE:
<223> OTHER INFORMATION: Synthesized peptide

<400> SEQUENCE: 49
```

```
Glu Val Gln Val Val Glu Ser Gly Gly Gly Leu Val Gln Pro Gly Gly
1                   5                   10                  15

Ser Leu Arg Leu Ser Cys Ala Ala Ser Gly Ser Ile Leu His Ile Pro
            20                  25                  30

Val Met Ser Trp Tyr Arg Gln Ala Pro Gly Lys Gln Arg Glu Leu Val
            35                  40                  45

Ala Gly Ile Ser Thr Gly Gly Thr Thr Asn Tyr Gly Asp Ser Val Lys
            50                  55                  60

Gly Arg Phe Thr Ile Ser Arg Asp Asn Ala Lys Asn Thr Val Tyr Leu
65                      70                  75                  80

Gln Met Asn Ser Leu Lys Pro Glu Asp Thr Ala Ala Tyr Tyr Cys Asn
                    85                  90                  95

Val Leu Val Val Ser Gly Ile Gly Ser His Leu Glu Val Trp Gly Gln
                    100                 105                 110

Gly Thr Leu Val Thr Val Ser Ser
            115                 120
```

```
<210> SEQ ID NO 50
<211> LENGTH: 119
<212> TYPE: PRT
<213> ORGANISM: Artificial Sequence
<220> FEATURE:
<223> OTHER INFORMATION: Synthesized peptide

<400> SEQUENCE: 50
```

```
Gln Val Gln Leu Val Glu Ser Gly Gly Gly Ser Val Gln Pro Gly Gly
1                   5                   10                  15

Ser Leu Arg Leu Ser Cys Ala Ala Ser Gly Ser Ile Phe His Ile Val
            20                  25                  30

Val Met Gly Trp Tyr Arg Gln Ala Pro Gly Lys Gln Arg Glu Leu Val
            35                  40                  45

Ala Gly Met Ser Thr Gly Gly Thr Thr Asn Tyr Gly Asp Ser Val Lys
            50                  55                  60

Gly Arg Phe Thr Ile Ser Arg Asp Asn Ala Lys Asn Thr Val Tyr Leu
65                      70                  75                  80
```

```
Gln Met Asn Ser Leu Lys Pro Glu Asp Thr Ala Val Tyr Tyr Cys Asn
                85                  90                  95

Val Leu Val Ile Ser Gly Ile Gly Ser His Leu Glu Val Trp Gly Gln
            100                 105                 110

Gly Thr Leu Val Thr Val Ser
        115
```

<210> SEQ ID NO 51
<211> LENGTH: 119
<212> TYPE: PRT
<213> ORGANISM: Artificial Sequence
<220> FEATURE:
<223> OTHER INFORMATION: Synthesized peptide

<400> SEQUENCE: 51

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Thr Phe Phe Asn Ile Pro
            20                  25                  30

Val Met Gly Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Ile Ser Gly Ile Gly Ser His Leu Glu Val Trp Gly Gln
            100                 105                 110

Gly Thr Leu Val Thr Val Ser
        115
```

<210> SEQ ID NO 52
<211> LENGTH: 360
<212> TYPE: DNA
<213> ORGANISM: Artificial Sequence
<220> FEATURE:
<223> OTHER INFORMATION: Synthesized sequence

<400> SEQUENCE: 52

```
gaggtgcagg tgcaggagtc tgggggaggc ctggtacagg ctgggacctc tctgagactc      60
tcctgtgcag cctctggcaa catcttccgt atcgatacca tgggctggta ccgccaggct     120
ccaggaaagc agcgcgagtt ggtcgcaggt atttctcgtg gtggtacaac aacctatgca     180
cactccgtga aggaacgatt caccatctcc agagacaacg ccaagaacac gatgtatctg     240
caaatgaaca gcctgaaatc tgaggacacg gccggctatt attgtaatgc acaggcgtgg     300
gatcctggta catttcggta tctcgaagtt tggggccagg gcaccctggt cactgtctca     360
```

<210> SEQ ID NO 53
<211> LENGTH: 360
<212> TYPE: DNA
<213> ORGANISM: Artificial Sequence
<220> FEATURE:
<223> OTHER INFORMATION: Synthesized sequence

<400> SEQUENCE: 53

```
gaggtgcagg tggtggagtc tgggggaggc ttggtgcagc cggggggtc tctgagactc       60 tcctgtgcag cctctggaag catcttgcat atccctgtca tgagctggta ccgccaggct     120
```

-continued

```
ccagggaagc agcgcgagtt ggtcgcaggt attagtaccg gtggtactac aaactatgga      180
gactccgtga agggccgatt caccatctcc agagacaacg ccaagaacac ggtgtatctg      240
caaatgaaca gcctgaaacc tgaagacacg gccgcttatt actgtaatgt cctggtagta      300
agtggtattg ggagccatct cgaagtttgg ggccagggca ccctggtcac cgtgtcctca      360

<210> SEQ ID NO 54
<211> LENGTH: 357
<212> TYPE: DNA
<213> ORGANISM: Artificial Sequence
<220> FEATURE:
<223> OTHER INFORMATION: Synthesized sequence

<400> SEQUENCE: 54
gaggtgcagt tggtggagtc tgggggaggc ttggtgcagc ccgggggtc tctgagactc         60 tcctgtgcag cctctggaag catcttcaat cttcctgtca tgagctggta ccgccaggct        120
ccagggaagc agcgcgagtt ggtcgcagga attagtaccg gaggtactac aaactatgga       180
gactccgtga agggccgatt caccatctcc agagacaacg ccaagaacac ggtgtatctg       240
caaatgaaca gcctgaaacc tgaagacacg gccgtctatt actgtaatgt cctggtaata      300
agtggtattg ggagccatct cgaagtttgg ggccagggca ccctggtcac tgtctca         357

<210> SEQ ID NO 55
<211> LENGTH: 357
<212> TYPE: DNA
<213> ORGANISM: Artificial Sequence
<220> FEATURE:
<223> OTHER INFORMATION: Synthesized sequence

<400> SEQUENCE: 55
gaggtgcagc tgcaggagtc tgggggaggc ttggtgcagc ccgggggtc tctgagactc         60 tcctgtgcag cctctggaat catcttcaat atccctgtca tgagctggta ccgccaggct        120
ccagggaagc agcgcgagtt ggtcgcaggt attagtaccg gtggtactac aaactatgga       180
gactccgtga agggccgatt caccatctcc agagacaacg ccaagaacac ggtgtatctg       240
caaatgaaca gcctgaaacc tgaagacacg gccgtctatt actgtaatgt cctggtagta      300
agtggtattg ggagccatct cgaagtttgg ggccagggca ccctggtcac tgtctca         357

<210> SEQ ID NO 56
<211> LENGTH: 357
<212> TYPE: DNA
<213> ORGANISM: Artificial Sequence
<220> FEATURE:
<223> OTHER INFORMATION: Synthesized sequence

<400> SEQUENCE: 56
gaggtgcagg tgcaggagtc tgggggaggc ttggtgcagc ccgggggggtc tctgagactc        60 tcctgtgcag cctctggaag catcttcaat atccctgtca tgagctggta ccgccaggct        120
ccagggaagc agcgcgagtt ggtcgcaggt attagtaccg gtggtactac aaactatgga       180
gactccgtga agggccgatt caccatctcc agagacaacg ccaagaccac ggtgtatctg       240
caaatgaaca gcctgaaacc tgaagacacg gccgtctatt actgtaatgt cctggtaata      300
agtggtattg ggagccatct cgaagtttgg ggccagggca ccctggtcac tgtctca         357

<210> SEQ ID NO 57
<211> LENGTH: 357
<212> TYPE: DNA
```

```
<213> ORGANISM: Artificial Sequence
<220> FEATURE:
<223> OTHER INFORMATION: Synthesized sequence

<400> SEQUENCE: 57
caggtgcagc tggtggagtc tggggggaggc ttggtgcagc ccggggggtc tctgagactc      60
tcctgtgcag cctctggaac catcttcaat atccctgtca tgggctggta ccgccaggct     120
ccagggaagc agcgcgagtt ggtcgcaggt attagtactg gtggtactac aaactatgga     180
gactccgtga agggccgatt caccatctcc agagacaacg ccaagaacac ggtgtatctg     240
cagatgaaca gcctgaaacc tgaagacacg gccgtctatt actgtaatgt cctggtaata     300
agtggtattg ggagccatct cgaagtttgg ggccagggca ccctggtcac tgtctca       357

<210> SEQ ID NO 58
<211> LENGTH: 357
<212> TYPE: DNA
<213> ORGANISM: Artificial Sequence
<220> FEATURE:
<223> OTHER INFORMATION: Synthesized sequence

<400> SEQUENCE: 58
caggtgcagc tgcaggagtc tggggggaggc ttggtgcagc ccggggggtc tctgagactc      60
tcctgtgcag cctctggaag catcttcaat atccctgtca tgggctggta ccgccaggct     120
ccagggaagc agcgcgagtt ggtcgcaggt attagtactg gtggtactac aaactatgga     180
gactccgtga agggccgatt caccatctcc agagacaacg ccaagaacac ggtgtatctg     240
caaatgaaca gcctgaaacc tgaagacacg gccgtctatt actgtaatgt cctggtagta     300
agtggtattg ggagcactct cgaagtttgg ggccagggca ccctggtcac tgtctca       357

<210> SEQ ID NO 59
<211> LENGTH: 357
<212> TYPE: DNA
<213> ORGANISM: Artificial Sequence
<220> FEATURE:
<223> OTHER INFORMATION: Synthesized sequence

<400> SEQUENCE: 59
gaggtgcagc tgcaggagtc tggggggaggc ttggtgcagc ccggggggtc tctgagactc      60
tcctgtgcag cctctggaac catcttcaat ctccctgtca tgagctggta ccgccaggct     120
ccagggaagc agcgcgagtt ggtcgcaggt attagtaccg gtggtactac aaattatgga     180
gactccgtga agggacgatt caccatctcc agagacaacg ccaggaacac ggtgtatctg     240
caaatgaaca gcctgaaacc tgaagacacg gccgtctatt actgtaatgt cctggtagta     300
agtggtattg ggagccatct cgaagtttgg ggccagggca ccctggtcac tgtctca       357

<210> SEQ ID NO 60
<211> LENGTH: 357
<212> TYPE: DNA
<213> ORGANISM: Artificial Sequence
<220> FEATURE:
<223> OTHER INFORMATION: Synthesized sequence

<400> SEQUENCE: 60
caggtgcagc tgcaggagtc tggggggaggc ttggtgcagc ccggggggtc tctgagactc      60
tcctgtgcag cctctggaac cttcttcaat atccctgtca tgggctggta ccgccaggct     120
ccagggaagc agcgcgagtt ggtcgcaggt attagtaccg gtggtactac aaactatgga     180
gactccgtga agggccgatt caccatctcc agagacaacg ccaagaacac ggtgtatctg     240
```

```
cagatgaaca gcctgaaacc tgaagacacg gccgtctatt actgtaatgt cctggtaata      300
agtggtattg ggagccatct cgaagtttgg ggccagggca ccctggtcac tgtctca        357
```

<210> SEQ ID NO 61
<211> LENGTH: 357
<212> TYPE: DNA
<213> ORGANISM: Artificial Sequence
<220> FEATURE:
<223> OTHER INFORMATION: Synthesized sequence

<400> SEQUENCE: 61

```
caggtgcagc tggtagagtc tggggggaggc tcggtgcagc ccgggggggtc tctgagactc      60 tcctgtgcag cctctggaag catcttccat atcgttgtca tgggctggta ccgccaggct      120
ccagggaagc agcgcgagtt ggtcgcaggt atgagtaccg gtggtactac aaactatgga      180
gactccgtga agggccgatt caccatctcc agagacaacg ccaagaacac ggtgtatctg      240
caaatgaaca gcctgaaacc tgaagacacg gccgtctact actgtaatgt cctggtaatt      300
agtggtattg ggagccatct cgaagtttgg ggccagggca ccctggtcac tgtctca        357
```

<210> SEQ ID NO 62
<211> LENGTH: 14
<212> TYPE: PRT
<213> ORGANISM: Artificial Sequence
<220> FEATURE:
<223> OTHER INFORMATION: Synthesized peptide

<400> SEQUENCE: 62

```
Asn Val Leu Val Val Ser Gly Ile Gly Ser His Leu Glu Val
1               5                   10
```

<210> SEQ ID NO 63
<211> LENGTH: 120
<212> TYPE: PRT
<213> ORGANISM: Artificial Sequence
<220> FEATURE:
<223> OTHER INFORMATION: Synthesized peptide

<400> SEQUENCE: 63

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn Ile Pro
            20                  25                  30

Val Met Gly Trp Tyr Arg Gln Ala Pro Gly Lys Gln Arg Glu Leu Val
        35                  40                  45

Ala Gly Ile Ser Thr Gly Gly Thr Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Leu Val Val Ser Gly Ile Gly Ser Thr Leu Glu Val Trp Gly Gln
            100                 105                 110

Gly Thr Leu Val Thr Val Ser Ser
        115                 120
```

<210> SEQ ID NO 64
<211> LENGTH: 360
<212> TYPE: DNA
<213> ORGANISM: Artificial Sequence -continued
<220> FEATURE:
<223> OTHER INFORMATION: Synthesized sequence

<400> SEQUENCE: 64
caggtgcagc tggtggagtc cggcggcgga ctggtgcagc ctggaggatc cctgcggctg     60
tcctgcgctg ctagcggcag catcttcaac atccccgtga tgggctggta caggcaggct    120
cccggcaagc agcgggagct ggtggctgga atcagcaccg gcggcaccac caactatggc    180
gacagcgtga aggcaggtt caccatcagc aggataacg ctaagaatac cgtgtacctg    240
cagatgaaca gcctgaagcc tgaggatacc gccgtgtact attgcaatgt gctggtggtg    300
agcggcatcg gcagcaccct ggaggtgtgg ggccagggaa ccctggtgac agtgagctcc    360

<210> SEQ ID NO 65
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (6)..(6)
<223> OTHER INFORMATION: Xaa is T or S

<400> SEQUENCE: 65

Ile Ser Arg Gly Gly Xaa Thr
1               5

<210> SEQ ID NO 66
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is P or V
<220> FEATURE:
<221> NAME/KEY: MISC_FEATURE
<222> LOCATION: (10)..(10)
<223> OTHER INFORMATION: Xaa is F or I

<400> SEQUENCE: 66

Asn Ala Gln Ala Trp Asp Xaa Gly Thr Xaa Arg Tyr Leu Glu Val
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is I or M

<400> SEQUENCE: 67

Xaa Ser Thr Gly Gly Thr Thr
1               5

<210> SEQ ID NO 68
<211> LENGTH: 14
<212> TYPE: PRT
<213> ORGANISM: Artificial Sequence
<220> FEATURE:
<223> OTHER INFORMATION: Synthesized peptide -continued

```
<220> FEATURE:
<221> NAME/KEY: MISC_FEATURE
<222> LOCATION: (5)..(5)
<223> OTHER INFORMATION: Xaa is I or V
<220> FEATURE:
<221> NAME/KEY: MISC_FEATURE
<222> LOCATION: (11)..(11)
<223> OTHER INFORMATION: Xaa is H or T

<400> SEQUENCE: 68

Asn Val Leu Val Xaa Ser Gly Ile Gly Ser Xaa Leu Glu Val
1               5                   10
```

CLDN18.2 BINDING MOLECULE

CROSS-REFERENCE TO RELATED APPLICATIONS

This application is a U.S. national stage application, filed under 35 U.S.C. § 371(c), based on International Patent Application No. PCT/CN2020/091441, filed on May 21, 2020, which claims priority to Chinese Patent Application No. 201910437800.2, filed on May 24, 2019 and Chinese Patent Application No. 201910437806.X, filed on May 24, 2019, the entire contents of each of which are incorporated herein by reference.

SEQUENCE LISTING

The present application contains a Sequence Listing which has been submitted electronically in ASCII format, which is incorporated herein by reference in its entirety. Said ASCII copy, created Aug. 6, 2025, is named 134361-00402_SL.txt and is 50,221 bytes in size.

TECHNICAL FIELD

In general, the present application relates to antibodies. In particular, the present application relates to a single domain antibody that specifically recognizes CLDN18.2, a method for preparing same and use thereof.

BACKGROUND ART

Cell junctions are structures connecting cells and are an important basis for the inter-association and interaction between adjacent cells in a multicellular organism. In general, there are four types of animal cell junctions: tight junctions, adherens junctions, gap junctions, and desmosomes/hemidesmosomes.

Tight junctions, also referred to as occluding junctions, are structures forming between endothelial or epithelial cells and can prevent substances between tissues from diffusing through the intercellular spaces; hence the substances are allowed to enter the cells only through active transport. Structures of tight junction form through the intracellular and intercellular protein interactions among dozens of Claudin proteins, and the expression of these proteins has a certain tissue specificity. CLDN18 is an important one among the Claudin proteins present in tight junctions.

CLDN18 is a membrane protein with four transmembrane regions and contains two extracellular domains. There are two CLDN18 variants in the human body, named CLDN18.1 and CLDN18.2, respectively. These two proteins are distributed in different tissues. CLDN18.1 is mainly expressed in pulmonary epithelial cells, and CLDN18.2 is specifically expressed in gastric epithelial cells and is not expressed in gastric stem cells. The protein sequences of CLDN18.1 and CLDN18.2 have an extremely high similarity, and the main difference between them is in the N-terminus, in which part there is a difference of merely 8 amino acids in the first extracellular domains; and except for the N-terminus, the C-terminal sequences are completely identical.

Antibody therapy is becoming one of the most promising methods for treating cancer in patients. At present, due to the expression specificity in tumor cells and normal tissues, CLDN18.2 has become a very potential target for antibody drug development. However, due to the extremely high sequence similarity between CLDN18.1 and CLDN18.2, it is extremely difficult to develop antibodies that specifically target CLDN18.2 but not CLDN18.1, and there is very few report worldwide in this area. Up to now, IMAB362, developed by Ganymed AG from Germany, is the only antibody undergoing clinical studies that targets CLDN18.2. IMAB362 is a monoclonal antibody consisting of two heavy chains and two light chains. At present, single domain antibody that specifically targets CLDN18.2 has not been reported yet.

Single domain antibody (referred to as sdAb for short) is an antibody consisting of a single monomeric variable antibody domain (e.g., a variable domain of heavy chain). Like an intact antibody (e.g., IgG), a single domain antibody alone can selectively bind to a specific antigen. However, the molecular weight of a single domain antibody is much smaller than that of a common antibody that consists of two heavy chains and two light chains. The first single domain antibody is engineered from heavy chain antibody found in a camelid (Hamers-Casterman C, Atarhouch T, Muyldermans S, Robinson G, Hamers C, Songa E B, Bendahman N, Hamers R (1993) Naturally Occurring Antibodies Devoid of Light Chains. Nature 363 (6428): 446-448); and the heavy chain antibody found in these camelids is also referred to as a VHH antibody. At present, most of the research on single domain antibody is based on heavy chain variable domains.

Single domain antibodies possess many advantages. For example, they generally exhibit quite high solubility, good thermal stability and tissue penetration. Due to the presence of intramolecular disulfide bond, single domain antibodies could also be resistant to the degradation by papains etc. In addition, single domain antibodies can be expressed, in a quite high expression amount and in many host cells such as yeast, plant and mammalian cells, which endows them with very great cost advantages. The advantages of single domain antibodies make them applicable to various biological techniques and therapeutic applications. For example, single domain antibodies can be used to treat diseases, including but not limited to cancer, infectious diseases, inflammatory diseases, and neurodegenerative diseases.

Although there is already a monoclonal antibody drug undergoing clinical studies currently that targets the CLDN18.2 target, an urgent need still exists to continue with the development of antibodies that target the CLDN18.2 target as therapeutic agents. It is desirable in the art to develop a new antibody that targets CLDN18.2, particularly a single domain antibody that only specifically recognizes CLDN18.2 but does not recognize CLDN18.1.

SUMMARY OF THE INVENTION

Broadly speaking, the present disclosure provides a novel compound of an antibody, a preparation method, a composition and a product thereof. The benefits provided by the present disclosure are widely applicable to the fields of treatment and diagnosis with antibodies. More particularly, the present disclosure provides a single domain antibody that targets CLDN18.2, a method for preparing the antibody, an expression vector and a host cell for expressing the antibody, etc. The antibody of the present disclosure provides a method for treating or preventing a condition associated with Claudin proteins, particularly CLDN18.2 and use thereof.

The inventors first discovered a CLDN18.2 binding molecule that can specifically bind to the extracellular domain 1 (ECD1) of human CLDN18.2 (e.g., a single domain antibody that targets CLDN18.2).

The present disclosure at least comprises the following embodiments, which are arranged sequentially and enumerated in the manner of "N", respectively (wherein "N" represents a number). The following enumerative list is not exhaustive, and those skilled in the art can combine different technical solutions.

1. A CLDN18.2 binding molecule, comprising at least one immunoglobulin single variable domain, wherein the immunoglobulin single variable domain comprises CDR1, CDR2 and CDR3 selected from any one of the following groups:

(a) CDR1 comprising an amino acid sequence at least 80%, 85%, 90%, or 95% identical to SEQ ID NO: 1, CDR2 comprising an amino acid sequence at least 80%, 85%, 90%, or 95% identical to SEQ ID NO: 2, and CDR3 comprising an amino acid sequence at least 80%, 85%, 90%, or 95% identical to SEQ ID NO: 3; and (b) CDR1 comprising an amino acid sequence at least 80%, 85%, 90%, or 95% identical to SEQ ID NO: 30, CDR2 comprising an amino acid sequence at least 80%, 85%, 90%, or 95% identical to SEQ ID NO: 31, and CDR3 comprising an amino acid sequence at least 80%, 85%, 90%, or 95% identical to SEQ ID NO: 32.

2. The CLDN18.2 binding molecule of embodiment 1, wherein:

(a) the amino acid sequence of CDR1 differs from SEQ ID NO: 1 by amino acid addition, deletion or substitution of not more than 2 amino acids, the amino acid sequence of CDR2 differs from SEQ ID NO: 2 by amino acid addition, deletion or substitution of not more than 2 amino acids, and the amino acid sequence of CDR3 differs from SEQ ID NO: 3 by amino acid addition, deletion or substitution of not more than 2 amino acids; or (b) the amino acid sequence of CDR1 differs from SEQ ID NO: 30 by amino acid addition, deletion or substitution of not more than 2 amino acids, the amino acid sequence of CDR2 differs from SEQ ID NO: 31 by amino acid addition, deletion or substitution of not more than 2 amino acids, and the amino acid sequence of CDR3 differs from SEQ ID NO: 32 by amino acid addition, deletion or substitution of not more than 2 amino acids.

3. The CLDN18.2 binding molecule of embodiment 1, wherein:

(a) the amino acid sequence of CDR1 differs from SEQ ID NO: 1 by amino acid addition, deletion or substitution of 1 amino acid, the amino acid sequence of CDR2 differs from SEQ ID NO: 2 by amino acid addition, deletion or substitution of 1 amino acid, and the amino acid sequence of CDR3 differs from SEQ ID NO: 3 by amino acid addition, deletion or substitution of 1 amino acid; or (b) the amino acid sequence of CDR1 differs from SEQ ID NO: 30 by amino acid addition, deletion or substitution of 1 amino acid, the amino acid sequence of CDR2 differs from SEQ ID NO: 31 by amino acid addition, deletion or substitution of 1 amino acid, and the amino acid sequence of CDR3 differs from SEQ ID NO: 32 by amino acid addition, deletion or substitution of 1 amino acid.

4. The CLDN18.2 binding molecule of any one of the preceding embodiments, wherein the CLDN18.2 binding molecule is an antibody or an antigen binding fragment thereof against CLDN18.2.

5. The CLDN18.2 binding molecule of any one of the preceding embodiments, wherein the immunoglobulin single variable domain is VHH; for example, a VHH from a camelid (e.g., an alpaca).

6. The CLDN 18.2 binding molecule of any one of the preceding embodiments, wherein the immunoglobulin single variable domain comprises CDR1, CDR2 and CDR3 selected from any one of the following groups:

(a) CDR1 having the amino acid sequence as shown in SEQ ID NO: 1, CDR2 having the amino acid sequence as shown in formula ISRGGXIT (SEQ ID NO: 65), wherein $X_1$ is T or S, and CDR3 having the amino acid sequence as shown in formula NAQAWDX$_2$GTX$_3$RYLEV (SEQ ID NO: 66), wherein $X_2$ is P or V and $X_3$ is F or I; and (b) CDR 1 having the amino acid sequence as shown in SEQ ID NOs: 30, 33, 34, 35, 36, 38, 39, or 40, CDR2 having the amino acid sequence as shown in formula $X_4$STGGTT (SEQ ID NO: 67), wherein $X_4$ is I or M, and CDR3 having the amino acid sequence as shown in formula NVLVX$_5$SGIGSX$_6$LEV (SEQ ID NO: 68), wherein $X_5$ is I or V and $X_6$ is H or T.

7. The CLDN18.2 binding molecule of any one of the preceding embodiments, wherein the immunoglobulin single variable domain comprises:

(a) CDR1 having the amino acid sequence as shown in SEQ ID NO: 1, CDR2 having the amino acid sequence as shown in SEQ ID NO: 2, and CDR3 having the amino acid sequence as shown in SEQ ID NO: 3;

(b) CDR1 having the amino acid sequence as shown in SEQ ID NO: 1, CDR2 having the amino acid sequence as shown in SEQ ID NO: 4, and CDR3 having the amino acid sequence as shown in SEQ ID NO: 5; or (c) CDR1 having the amino acid sequence as shown in SEQ ID NO: 1, CDR2 having the amino acid sequence as shown in SEQ ID NO: 2, and CDR3 having the amino acid sequence as shown in SEQ ID NO: 6;

(d) CDR1 having the amino acid sequence as shown in SEQ ID NO: 30, CDR2 having the amino acid sequence as shown in SEQ ID NO: 31, and CDR3 having the amino acid sequence as shown in SEQ ID NO: 32;

(e) CDR1 having the amino acid sequence as shown in SEQ ID NO: 30, CDR2 having the amino acid sequence as shown in SEQ ID NO: 31, and CDR3 having the amino acid sequence as shown in SEQ ID NO: 37;

(f) CDR1 having the amino acid sequence as shown in SEQ ID NO: 33, CDR2 having the amino acid sequence as shown in SEQ ID NO: 31, and CDR3 having the amino acid sequence as shown in SEQ ID NO: 62;

(g) CDR1 having the amino acid sequence as shown in SEQ ID NO: 33, CDR2 having the amino acid sequence as shown in SEQ ID NO: 31, and CDR3 having the amino acid sequence as shown in SEQ ID NO: 37;

(h) CDR1 having the amino acid sequence as shown in SEQ ID NO: 34, CDR2 having the amino acid sequence as shown in SEQ ID NO: 31, and CDR3 having the amino acid sequence as shown in SEQ ID NO: 37;

(i) CDR1 having the amino acid sequence as shown in SEQ ID NO: 35, CDR2 having the amino acid sequence as shown in SEQ ID NO: 31, and CDR3 having the amino acid sequence as shown in SEQ ID NO: 62;

(j) CDR1 having the amino acid sequence as shown in SEQ ID NO: 36, CDR2 having the amino acid sequence as shown in SEQ ID NO: 31, and CDR3 having the amino acid sequence as shown in SEQ ID NO: 62;

(k) CDR1 having the amino acid sequence as shown in SEQ ID NO: 38, CDR2 having the amino acid sequence as shown in SEQ ID NO: 31, and CDR3 having the amino acid sequence as shown in SEQ ID NO: 62;

(l) CDR1 having the amino acid sequence as shown in SEQ ID NO: 39, CDR2 having the amino acid sequence as shown in SEQ ID NO: 41, and CDR3 having the amino acid sequence as shown in SEQ ID NO: 37; or (m) CDR1 having the amino acid sequence as shown in SEQ ID NO: 40, CDR2 having the amino acid sequence as shown in SEQ ID NO: 31, and CDR3 having the amino acid sequence as shown in SEQ ID NO: 37.

8. The CLDN18.2 binding molecule of any one of the preceding embodiments, wherein the immunoglobulin single variable domain comprises any one selected from the following groups:

(a) the amino acid sequence of SEQ ID NO: 7, an amino acid sequence at least 80%, 85%, 90%, or 95% identical to SEQ ID NO: 7, or an amino acid sequence having addition, deletion and/or substitution of one or more (e.g., 1, 2, 3, 4, 5, 6, 7, 8, 9, or 10) amino acids compared to SEQ ID NO: 7;

(b) the amino acid sequence shown in SEQ ID NO: 47, an amino acid sequence at least 80%, 85%, 90%, or 95% identical to SEQ ID NO: 47, or an amino acid sequence having addition, deletion and/or substitution of one or more (e.g., 1, 2, 3, 4, 5, 6, 7, 8, 9, or 10) amino acids compared to SEQ ID NO: 47.

9. The CLDN18.2 binding molecule of any one of the preceding embodiments, wherein the immunoglobulin single variable domain:

(a) has modification(s) (e.g., substitution of amino acid(s)) at one or more of the following positions in SEQ ID NO: 7: the amino acid at position 1, 4, 5, 14, 16, 35, 47, 56, 58, 65, 92, 102, 105, or 121; or (b) has modification(s) (e.g., substitution and/or addition of amino acid(s)) at one or more of the following positions in SEQ ID NO: 47: the amino acid at position 1, 4, 5, 11, 27, 28, 29, 30, 31, 32, 35, 51, 75, 76, 92, 100, 106, or 120.

10. The CLDN18.2 binding molecule of any one of the preceding embodiments, wherein the immunoglobulin single variable domain comprises, or consists of the following any one of SEQ ID NOs: sequences: 7, 8, 9, 10, 11, 12, 13, 14, 42, 43, 44, 45, 46, 47, 48, 49, 50, 51 and 63.

11. The CLDN18.2 binding molecule of any one of the preceding embodiments, wherein the CLDN18.2 binding molecule is a single domain antibody, such as a heavy chain single domain antibody; a chimeric antibody; or a humanized antibody.

12. The CLDN18.2 binding molecule of any one of the preceding embodiments, wherein the immunoglobulin single variable domain is fused to an additional molecule, and the additional molecule is for example, an Fc domain of an immunoglobulin (e.g., IgG) or a fluorescent protein.

13. The CLDN18.2 binding molecule of embodiment 12, wherein the CLDN18.2 binding molecule is a chimeric antibody comprising a VHH from camelid and an Fc domain of human IgG (e.g., human IgG1 or IgG4).

14. The CLDN18.2 binding molecule of embodiment 13, wherein the CLDN18.2 binding molecule is a chimeric antibody comprising a VHH from alpaca and an Fc domain of human IgG1.

15. The CLDN18.2 binding molecule of any one of the preceding embodiments, wherein the CLDN18.2 binding molecule binds to the extracellular domain 1 (ECD1) of human CLDN18.2.

16. A CLDN18.2 binding molecule, competing with the CLDN18.2 binding molecule of any one of the preceding embodiments for the same epitope.

17. The CLDN18.2 binding molecule of any one of the preceding embodiments, specifically binding to CLDN18.2 but not binding to CLDN18.1.

18. An isolated nucleic acid molecule, comprising a nucleic acid sequence encoding the CLDN18.2 binding molecule as defined in any one of the preceding embodiments.

19. The isolated nucleic acid molecule of embodiment 18, comprising, or consisting of the following sequences: any one of SEQ ID NOs: 22, 23, 24, 25, 26, 27, 28, 29, 52, 53, 54, 55, 56, 57, 58, 59, 60, 61 and 64.

20. An expression vector, comprising the isolated nucleic acid molecule of embodiment 18 or 19.

21. A host cell, comprising the expression vector of embodiment 20.

22. The host cell of embodiment 21, wherein the host cell is a bacterial cell (e.g., *Escherichia coli* (*E. coli*)), a fungal cell (e.g., a yeast), or a mammalian cell.

23. A pharmaceutical composition, comprising at least one CLDN18.2 binding molecule as defined in any one of embodiments 1-17 and a pharmaceutically acceptable carrier.

24. A method for preparing the CLDN18.2 binding molecule as defined in any one of embodiments 1-17, comprising the steps of:

expressing the CLDN18.2 binding molecule as defined in any one of embodiments 1-17 in the host cell of embodiment 21 or 22; and isolating the CLDN18.2 binding molecule from the host cell.

25. A method for treating a condition associated with CLDN18.2 in a subject, comprising: administering a therapeutically effective amount of the CLDN18.2 binding molecule as defined in any one of embodiments 1-17 to the subject.

26. The method of embodiment 25, wherein the condition associated with CLDN18.2 includes a disease related to the cell expressing CLDN18.2 or a disease associated with the cell expressing CLDN18.2.

27. The method of embodiment 25 or 26, wherein the condition associated with CLDN18.2 includes a cancer.

28. The method of embodiment 27, wherein the cancer includes bone cancer, blood cancer, lung cancer, hepatic cancer, pancreatic cancer, skin cancer, head-neck cancer, cutaneous or intraocular melanoma, uterine cancer, ovarian cancer, rectal cancer, cancer of the anal region, gastric cancer, colon cancer, breast cancer, prostate cancer, cancers of sexual organs and reproductive organs, Hodgkin's disease, esophageal cancer, small intestine cancer, cancers of endocrine system, thyroid cancer, parathyroid carcinoma, adrenal cancer, soft tissue sarcomas, bladder cancer, renal cancer, renal cell carcinoma, renal pelvis cancer, central nervous system (CNS) tumor, neuroectodermal cancer, spinal axis tumor, glioma, meningioma, and pituitary adenoma.

29. The method of embodiment 28, wherein the cancer is gastric cancer.

30. Use of the CLDN18.2 binding molecule as defined in any one of embodiments 1-17 in the preparation of a medicament for treating or preventing a condition associated with CLDN18.2.

31. A kit for treating or diagnosing a condition associated with CLDN18.2, comprising a container, the container comprises the CLDN18.2 binding molecule as defined in any one of embodiments 1-17.

The content stated above is a general description, and may include simplification, summary and omission of details if necessary. Therefore, those skilled in the art will recognize that the general description is only for illustrative purposes and not intended to be limiting in any way. Other aspects, features and advantages of the method, composition and/or device and/or other subjects described herein will become apparent from the teaching set forth herein. General descriptions are provided to briefly introduce some selected concepts, and these general descriptions will be further described in the following detailed description. The general descriptions above are not intended to determine the key features or basic features of the claimed subject matter, nor are they intended to be used as an auxiliary means to determine the scope of the claimed subject matter. In addition, the content of all references, patents, and published patent applications cited throughout the present application is incorporated herein by reference in their entirety.

BRIEF DESCRIPTION OF THE DRAWINGS

FIG. 1a shows the flow cytometry identification results of the human CLDN18.2-HEK293T, human CLDN18.1-HEK293, mouse CLDN18.2-HEK293, and mouse CLDN18.1-HEK293 cell line; and FIG. 1b shows the flow cytometry identification results of the human CLDN18.2-KATOIII tumor cell line.

FIG. 4a shows the experimental results of the antibody NA1-S and control antibody binding on human CLDN18.2-HEK293T cells by flow cytometry method; and FIG. 4b shows the experimental results of the antibody NA1-S and control antibody binding on human CLDN18.2-KATOIII tumor cell by flow cytometry method.

FIGS. 5a-5c show the experimental results of the binding comparison among the candidate antibodies NA3-S, NA5-S, NA6-S, and control antibody at the cellular level, wherein FIG. 5a shows the experimental results of the antibodies NA3-S and NA6-S binding on human CLDN18.2-HEK293T cells by flow cytometry method; FIG. 5b shows the experimental results of the antibody NA5-S binding on human CLDN18.2-HEK293T cells by flow cytometry method; and FIG. 5c shows the experimental results of the antibodies NA3-S, NA5-S, and NA6-S and control antibody binding on human CLDN18.2-KATOIII tumor cell by flow cytometry method.

FIGS. 6a and 6b show the complement dependent cytotoxicity (CDC) mediated by the candidate antibody NA1-S on human CLDN18.2-HEK293T cell and human CLDN18.2-KATOIII tumor cell, wherein FIG. 6a shows the CDC mediated by the antibody NA1-S on human CLDN18.2-HEK293T; and FIG. 6b shows the CDC mediated by the antibody NA1-S on human CLDN18.2-KATOIII tumor cell.

FIGS. 7a-7d show the complement dependent cytotoxicity (CDC) mediated by the candidate antibodies NA3-S, NA5-S and NA6-S on human CLDN18.2-HEK293T cell and human CLDN18.2-KATOIII tumor cell, wherein FIG. 7a shows the CDC cytotoxicity mediated by the antibody NA3-S on human CLDN18.2-HEK293T; FIGS. 7b and 7c show the CDC killing effect of NA5-S and NA6-S on human CLDN18.2-HEK293T cells, respectively; and FIG. 7d shows the CDC mediated by the antibody NA3-S on human CLDN18.2-KATOIII tumor cell.

FIGS. 8a-8d show the antibody-dependent cell cytotoxicity (ADCC) mediated by the candidate antibodies NA1-S and NA3-S on human CLDN18.2-HEK293T and human CLDN18.2-KATOIII tumor cell, wherein FIGS. 8a and 8c show the ADCC mediated by the antibodies NA1-S and NA3-S on human CLDN18.2-HEK293T cell; and FIGS. 8b and 8d show the ADCC mediated by the antibodies NA1-S and NA3-S on human CLDN18.2-KATOIII tumor cell.

FIGS. 10a-10i show the binding of candidate antibodies NA1-S, NA3-S, and IMAB362 on the epitopes of CLDN18.2 and the amino acid positions critical for the binding, wherein FIGS. 10a-10b show the competitive binding assays of candidate antibodies NA1-S (FIG. 10a) or NA3-S (FIG. 10b) with IMAB362 on human CLDN18.2-HEK293T; and FIGS. 10c-10d show the competitive binding assays of antibody IMAB362 with NA1-S (FIG. 10c) or NA3-S (FIG. 10d) on human CLDN18.2-HEK293T. FIG. 10e shows the expression level of the mutant or wild-type CLDN18.2 on human CLDN18.2-HEK293T cell lines determined with an anti-CLDN18 antibody; FIGS. 10f-10g show the binding ability of NA1-S (FIG. 10f), NA3-S (FIG. 10g) and IMAB362 to the CLDN18.2 mutants on human CLDN18.2 mutant cell lines; and FIGS. 10h-10i show the relative binding percentage of NA1-S (FIG. 10h), NA3-S (FIG. 10i) and IMAB362 on human CLDN18.2 mutant cell lines relative to the wide-type CLDN18.2 cell line.

9
10

Figure 12:
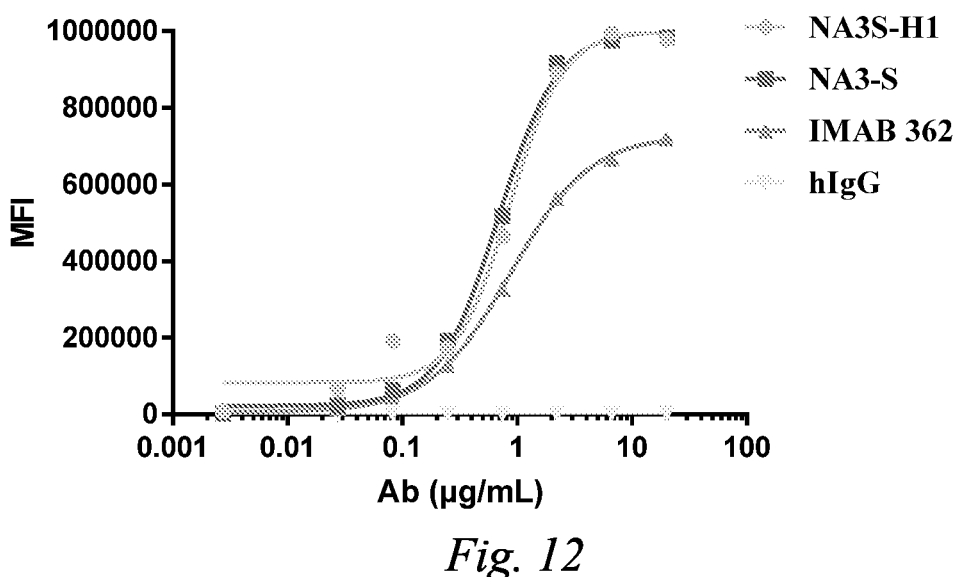

FIG. 12 shows the binding activity of NA3-S on CLDN18.2-HEK293T cells before and after humanization of the sequence, wherein NA3S-H1 is a humanized molecule.

Figure 13A:
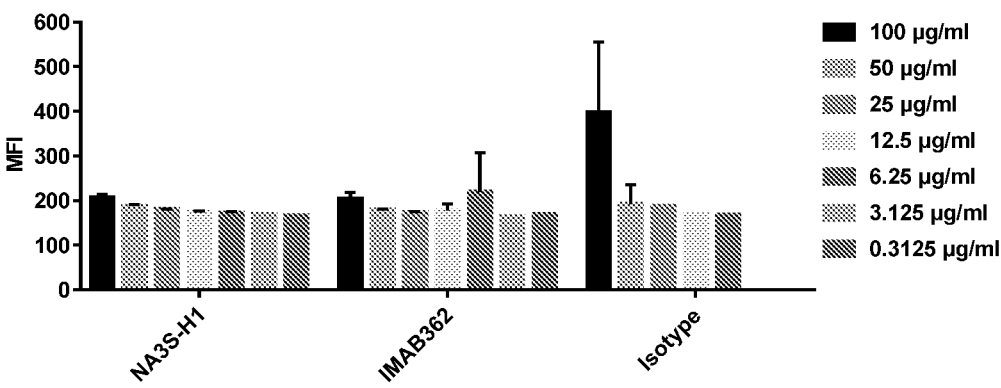
Figure 13B:
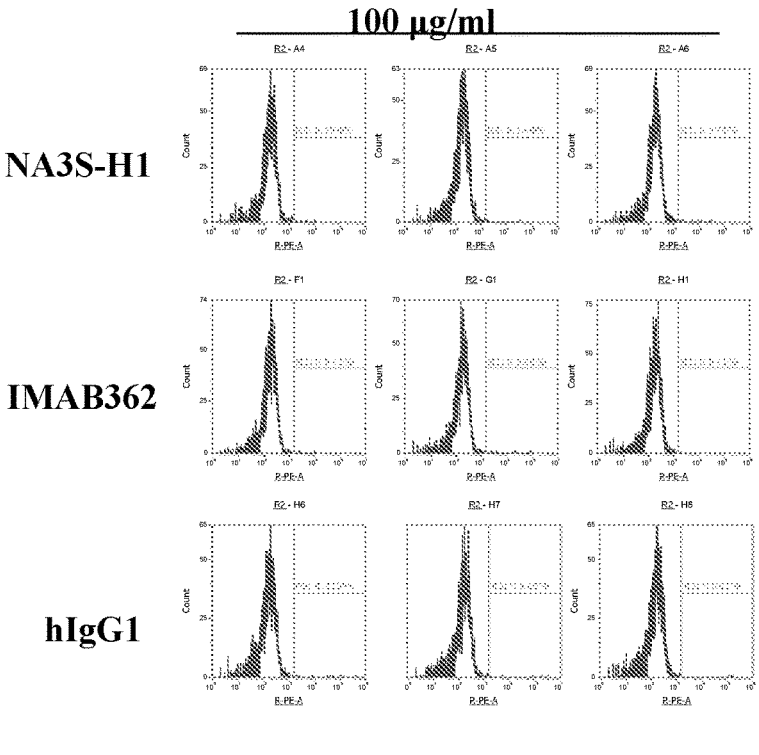

FIG. 13 compares the antibody-binding intensity and antibody-binding positive rate of NA3S-H1 and IMAB362 on CLDN18.1-HEK293T cells at high concentrations, wherein, FIG. 13a shows the binding intensity of different concentrations of NA3S-H1 and IMAB362 on CLDN18.1-HEK293T cells, and FIG. 13b shows the binding positive rate of a high concentration (100 μg/ml) of NA3S-H1 and IMAB362 on CLDN18.1-HEK293T cells and isotype antibodies are used as the control in the tests.

Figure 14:
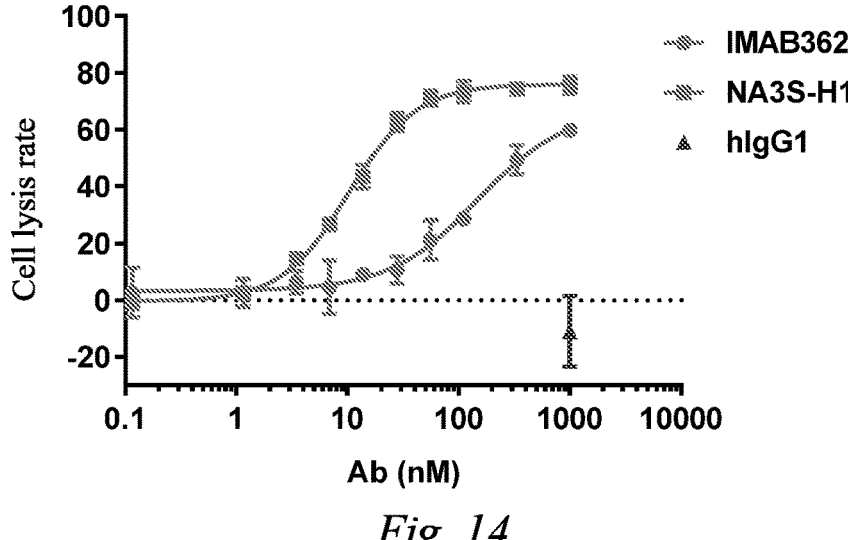

FIG. 14 shows the CDC cell killing efficiency of the humanized molecule NA3S-H1 on human CLDN18.2-KA-TOIII gastric cancer cells, wherein the control antibody is IMAB362.

Figure 15A:
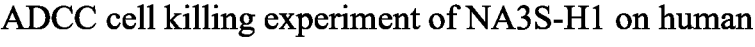
Figure 15A:
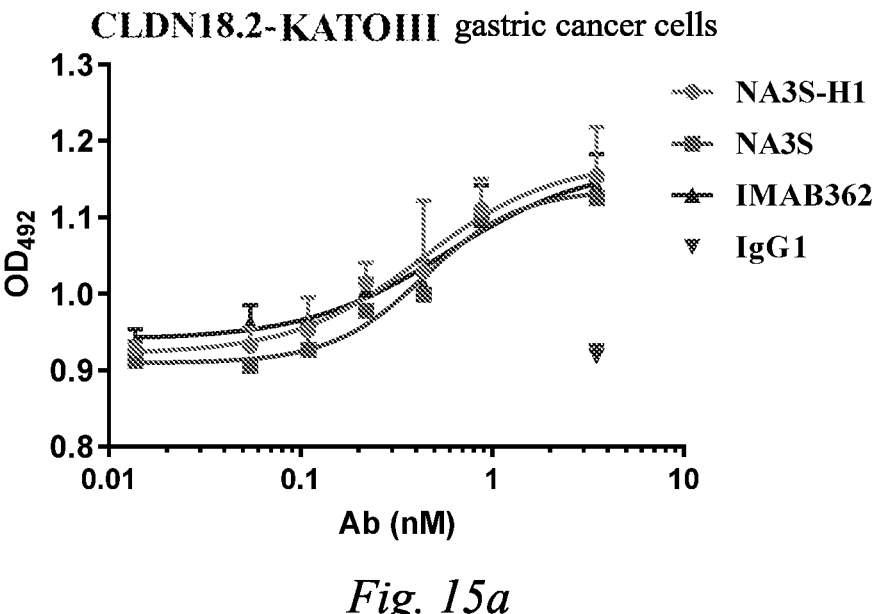
Figure 15B:
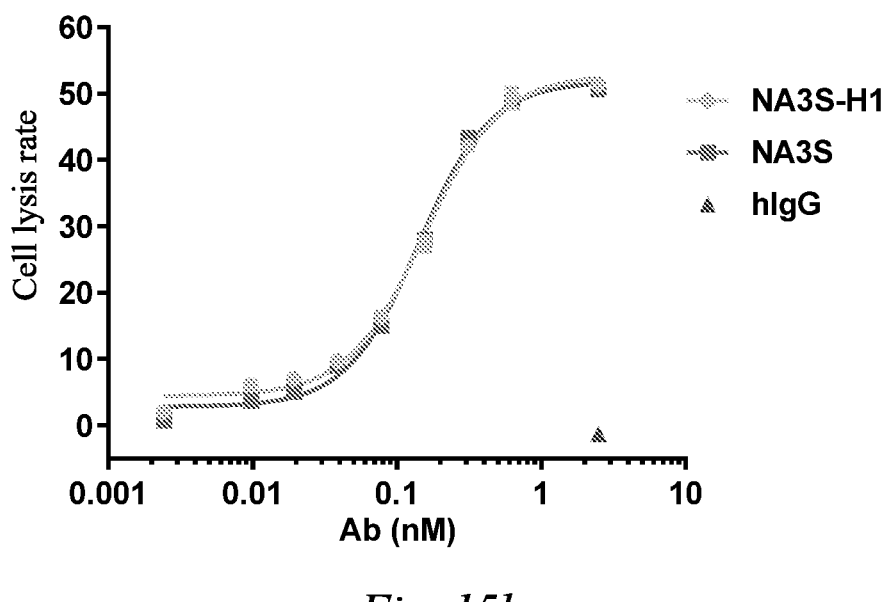

FIG. 15 shows the ADCC cell killing effect of NK cells mediated by NA3S-H1 and IMAB362 on different target cells. FIG. 15a shows the ADCC cell killing effect mediated by NA3S-H1 and IMAB362, with human CLDN18.2-KA-TOIII as the target cells; and FIG. 15b shows the ADCC cell killing effect mediated by NA3S-H1 and IMAB362, with human CLDN18.2-HEK293T as the target cells.

DETAILED DESCRIPTION OF EMBODIMENTS

Although the present invention can be practiced in many different forms, disclosed herein are specific illustrative embodiments that verify the principles of the present invention. It should be emphasized that the present invention is not limited to the detailed description of embodiments illustrated. In addition, any section headings used herein are only for organizational purposes and are not construed as limiting the subject matter described.

Unless defined otherwise herein, the scientific and technical terms used in conjunction with the present invention will have the meaning commonly understood by one of ordinary skill in the art. In addition, unless the context requires otherwise, terms in the singular form shall include the plural form, and terms in the plural form shall include the singular form. More specifically, as used in the present specification and in the appended claims, the singular forms "a", "an", and "the" include plural referents unless the context clearly dictates otherwise. Therefore, for example, reference to "a protein" includes multiple proteins; reference to "a cell" includes a mixture of cells, etc. In the present application, "or" as used means "and/or" unless stated otherwise. In addition, the use of the term "comprising" and other forms (such as "including" and "containing") is not limiting. In addition, ranges provided in the specification and the appended claims include both endpoints and all values between the endpoints.

Generally, the terms related to the cell and tissue culture, molecular biology, immunology, microbiology, genetics and protein, and nucleic acid chemistry and hybridization described herein and their techniques are well-known and frequently-used terms in the art. Unless stated otherwise, the methods and techniques of the present invention are generally carried out according to the conventional methods well-known in the art, and are carried out as described in various general and more specific references cited and discussed throughout the present specification. See for example, Abbas et al., Cellular and Molecular Immunology, 6th ed., W.B. Saunders Company (2010); Sambrook J. & Russell D. Molecular Cloning: A Laboratory Manual, 3rd ed., Cold Spring Harbor Laboratory Press, Cold Spring Harbor, N. Y. (2000); Ausubel et al., Short Protocols in Molecular Biology: A Compendium of Methods from Current Protocols in Molecular Biology, Wiley, John & Sons, Inc. (2002); Harlow and Lane, Using Antibodies: A Laboratory Manual, Cold Spring Harbor Laboratory Press, Cold Spring Harbor, N. Y. (1998); and Coligan et al., Short Protocols in Protein Science, Wiley, John & Sons, Inc. (2003). The terms related to analytical chemistry, synthetic organic chemistry and medicinal chemistry described herein as well as laboratory procedures and techniques are well-known and frequently-used terms in the art. In addition, any section headings used herein are only for organizational purposes and are not construed as limiting the subject matter described.

Definitions

To better understand the present invention, definitions and explanations of related terms are provided below.

As used herein, the term "antibody" or "Ab" generally refer to any form of an antibody that exhibits a desired biological or binding activity. The term includes but is not limited to a humanized antibody, a fully human antibody, a chimeric antibody, and a single domain antibody. An antibody can comprise a heavy chain and a light chain. Heavy chains can be divided into μ, δ, γ, α, and ε, which define the isotypes of an antibody as IgM, IgD, IgG, IgA, and IgE, respectively. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). VH regions and VL regions can be further divided into relatively conserved regions (referred to as framework regions (FRs)) and hypervariable regions (referred to as complementary determining regions (CDRs)) spaced apart by FRs. Each VH and VL consists of 3 CDRs and 4 FRs in the following order: from N-terminus to C-terminus, FR1, CDR1, FR2, CDR2, FR3, CDR3, and FR4. Distribution of amino acids in various regions or domains follows the definitions in: Kabat Sequences of Proteins of Immunological Interest (National Institutes of Health, Bethesda, Md. (1987 and 1991)) or Chothia & Lesk (1987) J. Mol. Biol. 196:901-917; and Chothia et al., (1989) Nature 342:878-883. An antibody may have different antibody isotypes, such as IgG (including, e.g., IgG1, IgG2, IgG3, or IgG4 subtypes), IgAQ1, IgA2, IgD, IgE, or IgM antibodies.

The term "humanized antibody" as used herein refers to an antibody in which a CDR sequence derived from the germline of another mammalian species such as a mouse has been grafted onto a human framework sequence. Additional framework region modifications can be made within the human framework sequence.

The term "chimeric antibody" as used herein refers broadly to an engineered antibody that contains one or more regions from an antibody and one or more regions from one or more other antibodies. Particularly, a chimeric antibody comprises a variable region derived from a non-human animal antibody and a constant region of another antibody, for example, a variable region of mouse origin and a constant region of human origin. A chimeric antibody can also refer to a multispecific antibody that have specificity for at least two different antigens.

The term "CLDN18.2 binding molecule" as used herein means a molecule that specifically binds to CLDN18.2.

The terms "CLDN18.2 antibody", "antibody against CLDN18.2", "antibody that specifically binds to CLDN18.2", "antibody that specifically targets CLDN18.2", and "antibody that specifically recognizes CLDN18.2" as used herein can be used interchangeably, and mean antibodies that can specifically bind to the Claudin protein CLDN18.2. Particularly, in a specific embodiment, the term means an antibody that specifically binds to human CLDN18.2, particularly an antibody that specifically binds to human CLDN18.2 but does not specifically bind to human CLDN18.1. The amino acid sequences of human CLDN18.2 and human CLDN18.1 are as shown in SEQ ID NO: 15 and SEQ ID NO: 16, respectively; the amino acid sequences of the mouse CLDN18.2 and mouse CLDN18.1 are as shown in SEQ ID NO: 17 and SEQ ID NO: 18, respectively.

The term "immunoglobulin single variable domain" or "ISV" as used herein is generally defined herein as such an amino acid sequence that: comprises an immunoglobulin fold or can form an immunoglobulin fold (i.e., by folding) under suitable conditions (e.g., under physiological conditions), i.e., thereby forming an immunoglobulin variable domain (e.g., a VH, VL or VHH domain); and forms (or can form under suitable conditions) an immunoglobulin variable domain comprising functional antigen binding sites (in the sense that no interaction with another immunoglobulin variable domain (e.g., VH-VL interactions) is required to form functional antigen binding sites).

The term "Ka" as used herein is intended to refer to the association rate for a particular antibody-antigen interaction, and the term "Kd" as used herein is intended to refer to the dissociation rate for a particular antibody-antigen interaction. The term "$K_D$" or "$K_D$ value", as used herein, is intended to refer to the dissociation constant for a particular antibody-antigen interaction, which is obtained from the ratio of Kd to Ka (i.e., Kd/Ka) and is expressed as a molar concentration (M). $K_D$ values for antibodies can be determined using methods well established in the art. A preferred method for determining the KD value of an antibody is by using surface plasmon resonance, preferably using a biosensor system such as a Biacore® system.

The term "specifically bind(s)" or "specifically bind(s) to" as used herein refers to the non-random binding reaction between two molecules such as between an antibody and an antigen.

As used herein, the ability to "inhibit the binding", "block the binding" or "compete for the same epitope" refers to the ability of an antibody to inhibit the binding of two molecules to any detectable extent. In some embodiments, an antibody that blocks the binding of two molecules inhibits the binding interaction between two molecules by at least 50%. In some embodiments, the inhibition can be greater than 60%, greater than 70%, greater than 80%, or greater than 90%.

As used herein, the term "high affinity" for an antibody refers to an antibody having a $K_D$ value of $1\times10^{-7}$ M or less, more preferably $5\times10^{-8}$ M or less, even more preferably $1\times10^{-8}$ M or less, even more preferably $5\times10^{-9}$ M or less, and even more preferably $1\times10^{-9}$ M or less for a target antigen.

As used herein, the term "$EC_{50}$", also referred to as "half maximal effective concentration", refers to the concentration of a medicament, antibody or toxic agent which induces a response at 50% between the baseline and the maximum after a specific exposure time. In the context of the present application, the unit of $EC_{50}$ is "nM". As used herein, the term "epitope" refers to the portion of an antigen to which an immunoglobulin or antibody specifically binds. "Epitope" is also referred to as "antigenic determinant". An epitope or an antigenic determinant generally consist of chemically active surface groups of molecules such as amino acids, carbohydrates or sugar side chains, and generally have specific three dimensional structural characteristics and specific charge characteristics. For example, an epitope generally comprises at least 3, 4, 5, 6, 7, 8, 9, 10, 11, 12, 13, 14, or 15 continuous or discontinuous amino acids in the unique three-dimensional configuration and can be a "linear epitope" or "conformational epitope". See for example, Epitope Mapping Protocols in Methods in Molecular Biology, vol. 66, G. E. Morris, Ed. (1996). In a linear epitope, all interaction sites between a protein and an interacting molecule (such as an antibody) are present linearly along the primary amino acid sequence of the protein. In a conformational epitope, the interaction sites span amino acid residues that are spaced apart from each other in the protein. Antibodies can be screened depending on the competition for binding to the same epitope detected by conventional techniques known to those skilled in the art. For example, competition or cross-competition studies can be carried out to obtain antibodies that compete with each other or cross-compete for binding to an antigen (e.g., CLDN18.2). A high-throughput method for obtaining antibodies that bind to the same epitope is described in the international patent application WO 03/048731, which is based on their cross-competition.

As used herein, the term "isolated" refers to a state of a substance or component obtained from its native state by artificial means. If certain "isolated" substance or component occurs naturally, it may be possible that its natural environment has changed, or the substance or component has been isolated from the natural environment, or both. For example, certain unisolated polynucleotide or polypeptide naturally occurs in some living animal, and the same high-purity polynucleotide or polypeptide isolated from the native state is referred to as an isolated polynucleotide or polypeptide. The term "isolated" neither excludes mixed man-made or synthetic substances, nor does it exclude other impure substances that do not affect the activity of the substance isolated.

As used herein, the term "isolated antibody" is intended to refer to an antibody that is substantially free of other antibodies having different antigenic specificities. In addition, an isolated antibody can be substantially free of other cellular materials and/or chemicals.

As used herein, the term "vector" refers to a nucleic acid vehicle into which a polynucleotide can be inserted. When the vector allows the expression of the protein encoded by the polynucleotide inserted therein, the vector is referred to as an expression vector. A vector can be transformed, transduced or transfected into a host cell so that the genetic substance elements carried by the vector are expressed in the host cell. The vector is well known to those skilled in the art, and includes but is not limited to: plasmids, cosmids, artificial chromosomes such as yeast artificial chromosomes (YAC), bacterial artificial chromosomes (BAC) or P1-derived artificial chromosomes (PAC), phages such as a λ phage or M13 phage, and animal viruses. The animal viruses that can be used as vectors include but are not limited to retroviruses (including lentiviruses), adenoviruses, adeno-associated viruses, herpes viruses (e.g., herpes simplex viruses), poxviruses, baculoviruses, papilloma viruses, and papovaviruses (e.g., SV40). The vector may contain multiple elements for controlling expression, and includes but is not limited to promoter sequences, transcription initiation sequences, enhancer sequences, selection elements, and reporter genes. Moreover, the vector may comprise an origin of replication.

As used herein, the term "host cell" refers to any kind of cell system into which a vector can be introduced, including but not limited to prokaryotic cells such as *Escherichia coli*

(*E. coli*) or *Bacillus subtilis*, fungal cells such as yeast cells or *Aspergillus*, insect cells such as *Drosophila* S2 cells or Sf9, and animal cells such as fibroblasts, CHO cells, COS cells, NSO cells, HeLa cells, BHK cells, HEK293 cells or human cells.

The method for producing the antibody of the present invention by using a host cell is conventional in the art and comprises expressing the antibody in prokaryotic or eukaryotic cells, then isolating the antibody, and generally purifying the antibody to a pharmaceutically acceptable purity. For example, in some embodiments, a nucleic acid encoding the antibody is inserted into an expression vector by standard techniques known in the art and the expression vector is introduced into suitable prokaryotic or eukaryotic host cells, the host cells such as CHO cells, NSO cells, SP2/0 cells, HEK293 cells, COS cells, PER.C6 (R) cells, yeast or *Escherichia coli* cells are cultured under conditions and for a period of time sufficient for the production of the antibody of the present invention or a functional fragment thereof, and the antibody is recovered from the cells (the supernatant or cells lysed), and the antibody is purified. Conventional methods for producing antibodies are known in the art, and are described in review articles, e.g., Makrides, S. C., Protein Expr. Purif. 17 (1999) 183-202; Geisse, S. et al., Protein Expr. Purif. 8 (1996) 271-282; Kaufman, R. J., Mol. Biotechnol. 16 (2000) 151-160; Werner, R. G., Drug Res. 48 (1998) 870-880.

As used herein, the term "identity" refers to a relationship between the sequences of two or more polypeptide molecules, or two or more nucleic acid molecules determined by sequence alignment and comparison. "Percent identity" refers to the percentage of identical residues between amino acids or nucleotides in the molecules being compared, and is calculated based on the size of the smallest molecule being compared. For these calculations, gaps (if any) in alignments are preferably addressed by a specific mathematical model or computer program (i.e., an "algorithm"). Methods that can be used to calculate the identity of the aligned nucleic acids or polypeptides include those described in: Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAMJ. Applied Math. 48:1073.

As used herein, the term "immunogenicity" refers to the ability to stimulate the formation of specific antibodies or sensitized lymphocytes in an organism. The term not only refers to the properties of antigens to stimulate specific immune cells to activate, proliferate and differentiate so as to ultimately produce immune effectors such as antibodies and sensitized lymphocytes, but also refers to that a specific immune response of the antibodies or sensitized T lymphocytes can develop in the immune system of an organism after the stimulation on the organism with antigens. Immunogenicity is the most important property of an antigen. Successful induction of immune response generation in a host by an antigen depends on three factors: the nature of the antigen, the reactivity of the host and the immunological means.

As used herein, the term "transfection" refers to the process of introducing a nucleic acid into eukaryotic cells, particularly mammalian cells. Protocols and techniques used for transfection include but are not limited to lipofection, transfection by chemical and physical methods such as electroporation. Many transfection techniques are well-known in the art, and see e.g., Graham et al., 1973, Virology 52: 456; Sambrook et al., 2001, Molecular Cloning: A Laboratory Manual; Davis et al., 1986, Basic Methods in Molecular Biology, Elsevier; Chu et al, 1981, Gene 13:197.

As used herein, the term "fluorescence-activated cell sorting" or "FACS" refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". 2017 Nov. 9). The instruments used to carry out FACS are known to those skilled in the art and are commercially available to the public. Examples of such instruments include FACS Star Plus, FACSean, and FACSort instruments from Becton Dickinson (Foster City, CA), Epics C from Coulter Epics Division (Hialeah, FL) and MoFlo from Cytomation (Colorado Springs, Colorado).

The term "subject" includes any human or non-human animal, preferably human.

As used herein, the term "condition associated with CLDN18.2" refers to any condition induced by or exacerbated by or otherwise associated with increased or reduced expression or activity of the CLDN18.2 (e.g., human CLDN18.2).

As used herein, the term "cancer" refers to solid tumors or nonsolid tumors (e.g., leukemia) mediated by any tumor or malignant cell growth, proliferation or metastasis that induces medical conditions.

The term "treatment" used herein in the context of the treatment of a pathogenetic condition generally refers to the treatment of and therapy for humans or animals, in which some desired therapeutic effects are effected, for example, the inhibition in the progression of the pathogenetic condition, including the decline in the rate of progression, the arrest in the rate of progression, the regression of the pathogenetic condition, the improvement of the pathogenetic condition, and the healing of the pathogenetic condition. The terms also include the treatment as preventative measures (i.e., prevention). For cancer, "treatment" may refer to inhibiting or slowing down the growth, proliferation or metastasis of tumors or malignant cells or some combination thereof. For tumors, "treatment" includes removing all or a part of the tumor, inhibiting or slowing down the growth and metastasis of the tumor, preventing or delaying the development of the tumor, or some combination thereof.

As used herein, the term "therapeutically effective amount" relates to the amount of an active compound or a material, composition or dosage form comprising the active compound, which is effective for producing some desired therapeutic effects commensurate with a reasonable benefit/risk ratio, when administered according to a desired treatment regimen. Particularly, "therapeutically effective amount" means the amount or concentration of an antibody or antigen binding portion thereof effective for treating a condition associated with CLDN18.2.

As used herein, the term "pharmaceutically acceptable" refers to that the carrier, diluent, excipient, and/or a salt thereof are/is chemically and/or physically compatible with other ingredients in the formulation, and are/is physiologically compatible with the recipient.

As used herein, the term "pharmaceutically acceptable carrier and/or excipient" refers to a carrier and/or excipient that are/is pharmacologically and/or physiologically compatible with the subject and the active agent and that are/is well-known in the art (see, e.g., Remington's Pharmaceutical Sciences. edited by Gennaro AR, 19th ed. Pennsylvania: Mack Publishing Company, 1995), and includes but is not limited to pH adjusting agents, surfactants, adjuvants, and ion strength enhancers. For example, the pH adjusting agents include but are not limited to phosphate buffer; the surfactants include but are not limited to cationic, anionic or nonionic surfactants, such as Tween-80; and the ion strength enhancers include but are not limited to sodium chloride.

As used herein, the term "adjuvant" refers to a non-specific immunoenhancer, which can enhance the immune response to an antigen or change the type of the immune response in an organism, when delivered into the organism with the antigen or delivered into the organism in advance. A wide variety of adjuvants exist in the prior art, and include but are not limited to aluminum adjuvants (e.g., aluminum hydroxide), Freund's adjuvants (e.g., Freund's Complete Adjuvant, and Freund's Incomplete adjuvant), *Corynebacteriuum parvm*, lipopolysaccharides, cytokines, etc. the Freund's adjuvants are currently the most commonly used adjuvants in animal experiments, the aluminium hydroxide adjuvants are more commonly used in clinical trials.

CLDN18.2 Binding Molecule

In some aspects, the present disclosure comprises a CLDN18.2 binding molecule.

In general, the CLDN18.2 binding molecule can comprise any molecule that specifically binds to CLDN18.2. In some cases, the "CLDN18.2 binding molecule" can comprise a "CLDN18.2 antagonist". The CLDN18.2 binding molecule or CLDN18.2 antagonist can be a polypeptide or protein, such as an antibody, more particularly an antibody that specifically binds to CLDN18.2 (e.g., human CLDN18.2).

The antibody includes but is not limited to a chimeric antibody, a humanized antibody, or a single domain antibody, etc. In specific embodiments, the CLDN18.2 binding molecule is a single domain antibody, which generally refers to an antibody consisting of a single monomeric variable antibody domain. Like an intact antibody, a single domain antibody can selectively bind to a specific antigen.

More particularly, the CLDN18.2 binding molecule is a heavy chain single domain antibody, which can be interchangeably used with the terms "VHH", "VHH antibody", "VHH domain", "VHH antibody fragment", "VIII" or "nanobody". The VHH molecule from a camelid antibody is one of the smallest known intact antigen binding domains (about 15 KDa, or 1/10 of a conventional IgG) and is therefore very suitable for delivery to the dense tissues and entry into the limited space among macromolecules.

The single domain antibody disclosed herein can be prepared by those skilled in the art according to methods known in the art or any future method. For example, the VHH can be obtained by methods known in the art, such as by immunizing a camel and obtaining the VHH that binds to and neutralizes a target antigen from the camel, or by generating a library of the VHH of the present invention by cloning using molecular biology techniques known in the art and then selecting by using phage display. In some embodiments, the single domain antibody of the present invention is naturally produced in a camelid animal, i.e., is produced by the camelid following immunization with CLDN18.2 or a fragment thereof, using techniques described herein for other antibodies.

In some embodiments, the single domain antibody is obtained by immunizing a llama or an alpaca with a desired antigen and subsequently isolating the mRNA encoding the heavy chain antibody. A gene library containing millions of single domain antibody clones is produced by reverse transcription and polymerase chain reaction. Screening techniques such as phage display and ribosome display facilitate the identification of clones that bind to antigens. Phage display includes synthesizing an antibody library on phages, screening the library with an antigen of interest or an antibody binding portion thereof, and isolating the antigen-binding phages, from which immunoreactive fragments can be obtained. Methods for preparing and screening such a library are well-known in the art, and kits for producing a phage display library are commercially available (e.g., Pharmacia recombinant phage antibody system, Cat. No. 27-9400-01; and Stratagene SurfZAP™ phage display kit, Cat. No. 240612). Other methods and reagents can also be used to generate and screen antibody display libraries (see e.g., Barbas et al., *Proc. Natl. Acad. Sci. USA* 88:7978-7982 (1991)).

When the most effective clone is identified, the DNA sequence thereof can be optimized by, for example, affinity maturation or humanization to prevent the immune response against antibodies in the human body.

Therefore, the single domain antibody of the present invention can be obtained by: (1) isolating a naturally occurring VHH domain of a heavy chain antibody; (2) expressing the nucleotide sequence that encodes a naturally occurring VHH domain; (3) "humanizing" a naturally occurring VHH domain or expressing the nucleic acid that encodes such a humanized VHH domain; (4) "camelising" a naturally occurring VH domain from any animal species, particularly a mammalian species, such as, from human, or expressing the nucleic acid that encodes such a camelised VH domain; (5) "camelising" a "domain antibody" or "dAb" (see e.g., Ward et al., 1989, Nature 341:544-546), or expressing the nucleic acid that encodes such a camelised VH domain; (6) preparing a protein, polypeptide or other amino acid sequence by using synthetic or semisynthetic techniques; (7) preparing the nucleic acid encoding the VHH by using techniques for synthesizing nucleic acids and then expressing the nucleic acid thus obtained; and/or (8) a combination of any of the foregoing. Based on the disclosure herein, suitable methods and techniques for performing the foregoing content will be clear to those skilled in the art, and include, for example, the methods and techniques described in more detail below.

Single domain antibodies are generally produced by PCR cloning a variable domain library from cDNA of blood, lymph nodes or splenic lymphocytes obtained from immunized animals into a phage display vector. Antigen-specific single domain antibodies are generally selected by panning the corresponding library on the immobilized antigen (such as the antigen coated on the plastic surface of a test tube, the biotinylated antigen immobilized on the streptavidin beads, or the membrane protein expressed on the cell surface). Affinity of sdAbs can be improved by in vitro simulation of the strategies, such as by site-directed mutagenesis in CDR regions and by further panning the immobilized antigens under increased stringency conditions (higher temperature, high or low salt concentrations, high or low pH and low antigen concentrations) (Wesolowski et al., Single Domain Antibodies: Promising Experimental and Therapeutic Tools in Infection and Immunity. Med Microbiol Immunol (2009) 198:157-174).

Methods for preparing a VHH that specifically binds to an antigen or epitope are described in references, and see e.g., R. van der Linden et al., Journal of Immunological Methods, 240 (2000) 185-195; Li et al., J Biol Chem., 287 (2012)

13713-13721; Deffar et al., African Journal of Biotechnology, vol. 8 (12), pp. 2645, 17 Jun. 2009 and WO 94/04678.

In some embodiments, the VHH in the CLDN18.2 binding molecule is fused with the Fc domain (such as, the Fc domain of IgG (e.g., IgG1 or IgG4)) of an antibody. Effector functions such as ADCC and CDC can be more effectively recruited by fusing VHH to the Fc domain. Moreover, the fusion of VHH and the Fc domain can help the CLDN18.2 binding molecules form dimers, and can also help prolong the in vivo half-life of the CLDN18.2 binding molecules.

As used herein, the term "antibody-dependent cell-mediated cytotoxicity" or "ADCC" refers to a cytotoxic form through which a secreted antibody that binds to an Fc receptor (FcR) present on some cytotoxic effector cells (e.g., natural killer (NK) cells, neutrophil, and macrophages) enables these cytotoxic effector cells to specifically bind to target cells carrying antigens and subsequently kill the target cells with cytotoxins. The fact that antibodies "arm" cytotoxic cells is absolutely necessary for this killing. NK cells, the primary cells for mediating ADCC, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS (USA) 95:652-656 (1998).

The term "complement dependent cytotoxicity" or "CDC" refers to the lysis of a target cell in the presence of a complement. Activation of the classical complement pathway is initiated by the binding of the first component of the complement system (C1q) to (the appropriate subclass of) antibodies which are bound to their cognate antigen. To assess complement activation, a CDC assay, e.g., the method as described in Gazzano-Santoro et al., J. Immunol. Methods 202:163 (1996), may be performed.

For the ease of description, the CLDN18.2 binding molecule is described hereinafter as the CLDN18.2 antibody.

CLDN18.2 Antibody Capable of Specifically Binding to Specific Epitopes of CLDN18.2

In one aspect, the present invention relates to a single domain antibody that specifically binds to CLDN18.2 but does not or substantially does not bind to CLDN18.1.

The inventors first discovered a CLDN18.2 binding molecule that can specifically bind to the extracellular domain 1 (ECD1) of human CLDN18.2 (e.g., a single domain antibody that targets CLDN18.2).

As described hereinbefore, CLDN18.2 has two extracellular domains (ECD), wherein the full-length sequence of human CLDN18.2 is as shown in SEQ ID NO: 15, wherein ECD1 is amino acids at positions 28-80 of SEQ ID NO: 15, and is as shown in SEQ ID NO: 19.

```
SEQ ID NO: 15:
MAVTACQGLGFVVSLIGIAGIIAATCMDQWSTQDLYNNPVTAVFNYQGL

WRSCVRESSGFTECRGYFTLLGLPAMLQAVRALMIVGIVLGAIGLLVSI

FALKCIRIGSMEDSAKANMTLTSGIMFIVSGLCAIAGVSVFANMLVTNF

WMSTANMYTGMGGMVQTVQTRYTFGAALFVGWVAGGLTLIGGVMMCTAC
```

-continued
```
RGLAPEETNYKAVSYHASGHSVAYKPGGFKASTGFGSNTKNKKIYDGGA

RTEDEVQSYPSKHDYV

SEQ ID NO: 19:
DQWSTQDLYNNPVTAVFNYQGLWRSCVRESSGFTECRGYFTLLGLPAML

QAVR
```

In addition, the mouse CLDN18.2 is as shown in SEQ ID NO: 17.

```
SEQ ID NO: 17:
MSVTACQGLGFVVSLIGFAGTTAATCMDQWSTQDLYNNPVTAVFNYQGL

WRSCVRESSGFTECRGYFTLLGLPAMLQAVRALMIVGIVLGVIGILVSI

FALKCIRIGSMDDSAKAKMTLTSGILFIISGICAIIGVSVFANMLVTNF

WMSTANMYSGMGGMGGMVQTVQTRYTFGAALFVGWVAGGLTLIGGVMMC

IACRGLTPDDSNFKAVSYHASGQNVAYRPGGFKASTGFGSNTRNKKIYD

GGARTEDDEQSHPTKYDYV
```

As to the human CLDN18.1 and mouse CLDN18.1, the sequences thereof are as shown in SEQ ID NO: 16 and SEQ ID NO: 18, respectively.

```
SEQ ID NO: 16:
MSTTTCQVVAFLLSILGLAGCTAATGMDMWSTQDLYDNPVTSVFQYEGL

WRSCVRQSSGFTECRPYFTILGLPAMLQAVRALMIVGIVLGAIGLLVSI

FALKCIRIGSMEDSAKANMTLTSGIMFIVSGLCAIAGVSVFANMLVTNF

WMSTANMYTGMGGMVQTVQTRYTFGAALFVGWVAGGLTLIGGVMMCTAC

RGLAPEETNYKAVSYHASGHSVAYKPGGFKASTGFGSNTKNKKIYDGGA

RTEDEVQSYPSKHDYV

SEQ ID NO: 18:
MATTTCQVVGLLLSLLGLAGCIAATGMDMWSTQDLYDNPVTAVFQYEGL

WRSCVQQSSGFTECRPYFTILGLPAMLQAVRALMIVGIVLGVIGILVSI

FALKCTRIGSVDDSAKAKMTLTSGILFIISGICAIIGVSVFANMLVTNF

WMSTANMYSGMGGMGGMVQTVQTRYTFGAALFVGWVAGGLTLIGGVMMC

IACRGLTPDDSNFKAVSYHASGQNVAYRPGGFKASTGFGSNTRNKKIYD

GGARTEDDEQSHPTKYDYV
```

CLDN18.2 Antibody Comprising CDRs Having a Certain Sequence Identity to Specific Sequences In some embodiments, the CLDN18.2 antibody of the present disclosure comprises at least one immunoglobulin single variable domain (e.g., VHH), wherein the VHH comprises CDR1, CDR2 and CDR3, and wherein the CDR1 comprises an amino acid sequence at least 80% identical to SEQ ID NO: 1, the CDR2 comprises an amino acid sequence at least 80% identical to SEQ ID NO: 2, the CDR3 comprises an amino acid sequence at least 80% identical to SEQ ID NO: 3.

Unless stated otherwise, assignment of amino acids to each CDR can be based on one of the numbering schemes provided below: Kabat et al., (1991) *Sequences of Proteins of Immunological Interest* (5th Ed.), US Dept. of Health and Human Services, *PHS, NIH, NIH Publication no.* 91-3242; Chothia et al., 1987, PMID: 3681981; Chothia et al., 1989, PMID: 2687698; MacCallum et al., 1996, PMID: 8876650;

or Dubel, Ed. (2007) *Handbook of Therapeutic Antibodies,* 3*rd* Ed., Wily-VCH Verlag GmbH and Co.

Variable regions and CDRs in the antibody sequence can be identified according to general rules that have been developed in the art (as described above, e.g., the Kabat numbering system) or by aligning the sequence with a database of known variable regions. Methods for identifying these regions are described in Kontermann and Dubel, eds., Antibody Engineering, Springer, New York, NY, 2001 and Dinarello et al., Current Protocols in Immunology, John Wiley and Sons Inc., Hoboken, NJ, 2000. Exemplary databases of antibody sequences are described in and available at the website "Abysis": www.bioinf.org.uk/abs (maintained by A. C. Martin, Department of Biochemistry & Molecular Biology University College London, London, England) and website VBASE2: www.vbase2.org, and are described in Retter et al., Nucl. Acids Res., 33 (Database issue): D671-D674 (2005). Abysis database is preferably used for analyzing sequences, and the database integrates the sequence data from Kabat, IMGT and Protein Data Bank (PDB) and the structure data from PDB, see *Protein Sequence and Structure Analysis of Antibody Variable Domains.* in the book: *Antibody Engineering Lab Manual* by Dr. Andrew C. R. Martin (Ed.: Duebel, S. and Kontermann, R., Springer-Verlag, Heidelberg, ISBN-13:978-3540413547, which can also be available at the website: bioinforg.uk/abs). Abysis database website also includes general rules that have been developed to identify the CDRs that can be used in accordance with the teaching herein.

The percent identity between two amino acid sequences can be determined using the algorithm of E. Meyers and W. Miller (Comput. Appl. Biosci., 4:11-17 (1988)) which has been incorporated into the ALIGN program (version 2.0), and a PAM120 weight residue table, a gap length penalty of 12 and a gap penalty of 4 are used. In addition, the percent identity between two amino acid sequences can be determined using the Needleman and Wunsch algorithm (J. Mol. Biol. 48:444-453 (1970)) which has been incorporated into the GAP program in the GCG software package (available at http://www.gcg.com), and a Blossom 62 matrix or a PAM250 matrix, a gap weight of 16, 14, 12, 10, 8, 6, or 4 and a length weight of 1, 2, 3, 4, 5, or 6 are used.

Additionally, or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, with score=50 and word length=3 to obtain amino acid sequences homologous to antibody molecules of the present invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and NBLAST) can be used (see www.ncbi.nlm.nih.gov).

In some other embodiments, the amino acid sequences of the CDRs can be at least 85%, 86%, 87%, 88%, 89%, 90%, 91%, 92%, 93%, 94%, 95%, 96%, 97%, 98%, or 99% identical to respective sequences set forth above.

CLDN18.2 Antibody Comprising CDRs Having Amino Acid Addition, Deletion or Substitution In some embodiments, the CLDN18.2 antibody of the present disclosure comprises at least one immunoglobulin single variable domain (e.g., VHH), wherein the VHH comprises CDR1, CDR2 and CDR3, and wherein the amino acid sequence of CDR 1 differs from SEQ ID NO: 1 by amino acid addition, deletion or substitution of not more than 2 amino acids; the amino acid sequence of CDR2 differs from SEQ ID NO: 2 by amino acid addition, deletion or substitution of not more than 2 amino acids; and/or the amino acid sequence of CDR3 differs from SEQ ID NO: 3 by amino acid addition, deletion or substitution of not more than 2 amino acids. For example, CDR1, CDR2 and CDR3 differ from the amino acid sequences as shown in SEQ ID NO: 1, SEQ ID NO: 2 and SEQ ID NO: 3 respectively by amino acid addition, deletion or substitution of only one amino acid.

Preferably, the CDR of the isolated antibody or antigen binding portion thereof contains conservative substitution of no more than 2 amino acids or no more than 1 amino acid. As used herein, the term "conservative substitution" refers to amino acid substitution that does not negatively affect or change the basic property of the protein/polypeptide comprising amino acid sequences. For example, conservative substitution can be introduced by standard techniques known in the art (such as site-directed mutagenesis and PCR-mediated mutagenesis). Conservative amino acid substitution comprises one in which the amino acid residue is substituted with an amino acid residue having a similar side chain, such as, a physically or functionally similar residue (e.g., having similar sizes, shapes, charges, chemical properties including the ability to form a covalent bond or hydrogen bond, etc.) is substituted by a corresponding amino acid residue. Families of amino acid residues having similar side chains have been defined in the art. These families include amino acids having basic side chains (e.g., lysine, arginine, and histidine), amino acids having acidic side chains (e.g., aspartic acid and glutamic acid), amino acids having uncharged polar side chains (e.g., glycine, asparagine, glutamine, serine, threonine, tyrosine, cysteine, and tryptophan), amino acids having nonpolar side chains (e.g., alanine, valine, leucine, isoleucine, proline, phenylalanine, and methionine), amino acids having beta-branched side chains (e.g., threonine, valine, and isoleucine) and amino acids having aromatic side chains (e.g., tyrosine, phenylalanine, tryptophan, and histidine). Therefore, a corresponding amino acid residue is preferably substituted with another amino acid residue from the family having the same side chain. Methods for identifying amino acid conservative substitutions are well known in the art (see e.g., Brummell et al., Biochem. 32:1180-1187 (1993); Kobayashi et al., Protein Eng. 12 (10): 879-884 (1999); and Burks et al., Proc. Natl. Acad. Sci. USA 94:412-417 (1997), which are incorporated herein by reference).

In certain embodiments, the immunoglobulin single variable domain of the CLDN18.2 antibody comprises:
   i) CDR1 having the amino acid sequence as shown in SEQ ID NO: 1;
   ii) CDR2 having the amino acid sequence as shown in formula ISRGGXIT (SEQ ID NO: 65), wherein $X_1$ is T or S; and
   iii) CDR3 having the amino acid sequence as shown in formula NAQAWDX$_2$GTX$_3$RYLEV (SEQ ID NO: 66), wherein $X_2$ is P or V and $X_3$ is F or I.

In certain embodiments, the immunoglobulin single variable domain of the CLDN18.2 antibody comprises:
   i) CDR1 having the amino acid sequence as shown in SEQ ID NOs: 30, 33, 34, 35, 36, 38, 39, or 40;
   ii) CDR2 having the amino acid sequence as shown in formula X$_4$STGGTT (SEQ ID NO: 67), wherein $X_4$ is I or M; and iii) CDR3 having the amino acid sequence as shown in formula NVLVX$_5$SGIGSX$_6$LEV (SEQ ID NO: 68), wherein X$_5$ is I or V and X$_6$ is H or T.

CLDN18.2 Antibody Comprising CDRs

In some embodiments, the CLDN18.2 antibody of the present disclosure comprises at least one immunoglobulin single variable domain (e.g., VHH), wherein the VHH comprises CDR1, CDR2 and CDR3, and wherein the CDR1, CDR2 and CDR3 are selected from:

(a) CDR1 comprising the amino acid sequence as shown in SEQ ID NO: 1, CDR2 comprising the amino acid sequence as shown in SEQ ID NO: 2, and CDR3 comprising the amino acid sequence as shown in SEQ ID NO: 3;

(b) CDR1 comprising the amino acid sequence as shown in SEQ ID NO: 1, CDR2 comprising the amino acid sequence as shown in SEQ ID NO: 4, and CDR3 comprising the amino acid sequence as shown in SEQ ID NO: 5, or (c) CDR1 comprising the amino acid sequence as shown in SEQ ID NO: 1, CDR2 comprising the amino acid sequence as shown in SEQ ID NO: 2, and CDR3 comprising the amino acid sequence as shown in SEQ ID NO: 6.

In some embodiments, the CLDN18.2 antibody of the present disclosure comprises at least one immunoglobulin single variable domain (e.g., VHH), wherein the VHH comprises CDR1, CDR2 and CDR3, and wherein the CDR1, CDR2 and CDR3 are selected from:

(a) CDR1 comprising the amino acid sequence as shown in SEQ ID NO: 30, CDR2 comprising the amino acid sequence as shown in SEQ ID NO: 31, and CDR3 comprising the amino acid sequence as shown in SEQ ID NO: 32;

(b) CDR1 comprising the amino acid sequence as shown in SEQ ID NO: 30, CDR2 comprising the amino acid sequence as shown in SEQ ID NO: 31, and CDR3 comprising the amino acid sequence as shown in SEQ ID NO: 37;

(c) CDR1 comprising the amino acid sequence as shown in SEQ ID NO: 33, CDR2 comprising the amino acid sequence as shown in SEQ ID NO: 31, and CDR3 comprising the amino acid sequence as shown in SEQ ID NO: 62;

(d) CDR1 comprising the amino acid sequence as shown in SEQ ID NO: 33, CDR2 comprising the amino acid sequence as shown in SEQ ID NO: 31, and CDR3 comprising the amino acid sequence as shown in SEQ ID NO: 37;

(e) CDR1 comprising the amino acid sequence as shown in SEQ ID NO: 34, CDR2 comprising the amino acid sequence as shown in SEQ ID NO: 31, and CDR3 comprising the amino acid sequence as shown in SEQ ID NO: 37;

(f) CDR1 comprising the amino acid sequence as shown in SEQ ID NO: 35, CDR2 comprising the amino acid sequence as shown in SEQ ID NO: 31, and CDR3 comprising the amino acid sequence as shown in SEQ ID NO: 62;

(g) CDR1 comprising the amino acid sequence as shown in SEQ ID NO: 36, CDR2 comprising the amino acid sequence as shown in SEQ ID NO: 31, and CDR3 comprising the amino acid sequence as shown in SEQ ID NO: 62;

(h) CDR1 comprising the amino acid sequence as shown in SEQ ID NO: 38, CDR2 comprising the amino acid sequence as shown in SEQ ID NO: 31, and CDR3 comprising the amino acid sequence as shown in SEQ ID NO: 62;

(i) CDR1 comprising the amino acid sequence as shown in SEQ ID NO: 39, CDR2 comprising the amino acid sequence as shown in SEQ ID NO: 41, and CDR3 comprising the amino acid sequence as shown in SEQ ID NO: 37; or (j) CDR1 comprising the amino acid sequence as shown in SEQ ID NO: 40, CDR2 comprising the amino acid sequence as shown in SEQ ID NO: 31, and CDR3 comprising the amino acid sequence as shown in SEQ ID NO: 37.

In some embodiments, the CLDN18.2 antibody of the present disclosure comprises at least one immunoglobulin single variable domain (e.g., VHH), wherein the VHH comprises CDR1, CDR2 and CDR3, and wherein the CDR1, CDR2 and CDR3 are selected from:

(a) CDR1 having the amino acid sequence as shown in SEQ ID NO: 1, CDR2 having the amino acid sequence as shown in SEQ ID NO: 2, and CDR3 having the amino acid sequence as shown in SEQ ID NO: 3;

(b) CDR1 having the amino acid sequence as shown in SEQ ID NO: 1, CDR2 having the amino acid sequence as shown in SEQ ID NO: 4, and CDR3 having the amino acid sequence as shown in SEQ ID NO: 5; or (c) CDR1 having the amino acid sequence as shown in SEQ ID NO: 1, CDR2 having the amino acid sequence as shown in SEQ ID NO: 2, and CDR3 having the amino acid sequence as shown in SEQ ID NO: 6.

In some embodiments, the CLDN18.2 antibody of the present disclosure comprises at least one immunoglobulin single variable domain (e.g., VHH), wherein the VHH comprises CDR1, CDR2 and CDR3, and wherein the CDR1, CDR2 and CDR3 are selected from:

(a) CDR1 having the amino acid sequence as shown in SEQ ID NO: 30, CDR2 having the amino acid sequence as shown in SEQ ID NO: 31, and CDR3 having the amino acid sequence as shown in SEQ ID NO: 32;

(b) CDR1 having the amino acid sequence as shown in SEQ ID NO: 30, CDR2 having the amino acid sequence as shown in SEQ ID NO: 31, and CDR3 having the amino acid sequence as shown in SEQ ID NO: 37;

(c) CDR1 having the amino acid sequence as shown in SEQ ID NO: 33, CDR2 having the amino acid sequence as shown in SEQ ID NO: 31, and CDR3 having the amino acid sequence as shown in SEQ ID NO: 62;

(d) CDR1 having the amino acid sequence as shown in SEQ ID NO: 33, CDR2 having the amino acid sequence as shown in SEQ ID NO: 31, and CDR3 having the amino acid sequence as shown in SEQ ID NO: 37;

(e) CDR1 having the amino acid sequence as shown in SEQ ID NO: 34, CDR2 having the amino acid sequence as shown in SEQ ID NO: 31, and CDR3 having the amino acid sequence as shown in SEQ ID NO: 37;

(f) CDR1 having the amino acid sequence as shown in SEQ ID NO: 35, CDR2 having the amino acid sequence as shown in SEQ ID NO: 31, and CDR3 having the amino acid sequence as shown in SEQ ID NO: 62;

(g) CDR1 having the amino acid sequence as shown in SEQ ID NO: 36, CDR2 having the amino acid sequence as shown in SEQ ID NO: 31, and CDR3 having the amino acid sequence as shown in SEQ ID NO: 62;

(h) CDR1 having the amino acid sequence as shown in SEQ ID NO: 38, CDR2 having the amino acid sequence as shown in SEQ ID NO: 31, and CDR3 having the amino acid sequence as shown in SEQ ID NO: 62;

(i) CDR1 having the amino acid sequence as shown in SEQ ID NO: 39, CDR2 having the amino acid sequence as shown in SEQ ID NO: 41, and CDR3 having the amino acid sequence as shown in SEQ ID NO: 37; and (j) CDR1 having the amino acid sequence as shown in SEQ ID NO: 40, CDR2 having the amino acid sequence as shown in SEQ ID NO: 31, and CDR3 having the amino acid sequence as shown in SEQ ID NO: 37.

CLDN18.2 Antibody Defined with VHH Sequence

In some embodiments, the CLDN18.2 antibody of the present disclosure comprises at least one (e.g., one) immunoglobulin single variable domain (e.g., VHH), wherein the VHH comprises:

(A) the amino acid sequence as shown in SEQ ID NOs: 7, 47 or 63;

(B) an amino acid sequence at least 80%, 85%, 90% or 95% identical to SEQ ID NOs: 7, 47 or 63; or (C) an amino acid sequence having addition, deletion and/or substitution of one or more (e.g., 1, 2, 3, 4, 5, 6, 7, 8, 9, or 10) amino acids compared to SEQ ID NOs: 7, 47, or 63.

In some embodiments, the CLDN18.2 antibody of the present disclosure comprises at least one (e.g., one) immunoglobulin single variable domain (e.g., VHH), wherein the VHH:

(A) consists of the amino acid sequence as shown in SEQ ID NOs: 7, 47 or 63;

(B) consists of an amino acid sequence at least 80%, 85%, 90% or 95% identical to SEQ ID NOs: 7, 47 or 63; or (C) consists of an amino acid sequence having addition, deletion and/or substitution of one or more (e.g., 1, 2, 3, 4, 5, 6, 7, 8, 9, or 10) amino acids compared to SEQ ID NOs: 7, 47, or 63.

In other embodiments, the amino acid sequence of the VHH can be at least 85%, 86%, 87%, 88%, 89%, 90%, 91%, 92%, 93%, 94%, 95%, 96%, 97%, 98%, or 99% identical to each sequence mentioned above. As an illustrative example, the antibody can comprise a VHH having at least 85%, 86%, 87%, 88%, 89%, 90%, 91%, 92%, 93%, 94%, 95%, 96%, 97%, 98% or 99% sequence identity to SEQ ID NOs: 7, 47 or 63.

In some further embodiments, the CLDN18.2 antibody of the present disclosure can comprise conservative amino acid substitution or modification in the heavy chain variable region. It is understood in the art that certain conservative sequence modifications can be made that do not eliminate the antigen binding properties. See e.g., Brummell et al., (1993) Biochem 32:1180-8; de Wildt et al., (1997) Prot. Eng. 10:835-41; Komissarov et al., (1997) J. Biol. Chem. 272: 26864-26870; Hall et al., (1992) J. Immunol. 149:1605-12; Kelley and O'Connell (1993) Biochem. 32:6862-35; Adib-Conquy et al., (1998) Int. Immunol. 10:341-6 and Beers et al., (2000) Clin. Can. Res. 6:2835-43.

In certain embodiments, the single domain CLDN18.2 antibody of the present disclosure has modification(s) (e.g., substitution of amino acid(s)) at one or more of the following positions in SEQ ID NO: 7: the amino acid at position 1, 4, 5, 14, 16, 35, 47, 56, 58, 65, 92, 102, 105, or 121. In certain embodiments, the single domain CLDN18.2 antibody of the present disclosure has modification(s) (e.g., substitution of amino acid(s)) at one or more of the following positions in SEQ ID NO: 47: the amino acid at position 1, 4, 5, 11, 27, 28, 29, 30, 31, 32, 35, 51, 75, 76, 92, 100, 106, or 120.

In some particular embodiments, the variable region of the single domain CLDN18.2 antibody of the present disclosure comprises any one of SEQ ID NOs: 7, 8, 9, 10, 11, 12, 13, 14, 42, 43, 44, 45, 46, 47, 48, 49, 50, 51 and 633.

In some particular embodiments, the variable region of the single domain CLDN18.2 antibody of the present disclosure consists of any one of SEQ ID NOs: 7, 8, 9, 10, 11, 12, 13, 14, 42, 43, 44, 45, 46, 47, 48, 49, 50, 51 and 63.

A Nucleic Acid Molecule that Encodes the Antibody of the Present Disclosure

In some aspects, the present invention relates to an isolated nucleic acid molecule, comprising a nucleic acid sequence that encodes the CLDN18.2 antibody of the present disclosure or a variable region fragment thereof.

The nucleic acid of the present invention can be obtained by using standard molecular biology techniques. For antibodies obtained from an immunoglobulin gene library (e.g., using phage display techniques), the nucleic acid encoding such an antibody can be recovered from the library.

The sequences of exemplary nucleic acid molecules of the present invention are as shown in any one of SEQ ID NOs: 22, 23, 24, 25, 26, 27, 28, 29, 52, 53, 54, 55, 56, 57, 58, 59, 60, 61 and 64.

In some embodiments, the nucleic acid has at least 80% (e.g., at least 85%, 86%, 87%, 88%, 89%, 90%, 91%, 92%, 93%, 94%, 95%, 96%, 97%, 98%, or 99%) sequence identity to the nucleic acid molecule as shown in any one of SEQ ID NOS: 22, 23, 24, 25, 26, 27, 28, 29, 52, 53, 54, 55, 56, 57, 58, 59, 60, 61 and 64, respectively. In some embodiments, the percentage of identity is derived from the degeneracy of the genetic code, and the protein sequence encoded remains unchanged.

The nucleic acid molecule that encodes the CLDN18.2 antibody of the present disclosure can be inserted into a vector for further cloning (DNA amplification) or for expression by using recombinant techniques known in the art. Many vectors are available. Vectors or vector components generally include but are not limited to one or more of the following: a signal sequence, an origin of replication, one or more marker genes, enhancer elements, a promoter (such as SV40, CMV, and EF-1α), and a transcription termination sequence. Selection marker genes facilitate the selection of a host cell into which a vector has been introduced (see e.g., U.S. Pat. Nos. 4,399,216; 4,634,665 and 5,179,017). For example, selection marker genes generally confer drug (e.g., G418, hygromycin, or methotrexate) resistance to the host cell into which the vector has been introduced. In one embodiment, selection marker genes can include dihydrofolate reductase (DHFR) gene (for dhfr-host cells with methotrexate selection/amplification) and neo gene (for G418 selection). In another embodiment, the antibody can be produced by homologous recombination known in the art. DNA encoding the monoclonal antibody is readily isolated and sequenced using conventional procedures (e.g., by using an oligonucleotide probe capable of specifically binding to the gene that encodes the heavy chain of the antibody).

In some embodiments, the vector system includes mammalian, bacterial, yeast systems, etc., and includes plasmids such as but not limited to pALTER, pBAD, pcDNA, pCal, pL, pET, pGEMEX, pGEX, pCI, pCMV, pEGFP, PEGFT, pSV2, pFUSE, pVITRO, pVIVO, pMAL, pMONO, pSE-LECT, pUNO, pDUO, Psg5L, pBABE, pWPXL, pBI, p15TV-L, pPro18, pTD, pRS420, pLexA, pACT2.2, etc., and other lab-available and commercially available vectors. Suitable vectors can include plasmid vectors or viral vectors (e.g., replication defective retroviruses, adenoviruses and adeno-associated viruses). In one embodiment of the present invention, the vector can be pET, such as pETbac containing a hexa-histidine tag and a c-Myc-tag gene.

The vector comprising the nucleic acid sequence that encodes the CLDN18.2 antibody of the present disclosure can be introduced into a host cell for cloning or gene expression. Suitable host cells for cloning or expressing DNA in the vectors herein are prokaryote, yeast, or higher eukaryote cells. Prokaryotes suitable for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus*, e.g., *B. subtilis* and *B. licheniformis, Pseudomonas*, e.g., *Pseudomonas aeruginosa*, and *Streptomyces*.

In addition to prokaryotes, eukaryotic microbes such as filamentous fungi or yeast are host cells suitable for expressing the CLDN18.2 antibody of the present invention. *Saccharomyces cerevisiae*, or common baker's yeast, is the most commonly used among lower eukaryotic host microorganisms. However, a number of other genera, species, and strains are commonly available and useful in the present invention, such as *Schizosaccharomyces pombe; Kluyveromyces* hosts such as *K. lactis, K. fragilis* (ATCC 12,424), *K. bulgaricus* (ATCC 16,045), K. wickeramii (ATCC 24, 178), *K. waltii* (ATCC 56,500), *K. drosophilarum* (ATCC 36,906), *K. thermotolerans*, and *K. marxianus; yarrowia* (EP 402, 226); *Pichia pastoris* (EP 183,070); *Candida; Trichoderma reesia* (EP 244,234); *Neurospora crassa; Schwanniomyces*, such as *Schwanniomyces occidentalis*; and filamentous fungi such as *Neurospora, Penicillium, Tolypocladium*, and *Aspergillus* hosts such as *A. nidulans* and *A. niger.*

Other host cells suitable for expressing the CLDN18.2 antibody of the present disclosure can be derived from multicellular organisms. Examples of invertebrate cells include plant and insect cells. Currently, numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and according to the present disclosure, such viruses may be used in a transfection process (particularly for transfection of *Spodoptera frugiperda* cells) through which the CLDN18.2 antibody is expressed in a suitable host cell. Plant cell cultures of cotton, corn, potato, soybean, *petunia*, tomato, and tobacco can also be used as hosts.

Host cells are transformed with the vector used for the production of the CLDN18.2 antibody of the present disclosure described above, and are cultured in conventional nutrient media modified as appropriate for inducing promoters, selecting transformants, or amplifying the genes encoding the desired sequences.

The host cells used for producing the CLDN18.2 antibody of the present disclosure may be cultured in a variety of media. Commercially available media such as Ham's F10 (Sigma), Minimal Essential Medium (MEM) (Sigma), RPMI-1640 (Sigma), and Dulbecco's Modified Eagle's Medium (DMEM, Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927, 762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, etc., are those previously used with the host cells selected for expression and will be apparent to the ordinarily skilled artisan.

When using recombinant techniques, the antibody can be produced intracellularly, in the periplasmic space, or directly secreted into the medium. If the antibody is produced intracellularly, as a first step, the particulate and debris (either host cells or lysed fragments), are removed, for example, by centrifugation or ultrafiltration. Carter et al., Bio/Technology 10:163-167 (1992) describe a procedure for isolating antibodies which are secreted to the periplasmic space of *E. coli*. Briefly, cells are thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems can be first concentrated using a commercially available protein concentration filter, e.g., an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

After any preliminary purification steps, the mixture comprising the target antibody and contaminants can be subjected to low pH hydrophobic interaction chromatography using an elution buffer with a pH between about 2.5-4.5, preferably at a low salt concentration (e.g., about 0-0.25 M salt).

Pharmaceutical Composition

In some aspects, the present invention relates to a pharmaceutical composition, comprising at least one CLDN18.2 binding molecule (e.g., the CLDN18.2 antibody of the present disclosure) as disclosed herein and a pharmaceutically acceptable carrier.

Components of Pharmaceutical Composition

The pharmaceutical composition can optionally contain one or more additional pharmaceutical active ingredients, such as another antibody or drug. The pharmaceutical composition of the present invention can also be administered in combination with such as another immunostimulant, anti-cancer agent, antiviral agent or vaccine, so that the anti-CLDN18.2 antibody enhances the immune response to a vaccine. Pharmaceutically acceptable carriers can include such as pharmaceutically acceptable liquid, gel or solid carriers, aqueous media, non-aqueous media, antimicrobial agents, isotonic agents, buffering agents, antioxidants, anesthetics, suspending agents/dispersants, chelating agents, diluents, adjuvants, excipients or non-toxic auxiliary substances, a combination of various components known in the art or more.

Suitable components can include such as antioxidants, fillers, binders, disintegrants, buffering agents, preservatives, lubricants, flavoring agents, thickening agents, coloring agents, emulsifying agents or stabilizers such as sugar and cyclodextrin. Suitable antioxidants can include such as methionine, ascorbic acid, EDTA, sodium thiosulfate, platinum, hydrogen peroxidase, citric acid, cysteine, mercaptoglycerol, mercaptoacetic acid, mercaptosorbitol, butylmethyl anisole, butylated hydroxy toluene and/or propyl arsenate. As disclosed in the present invention, in a solvent of an antibody or an antigen binding fragment that comprises one or more antioxidants (e.g., methionine) reducing the antibody or the antigen binding fragment thereof and contains the composition disclosed in the present invention, the one or more antioxidants can be oxidized. Redox can prevent or reduce the decrease in binding affinity, thereby enhancing the antibody stability and extending the shelf life. Therefore, in some embodiments, the present invention provides a composition comprising one or more antibodies or antigen binding fragments thereof and one or more antioxidants such as methionine. The present invention further provides a plurality of methods, wherein an antibody or an antigen binding fragment thereof is mixed with one or more antioxidants such as methionine. Thus, the antibody or the antigen binding fragment thereof can be prevented from oxidation so as to extend its shelf life and/or increase its activity.

For further illustration, pharmaceutically acceptable carriers can include for example aqueous carriers, such as sodium chloride injection, Ringer's injection, isotonic dextrose injection, sterile water injection or dextrose and Lactated Ringer's injection, non-aqueous carriers such as fixed oil of vegetable origin, cottonseed oil, corn oil, sesame oil, or peanut oil, bacteriostats or antimicrobial agents at fungistatic concentrations, isotonic agents such as sodium chloride or glucose, buffering agents such as phosphate or citrate buffering agents, antioxidants such as sodium hydrogen sulfate, local anesthetics such as procaine hydrochloride, suspending agents and dispersants such as sodium carboxymethyl cellulose, hydroxypropyl methylcellulose or polyvinyl pyrrolidone, emulsifying agents such as Polysorbate 80 (TWEEN-80), chelating agents such as EDTA (Ethylene Diamine Tetraacetic Acid) or EGTA (Ethylene Glycol Tetraacetic Acid), ethanol, polyethylene glycol, propylene glycol, sodium hydroxide, hydrochloric acid, citric acid, or lactic acid. The antimicrobial agents useful as vectors can be added to the pharmaceutical composition in a multi-dose container comprising phenol or methylphenol, mercurial preparations, benzyl alcohol, chlorobutanol, methylparaben, and propylparaben, thimerosal, benzalkonium chloride, and benzethonium chloride. Suitable excipients can include such as water, saline, dextrose, glycerol, or ethanol. Suitable non-toxic auxiliary substances can include such as humectants or emulsifying agents, pH buffering agents, stabilizers, solubility-enhancing agents or reagents such as sodium acetate, sorbitan monolaurate, triethanolamine oleate or cyclodextrin.

Administration, Formulation and Dose

The pharmaceutical composition of the present invention can be administered to a subject in need thereof in vivo by a variety of routes including but not limited to oral, intravenous, intraarterial, subcutaneous, parenteral, intranasal, intramuscular, intracranial, intracardiac, intraventricular, intratracheal, buccal, rectal, intraperitoneal, intracutaneous, topical, transdermal and intrathecal administration, or administration by implantation or inhalation. The pharmaceutical composition of the present invention can be formulated into formulations in a solid, semisolid, liquid, or gaseous form, including but not limited to tablets, capsules, powders, granules, ointments, solutions, suppositories, enemas, injections, inhalants and aerosols. Suitable formulations and administration routes can be chosen according to the intended use and treatment regimens.

Formulations suitable for enteral administration include hard or soft gelatin capsules, pills, tablets including coated tablets, elixirs, suspensions, syrups or inhalants, and controlled release dosage forms thereof.

Formulations suitable for parenteral administration (e.g., by injection) include aqueous or non-aqueous, isotonic, pyrogen-free, sterile liquids (e.g., solutions, suspensions) in which the active ingredient is dissolved, suspended or provided otherwise (e.g., in liposomes or other particulates). Such liquids can additionally contain other pharmaceutically acceptable ingredients, such as antioxidants, buffering agents, preservatives, stabilizers, bacteriostats, suspending agents, thickening agents and solutes which render the formulation isotonic with the blood (or other related body fluid) of an intended recipient. Examples of excipients include such as water, alcohol, polyols, glycerol, vegetable oil, etc. Examples of isotonic vectors suitable for such formulations include sodium chloride injection, Ringer's injection or Lactated Ringer's injection. Similarly, the specific dose regimen (i.e., dose, time, and repetition) will depend on the particular individual and the medical history of the individual and empirical considerations such as pharmacokinetics (e.g., half-life, clearance, etc.).

The frequency of administration can be determined and adjusted during the course of treatment and based on the decrease of proliferation or number of tumorigenic cells, the maintenance of the decrease in such tumor cells, the decrease of the proliferation of tumor cells or the delay of the development of metastasis. In some embodiments, the dose administered can be adjusted or reduced so as to control the potential side effects and/or toxicity. Alternatively, sustained continuous release formulations of the pharmaceutical composition of the present invention for treatment may be appropriate.

Those skilled in the art will appreciate that suitable doses may vary from patients. Determining the optimal dose generally involves balancing the level of therapeutic benefits with any risks or detrimental side effects. The selected dose level will depend upon a variety of factors including but no limited to the activity of the particular compound, the administration, the time of administration, the clearance rate of the compound, the duration of the treatment, other drugs, compounds and/or materials used in combination, the severity of the condition, and the species, and the sex, age, weight, pathogenetic condition, general health condition and prior medical history of the patient. The amount and administration route of the compound are ultimately determined by a doctor, veterinarian, or clinician, but a dose is generally selected to reach a local concentration at the site of action that achieves the desired effect without causing substantial detrimental or unfavorable side effects.

Generally, the CLDN18.2 binding molecule can be administered in various dose ranges. In some embodiments, the CLDN18.2 binding molecule provided herein can be administered at the therapeutically effective dose of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In some of these embodiments, the antibody is administered at a dose of about 50 mg/kg or less, and in some of these embodiments, the dose is 10 mg/kg or less, 5 mg/kg or less, 1 mg/kg or less, 0.5 mg/kg or less, or 0.1 mg/kg or less. In certain embodiments, the dose administered can vary during the course of treatment. For example, in certain embodiments, the initial dose administered can be greater than the dose administered subsequently. In certain embodiments, the dose administered can vary during the course of treatment depending on the response of a subject.

In any case, the antibody of the present invention or the antigen binding portion thereof is preferably administered to a subject in need thereof as needed. The frequency of administration can be determined by those skilled in the art, such as an attending physician based on considerations such as the condition being treated, the age of the subject being treated, the severity of the condition being treated, the general health condition of the subject being treated.

In some preferred embodiments, the course of treatment that involves the antibody of the present invention or an antigen binding portion thereof will comprise multiple doses of the selected pharmaceutical product administered in a period of several weeks or several months. More specifically, the antibody of the present invention or the antigen binding portion thereof can be administered daily, every two days, every four days, weekly, every ten days, every other week, every three weeks, monthly, every six weeks, every other month, every ten weeks, or every three months. In this regard, it is understandable that the dose can be changed or the interval can be adjusted based on patient responses and clinical practice.

The dose and regimen of the disclosed pharmaceutical composition for treatment can also be determined empirically in individuals who have been given one or more administrations. For example, an individual may be given incremental doses of the pharmaceutical composition described herein. In a selected embodiment, the doses can be determined empirically, or increased or reduced gradually according to the side effects or toxicity observed, respectively. To assess the efficacy of the selected composition, the markers of a particular disease, condition or pathogenic condition can be tracked. For cancer, these include direct measurements of tumor size via palpation or visual observation, indirect measurement of tumor size by X-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life or prolongation of survival as measured by accepted tests. It will be apparent to those skilled in the art that the dose will vary depending on the individual, the type of pathogenetic condition of the tumor, the stage of pathogenetic condition of the tumor, and the fact whether the pathogenetic condition of the cancer has begun to metastasize to other location in the individual, and the past and concurrent treatments being used.

Compatible formulations for parenteral administration (e.g., intravenous injection) may comprise the CLDN18.2 binding molecule as provided herein at the concentration from about 10 µg/ml to about 100 mg/ml. In some embodiments, the concentration of the CLDN18.2 binding molecule can include 20 µg/ml, 40 µg/ml, 60 µg/ml, 80 µg/ml, 100 µg/ml, 200 µg/ml, 300 µg/ml, 400 µg/ml, 500 µg/ml, 600 ug/ml, 700 µg/ml, 800 µg/ml, 900 µg/ml or 1 mg/ml. In other preferred embodiments, the concentration of the CLDN18.2 binding molecule includes 2 mg/ml, 3 mg/ml, 4 mg/ml, 5 mg/ml, 6 mg/ml, 8 mg/ml, 10 mg/ml, 12 mg/ml, 14 mg ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, or 100 mg/ml. In some embodiments, the concentration of the CLDN18.2 binding molecule can include 133 nM, 266 nM, 400 nM, 533 nM, 667 nM, 1.3 µM, 2 µM, 2.67 µM, 3.33 µM, 4 µM, 4.67 µM, 5.33 µM, 6 µM, or 6.67 µM, if calculated by molarity.

Use of the Present Invention

The CLDN18.2 binding molecule of the present invention has a number of in vitro and in vivo uses.

Treatment of Diseases

Conditions and disorders associated with CLDN18.2 can be immune-related diseases or conditions comprising but not limited to "diseases relating to cells expressing CLDN18.2" or "diseases associated with cells expressing CLDN18.2" or similar expressions and means that CLDN18.2 expresses in cells of the diseased tissues or organs. In one embodiment, compared to the state of a corresponding healthy tissue or organ, the expression of CLDN18.2 in cells of a diseased tissue or organ increases. The increase refers to an increase of at least 10%, particularly at least 20%, at least 50%, at least 100%, at least 200%, at least 500%, at least 1000%, at least 10000% or even more. In one embodiment, expression is only found in a diseased tissue, and the expression in the corresponding healthy tissue is inhibited. According to the present invention, diseases associated with cells expressing CLDN18.2 include cancerous diseases. In addition, according to the present invention, cancerous diseases are preferably those where cancer cells express CLDN18.2.

The term "cancerous disease" or "cancer" refers to or describes the physiological condition that is typically characterized by unregulated cell growth. Examples of cancers include but are not limited to epithelial cancer, lymphoma, blastoma, sarcoma, and leukemia. More particularly, examples of such cancers include bone cancer, blood cancer, lung cancer, hepatic cancer, pancreatic cancer, skin cancer, head-neck cancer, cutaneous or intraocular melanoma, uterine cancer, ovarian cancer, rectal cancer, cancer of the anal region, gastric cancer, colon cancer, breast cancer, prostate cancer, cancers of sexual organs and reproductive organs, Hodgkin's disease, esophageal cancer, small intestine cancer, cancers of endocrine system, thyroid cancer, parathyroid carcinoma, adrenal cancer, soft tissue sarcomas, bladder cancer, renal cancer, renal cell carcinoma, renal pelvis cancer, central nervous system (CNS) tumor, neuroectodermal cancer, spinal axis tumor, glioma, meningioma, and pituitary adenoma. The term "cancer" according to the present invention also includes cancer metastasis. Preferably, "cancerous diseases" are characterized in cells expressing CLDN18.2 and the feature that cancer cells express CLDN18.2. Cells expressing CLDN18.2 are preferably cancer cells, preferably cancer cells of the cancers described herein.

According to the present disclosure, the term "tumor" or "tumor disease" refers to an abnormal growth of cells (called neoplastic cells, tumorigenous cells or tumor cells), preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant. According to the present invention, a "cancerous disease" is preferably a "tumor disease". However, the terms "cancer" and "tumor", typically, can be used interchangeably herein.

In one embodiment, the cancer according to the present disclosure relates to cancer cells expressing CLDN18.2. In one embodiment, the cancer is CLDN18.2 positive. In one embodiment, CLDN18.2 expression is at the surface of the cells. In one embodiment, at least 50%, preferably 60%, 70%, 80% or 90% of the cancer cells are CLDN18.2 positive, and/or at least 40%, preferably at least 50% of the cancer cells are positive for the surface expression of CLDN18.2. In one embodiment, at least 95% or at least 98% of the cancer cells are CLDN18.2 positive. In one embodiment, at least 60%, at least 70%, at least 80% or at least 90% of the cancer cells are positive for the surface expression of CLDN18.2.

In one embodiment, cancers expressing CLDN18.2, cancers relating to cancer cells expressing CLDN18.2, or CLDN18.2 positive cancers are selected from: gastric cancer, esophageal cancer, pancreatic cancer, lung cancer (such as non small cell lung cancer (NSCLC)), ovarian cancer, colon cancer, hepatic cancer, head-neck cancer, and gall-bladder cancer and metastases thereof, in particular gastric cancer metastasis (such as Krukenberg tumors), peritoneal metastasis and lymph node metastasis. In one embodiment, the cancer is an adenocarcinoma, in particular an advanced adenocarcinoma. Particularly preferred cancerous diseases are adenocarcinomas of the stomach, the esophagus, the pancreatic duct, the bile ducts, the lung and the ovary. In one embodiment, the cancers are selected from gastric cancer, esophageal cancer (in particular the cancer of the lower esophagus), cancer of the esophagogastric junction and gastroesophageal cancer. In a particularly preferred embodiment, the cancers are gastroesophageal cancer such as metastatic, refractory or recurrent advanced gastroesophageal cancer.

In addition, the antibody of the present disclosure or an antigen binding portion thereof can be used in combination with chemotherapy or radiotherapy.

Combined Use with Chemotherapies

The antibody or the antigen binding portion thereof may be used in combination with an anti-cancer agent, a cytotoxic agent or chemotherapeutic agent.

The term "anti-cancer agent" or "anti-proliferative agent" means any agent that can be used to treat a cell proliferative condition such as cancers, and includes, but is not limited to, cytotoxic agents, cytostatic agents, anti-angiogenic agents, radiotherapy and radiotherapeutic agents, targeted anti-cancer agents, BRMs, therapeutic antibodies, cancer vaccines, cytokines, hormone therapies, and anti-metastatic agents and immunotherapeutic agents. It will be appreciated that, in selected embodiments as discussed above, such anti-cancer agents may comprise conjugates and may be associated with the disclosed site-specific antibodies prior to administration. More particularly, in some embodiments, selected anti-cancer agents will be linked to the unpaired cysteines of the engineered antibodies to provide engineered conjugates as set forth herein. Accordingly, such engineered conjugates are expressly contemplated as being within the scope of the instant disclosure. In other embodiments, the disclosed anti-cancer agents will be administered in combination with a site-specific conjugate comprising a different therapeutic agent as set forth above.

As used herein, the term "cytotoxic agent" means a substance that is toxic to cells and decreases or inhibits the function of the cells and/or causes destruction of the cells. In some embodiments, the substance is a naturally occurring molecule derived from a living organism. Examples of cytotoxic agents include, but are not limited to, small molecule toxins or enzymatically active toxins from bacteria (e.g., Diptheria toxin, *Pseudomonas* endotoxin and exo-toxin, Staphylococcal enterotoxin A), fungi (e.g., alpha-sarcin, restrictocin), plants (e.g., abrin, ricin, volkensin, viscumin, pokeweed anti-viral protein, saporin, gelonin, momoridin, trichosanthin, barley toxin, *Aleurites fordii* pro-teins, dianthin proteins, *Phytolacca* mericana proteins (PAPI, PAPII, and PAP-S), *Momordica charantia* inhibitor, curcin, crotin, *Saponaria officinalis* inhibitor, mitegellin, phenomycin, neomycin, and the tricothecenes), or animals (e.g., cytotoxic RNases, such as extracellular pancreatic RNases; DNase I, including fragments and/or variants thereof).

For the purposes of the present invention, a "chemothera-peutic agent" comprises a chemical compound that non-specifically decreases or inhibits the growth, proliferation, and/or survival of cancer cells (e.g., cytotoxic or cytostatic agents). Such chemical agents are often directed to intrac-ellular processes necessary for cell growth or division, and are thus particularly effective against cancer cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancer cell or a cell likely to become a cancer cell or generate tumorigenic progeny (e.g., TIC). Such agents are often administered in combination, and are often most effective, e.g., in regimens such as CHOP or FOLFIRI.

Examples of anti-cancer agents that may be used in combination with the site-specific constructs of the present invention (either as a component of a site specific conjugate or in an unconjugated state) include, but are not limited to, alkylating agents, alkyl sulfonates, aziridines, ethylenimines and methylmelamines, acetogenins, camptothecin, bryosta-tin, callystatin, CC-1065, cryptophycins, dolastatin, duocar-mycin, eleutherobin, pancratistatin, sarcodictyin, spongista-tin, nitrogen mustards, antibiotics, enediyne antibiotics, dynemicin, bisphosphonates, esperamicin, chromoprotein enediyne antiobiotic chromophores, aclacinomysins, actino-mycin, anthramycin, azaserine, bleomycins, actinomycin C, carabicin, carminomycin, carzinophillin, chromomycinis, dactinomycin, daunorubicin, detorubicin, 6-diazo-5-oxo-L-norleucine, ADRIAMYCIN® doxorubicin, epirubicin, eso-rubicin, idarubicin, marcellomycin, mitomycins, mycophe-nolic acid, nogalamycin, olivomycins, peplomycin, potfiromycin, puromycin, triferricdoxorubicin, rodorubicin, streptonigrin, streptozocin, tubercidin, ubenimex, zinostatin, zorubicin; anti-metabolites, erlotinib, vemurafenib, crizo-tinib, sorafenib, ibrutinib, enzalutamide, folic acid ana-logues, purine analogs, androgens, antiadrenergic agents, folic acid supplements such as frolinic acid, aceglatone, aldophosphamide glycoside, aminolevulinic acid, eniluracil, amsacrine, bestrabucil, bisantrene, edatrexate, defofamine, demecolcine, diaziquone, elfornithine, elliptinium acetate, epothilone （爱波喜龙）, etoglucid, gallium nitrate, hydroxyurea, lentinan, lonidamine, maytansinoids, mitogua-zone, mitoxantrone, mopidanmol, nitraerine, pentostatin, phenamet, pirarubicin, losoxantrone, podophyllinic acid, 2-ethylhydrazine, procarbazine, PSK® polysaccharide complex (JHS Natural Products, Eugene, OR), razoxane; rhizoxin; sizofiran; spirogermanium; tenuazonic acid; triazi-quone; 2,2',2"-trichlorotriethylamine; trichothecenes (especially T-2 toxin, verracurin A, roridin A and anguidin); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® TIL-2; LURTOTECAN® topoisomerase 1 inhibitor; ABARELIX® rmRH; Vinorelbine and Esperamicins and pharmaceutically acceptable salts, acids or derivatives of any of the above.

Combined Use with Radiotherapies

The present invention also provides for the combination of the antibody or the antigen binding portion thereof with radiotherapies (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiotherapy is administered in pulses over a period of time from about 1 to about 2 weeks. The radiotherapy may be administered to subjects having head-neck cancer for about 6 to 7 weeks. Optionally, the radiotherapy may be administered as a single dose or as multiple, sequential doses.

Diagnosis

The present invention provides in vitro and in vivo methods for detecting, diagnosing or monitoring proliferative conditions and methods of screening cells from a patient to identify tumor cells including tumorigenic cells. Such methods include identifying an individual having cancer for treatment or monitoring progression of a cancer, comprising contacting the patient or the sample obtained from the patient (either in vivo or in vitro) with the antibody as described herein and detecting presence or absence, or level of binding, of the antibody binding to bound or free target molecules in the sample. In some embodiments, the antibody will comprise a detectable label or reporter molecule.

In some embodiments, the binding of the antibody with particular cells in the sample can denote that the sample may contain tumorigenic cells, thereby indicating that the individual having cancers may be effectively treated with the antibody as described herein.

Samples can be analyzed by numerous assays, for example, radioimmunoassays, enzyme immunoassays (e.g., ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g., CAT scan), positron tomography (e.g., PET scan), radiography, ultrasound, etc., as would be known by those skilled in the art.

Pharmaceutical Packages and Kits

The present invention also provides pharmaceutical packages and kits comprising one or more containers comprising one or more doses of the antibody or the antigen binding portion thereof. In some embodiments, a unit dose is provided wherein the unit dose contains a predetermined amount of a composition comprising, for example, the antibody or the antigen binding portion thereof, with or without one or more additional agents. For other embodiments, such a unit dose is supplied in single-use prefilled syringe for injection. In other embodiments, the composition contained in the unit dose may comprise saline, sucrose, or the like; a buffer, such as phosphate, or the like; and/or be formulated within a stable and effective pH range. Alternatively, in some embodiments, the composition is a conjugate composition, which may be provided as a lyophilized powder that may be reconstituted upon addition of an appropriate liquid, for example, sterile water or saline solution. Any label on, or associated with, the containers indicates that the enclosed conjugate composition is used for treating the tumor disease condition of choice. In some preferred embodiments, the composition comprises one or more substances that inhibit protein aggregation, including, but not limited to, sucrose and arginine.

The present invention also provides kits for producing single-dose or multi-dose administration units of site-specific conjugates and, optionally, one or more anti-cancer agents. The kits comprise containers and labels or package inserts on or associated with the containers. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments, the containers comprise a sterile access port (for example the container may be an intravenous solution bag or a vial having a stopper pierceable by a hypodermic injection needle). Such kits generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody or the antigen binding portion thereof of the present invention, such kits may contain any one or more of anti-cancer agents such as chemotherapeutic agents or radiotherapeutic agents; anti-angiogenic agents; anti-metastatic agents; targeted anti-cancer agents; cytotoxic agents; and/or other anti-cancer agents.

More specifically, the kits may have a single container that contains the disclosed antibody or the antigen binding portion thereof, with or without additional components, or they may have distinct containers for each desired agent. Where combined therapeutic agents are provided for conjugation, the therapeutic agents may be pre-mixed into a single solution, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and glucose solution.

When the components of the kits are provided in one or more liquid solutions, the liquid solution is preferably an aqueous solution, with a sterile aqueous solution or saline solution being particularly preferred. However, the components of the kits may be provided as a dry powder. When reagents or components are provided as a dry powder, the powder can be reconstituted by the addition of a suitable solvent. It is envisioned that the solvent may also be provided in another container.

As indicated briefly above, the kits may also contain a means by which the antibody or the antigen binding portion thereof and any optional components are administered to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other components in close confinement for commercial sale, such as, injection or blow-molded plastic containers into which the desired vials and other apparatus are placed and retained.

Advantages of the Present Invention

Development of antibodies against CLDN18.2 has at least the following advantages:

first, human CLDN18.2 is highly expressed in cancer cells, for the normals cell, it specifically expressed in gastric epithelial cells. Therefore, the toxicity and side effects are expected to be lower, and the druggability is expected to be higher;

Second, CLDN18.2 is expressed in the tight junctions of gastric epithelial cells, which are less easily accessible to antibodies as compared to the relatively loose cancer cells; and even if epithelial cells are killed by the antibodies, stem cells beneath the epithelial cells, which do not express CLDN18.2, can restore damaged gastric epithelial cells by differentiation;

Third, not only can the antibodies against CLDN18.2 kill cells via ADCC and CDC but also mediate apoptosis by the cross-linking of antibodies with CLDN18.2, and the antibodies can inhibit cell proliferation to a certain extent.

So far, there is no nanobody against CLND18.2 yet. Caplacizumab, a nanobody (as a novel antibody format), has been approved, which sufficiently verifies the druggability of nanobodies. Nanobody, relative to other antibody type, has outstanding advantages, such as adjustable half-life achieved by chemical modification or protein fusion and engineering, strong penetration, recognition of hidden epitopes unaccessible to common antibodies, pepsin tolerance, acid resistance, heat resistance, easy production, and easy assembling into bivalent antibodies and multivalent antibodies with other types of antibodies due to its nature as a single chain.

In a part of the embodiments in the present invention, the antibody against CLDN18.2 is obtained by screening in an alpaca derived immunization phage display antibody library. On this basis, on its C-terminus, the obtained antibody is fused with the Fc fragment of IgG1. At present, a part of the candidate antibodies show better or at least comparable activity compared to the control antibody according to the results from the CDC and ADCC experiments at the cellular level. In combination with the property of the CLDN18.2 target, the single domain antibody developed, when used for cancer immunotherapy, has lower toxicity, side effects and better clinical efficacy. It will provide patients with more drug options.

EXAMPLES

The present invention, thus generally described, will be understood more readily by reference to the following Examples, which are provided by way of illustration and are not intended to be limiting of the present invention. The Examples are not intended to represent that the experiments below are all or the only experiments performed.

Example 1

Construction and identification of overexpression cell lines and tumor cell lines In this example, different types of overexpression cell lines and tumor cell lines were constructed, respectively and identified by flow cytometry.

1. Construction and Identification of Overexpression Cell Lines

The nucleic acid sequences of full-length human CLDN18.1 (SEQ ID NO: 16), mouse CLDN18.2 (SEQ ID NO: 17), and mouse CLDN18.1 (SEQ ID NO: 18) were constructed into pLVX-puro plasmids (Clontech, Cat #632164). Then the resulting plasmids were transformed into HEK293 cells (ATCC® CRL-1573™) via electrotransformation. The cell line overexpressing full-length human CLDN18.1 (human CLDN18.1-HEK293), mouse CLDN18.2 (mouse CLDN18.2-HEK293) or mouse CLDN18.1 (mouse CLDN18.1-HEK293) were obtained by screening. Subsequently, the flow cytometry identification was performed via the IMAB362 antibody (obtained by expressing and purifying according to the sequence information disclosed in the patent US20180127489 A1) and the anti-CLDN18 antibody [34H14L15] (Abcam, ab203563) that recognizes the C-terminal intracellular segment of CLDN18 (GFKASTGFGSNTKN, SEQ ID NO: 21), and overexpression cell lines were successfully obtained, and the specific method is as follows.

1.1 Electrotransformation

First, HEK293 cells were recovered and cultured and serially passaged 2-3 times. One day prior to transfection, the cells were plated at a density of $3\times10^5$ per mL in a cell culture dish and could be used on the following day when the cell confluence reached about 70%. The cells were collected after digestion with Trypsin containing 0.25% by volume of EDTA (Gibco, 25200-072) for 2 min. Cells were then centrifuged at 100 g at room temperature for 5 min, and the supernatant was discarded, after which 1×DPBS (Shanghai BasalMedia Technologies Co., LTD., B210) was added and the cells were resuspended and counted. $5\times10^6$ cells were taken, centrifuged and collected. The cells were resuspended with 250 μL Buffer R (Invitrogen, Neon™ Kit, PK10096), to which 25 μg plasmids of interest were then added, followed by gentle mixing with a pipettor to uniformity. Then, the suspension was placed in an electrotransformation apparatus (Invitrogen, Neon™ Transfection System, MP922947) for electrotransformation, and the reaction conditions were set at 1100 V/20 ms/2 electrotransformations.

1.2 Cell Culture

After electrotransformation, the cells thus obtained were transferred to antibiotics-free DMEM media (Gibco, 11995065) containing 10% by volume of FBS (Gibco, 15140-141), respectively. Subsequently, the cells were plated into a 10 cm×10 cm cell culture dish and cultured for 48 h, and then the cells were plated at a density of 0.5 cells/well on average to a 96-well cell culture plate. Puromycin (Gibco, A111138-03) was added at a final concentration of 2 μg/mL as the screening pressure. After around 2 weeks, the growth of cell line clones was observed, and the cloned cell lines were picked and identified.

1.3 Flow Cytometry Identification of Overexpression Cell Lines

The cell lines obtained in section 1.2 above were identified by flow cytometry, and the specific method was as follows.

1.3.1 Flow Cytometry Identification of Human CLDN18.2-HEK293T and Mouse CLDN18.2-HEK293 Cell Lines For human CLDN18.2-HEK293T (KYinno Biotechnology Co., Ltd., KC-0986) and mouse CLDN18.2-HEK293 cell lines, IMAB362 antibodies were directly used for identification.

$1×10^5$ cells were taken and centrifuged at a low speed (300 g), and the supernatant was removed. The cells at the bottom of the centrifuge tube were rinsed once with a formulated FACS buffer (a 1×PBS buffer containing 2% by volume of FBS). Subsequently, 12.5 μg/mL of the antibody IMAB362 was added to the rinsed cells, which were then incubated at 4° C. for 1 h and then rinsed with the FACS buffer for three times. 0.5 μg of PE-labeled goat anti-human IgG Fc antibodies (Abcam, ab98596) were added, followed by an incubation at 4° C. for 1 h. Subsequently, the cultures were rinsed with the FACS buffer for three times, and then 200 μL FACS buffer was added to the cells and the cells were resuspended, and finally, the cells were detected by a flow cytometry (Beckman, CytoFLEX AOO-1-1102).

1.3.2 Flow Cytometry Identification of Human CLDN18.1-HEK293 and Mouse CLDN18.1-HEK293 Cell Lines Since IMAB362 antibody only recognized CLDN18.2 but did not recognize CLDN18.1, human CLDN18.1-HEK293 and mouse CLDN18.1-HEK293 cell lines needed to be identified in conjunction with other methods. Considering the sequence identity of human CLDN18.1 and mouse CLDN18.1, the cells were first fixed and permeabilized according to the method in the instruction of a cell permeabilization kit (eBioscience, 88-8824-00), and then a flow cytometry identification was performed by the anti-CLDN18 antibody [34H14L15] recognizing the C-terminal intracellular segment of CLDN18 and IMAB362 antibody which specifically recognizes CLDN18.2.

The specific method is as follows: $1×10^5$ cells were taken and centrifuged at a low speed (300 g), and the supernatant was removed. The cells at the bottom of the centrifuge tube were rinsed once with the FACS buffer, and then 200 μL IC fixation buffer (eBioscience, 00-8222) was added to the rinsed cells. The cells were incubated at 4° C. for 1 h and then rinsed twice with a permeabilization buffer (eBioscience, 00-8333), which was followed by the addition of the anti-CLDN18 antibody above and an incubation at 4° C. for 1 h. The cells were then rinsed with the permeabilization buffer above for three times, then 0.5 μg of Alexa Fluor® 488 fluorescently labeled donkey anti-rabbit IgG H & L (abcam, ab150073) was added and incubated at 4° C. for 1 h, and finally, the cells were detected by flow cytometry (Beckman, CytoFLEX AOO-1-1102).

In addition, the binding of IMAB362 to human CLDN18.1-HEK293 and mouse CLDN18.1-HEK293 cell lines was determined by using the method as described in 1.3.1 above.

Figure 1A:
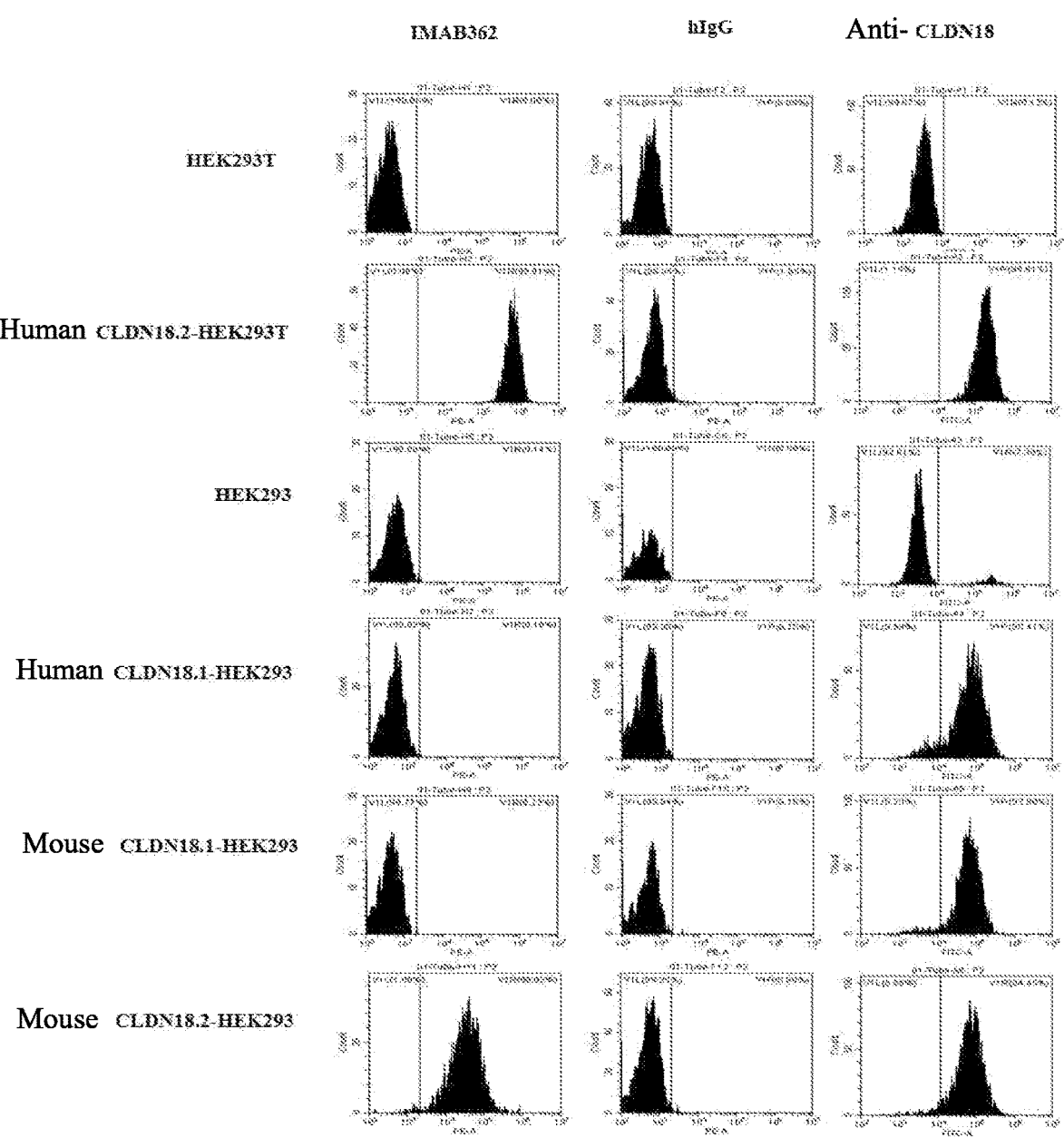
FIGS. 1a and 1b show the flow cytometry identification results of overexpression cell lines and tumor cell lines in Example 1.

The results of flow cytometry identification are as shown in FIG. 1a. It shows that. the anti-CLDN18 antibody could recognize human CLDN18.2-HEK293T, human CLDN18.1-HEK293, mouse CLDN18.2-HEK293, mouse CLDN18.1-HEK293 other than HEK293 and HEK293T cells; and the antibody IMAB362 only recognized mouse CLDN18.2-HEK293 and human CLDN18.2-HEK293T, but did not recognize mouse CLDN18.1-HEK293 and human CLDN18.1-HEK293. This illustrated that the four cell lines of human CLDN18.2-HEK293T, human CLDN18.1-HEK293, mouse CLDN18.2-HEK293, and mouse CLDN18.1-HEK293 all successfully expressed the corresponding CLDN18 proteins.

2. Construction and Identification of Overexpression Tumor Cell Lines

The gastric cancer cell line KATOIII overexpressing human CLDN18.2 (human CLDN18.2-KATOIII tumor cell line) was constructed by using the means of lentivirus transfection and identified with the antibody IMAB362. The specific method is as follows:

$5×10^4$ well-conditioned human gastric cancer cells KATOIII (ATCC® HTB-103™) were taken, then packaged lentiviruses containing human CLDN18.2 sequences (SEQ ID NO: 15) were added at the MOI ratio of 30:1 and fully mixed to uniformity. Subsequently, an IMDM complete medium (Gibco, 12440061) containing 8 μg/mL polybrene (Sigma, 107689) was added and mixed to uniformity and incubated in a constant temperature incubator at 37° C. with 5% $CO_2$ for 20 h. Then, the medium was removed and a fresh IMDM complete medium was added for an incubation for another 24 h. Subsequently, the transfected KATOIII cells were plated at a density of 0.5 cells/well on average to a 96-well plate, and puromycin was added at a final concentration of 2 μg/mL for screening by antibiotic stress and cultured in a constant temperature incubator at 37° C. with 5% $CO_2$ for 2-3 weeks, and then clones were picked for identification.

The cell lines obtained through antibiotic screening were identified with the antibody IMAB362 by using flow cytometry according to the same method as described in section 1.3.1 above.

Figure 1B:
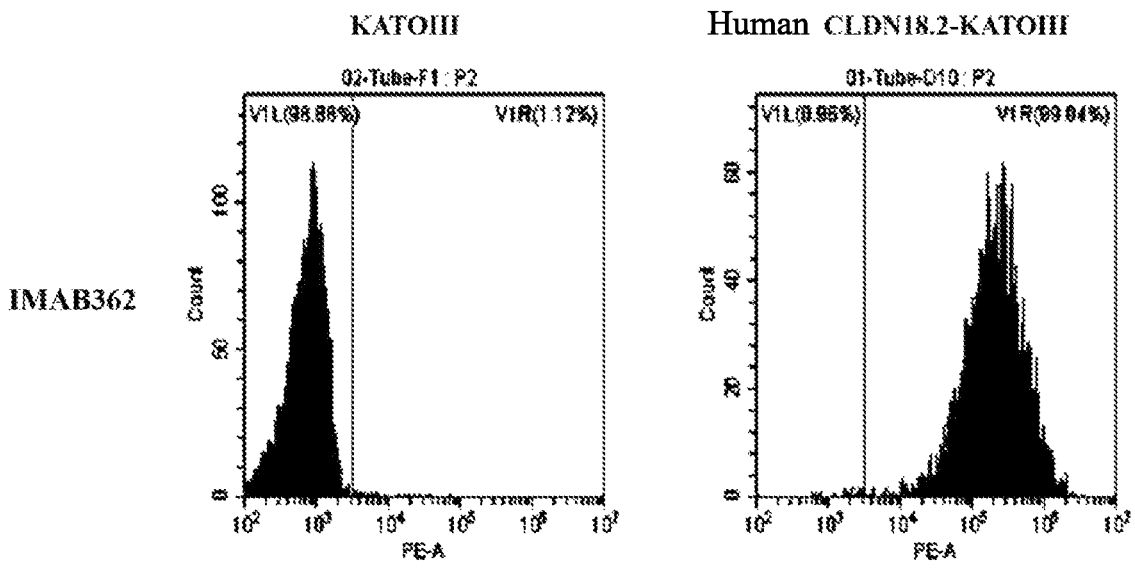

The results of flow cytometry identification are as shown in FIG. 1b. It could be seen from FIG. 1b that KATOIII cells not transfected with CLDN18.2 were barely recognized by the antibody IMAB362, which illustrated that almost no CLDN18.2 or only a very small amount of CLDN18.2 was expressed on KATOIII cell line; And human CLDN18.2-KATOIII tumor cell line successfully constructed by transfection with lentiviruses could be recognized by the antibody IMAB362, which illustrated that this cell line was successfully constructed.

Example 2

Animal Immunization and Immune Titer Detection in Serum

1. Immunization

In this example, alpaca immunization was used. The specific operations are as follows: The cell line, human CLDN18.2-HEK293T (KYinno, KC-0986) and hCLDN18.2-pLVX-puro plasmids containing human CLDN18.2 ECD1 (SEQ ID NO: 19) were used as the immunogens. $2 \times 10^7$ of the human CLDN18.2-HEK293T cells (subcutaneous injection at multiple sites) and 2 mg of the plasmids (intramuscular injection at multiple sites) were alternately used to immunize an alpaca (Nanchang Dajia technology co., Ltd., alpaca code: NSY002) on a weekly basis, respectively, for 8 immunizations in total. Finally, $2 \times 10^7$ human CLDN18.2-HEK293T cells were used for the boosting immunization.

2. Immune Titer Determination in Serum

Immune titer determination was performed by the ELISA method based on the signal of the immune serum against the recombinant protein CLDN18.2 (Genscript Biotech Corporation, CP0007). The specific method is as follows.

One day prior to the immune titer determination, the recombinant protein CLDN18.2 was diluted with PBS to 1 μg/mL, thereby obtaining a diluent. 30 μL of the diluent was added to an Elisa plate, which was coated overnight at 4° C. During the day of immune titer determination, the coated plate was rinsed twice with PBS and then blocked with PBST containing 5% by volume of skim milk powder for two hours and subsequently rinsed twice with PBS. In a different 96-well plate for dilution, the un-immunized negative serum and immunized serum were diluted with PBS, with 1000-fold dilution for the first well and a 2-fold gradient dilution for the following 7 wells. The diluted sera were correspondingly added to the first Elisa plate coated with the recombinant CLDN18.2 and incubated at 37° C. for 1 h, which was followed by washing twice with PBS. Subsequently, a secondary antibody MonoRab™ rabbit anti-Camelidae VHH antibody (Genscript, A01862-200) was added at 1:5000 dilution and finally, OD values were read at the wavelength of 450 nm by using a microplate reader (Molecular Devices, SpecterMax 190). As shown from the results in table 1, the titer of alpaca immunization was approximately 1:8000.

TABLE 1

| Serum dilution ratio | OD$_{450}$ Value | |
| | Negative alpaca serum | Serum of immunized alpaca NSY002 |
| --- | --- | --- |
| 1:1000 | 0.045 | 0.5618 |
| 1:2000 | 0.0457 | 0.2796 |
| 1:4000 | 0.0452 | 0.1471 |
| 1:8000 | 0.0458 | 0.1028 |
| 1:16000 | 0.0454 | 0.0694 |
| 1:32000 | 0.0459 | 0.0616 |
| 1:64000 | 0.045 | 0.0574 |
| 1:128000 | 0.0453 | 0.0501 |

Example 3

Construction and Screening of Alpaca Immune Library

After the completion of the animal immunization, 80 mL blood was sampled from the alpaca, and PBMC was isolated with a Ficoll-Paque density gradient medium (GE, 17144003S) for construction of the alpaca immune library. The specific method is as follows:

15 mL of the Ficoll-Paque density gradient medium was taken and slowly added to a 50 mL centrifuge tube, and then 15 mL of the alpaca blood sampled was added slowly, so that the two liquids maintained a clear separation interface. Centrifugation was carried out at about 15° C. under the following conditions: 400 g, 20 min, acceleration: 3, and deceleration: 0. After centrifugation, the entire liquid was divided into four layers, with the top layer being a plasma mixture, the bottom layer being red blood cells and granulocytes, the middle layer being Ficoll-Paque liquid, and the junction of the top and middle layers being a narrow zone of white misty layer mainly composed of PBMC, i.e., a PBMC cell layer. Firstly, a sterile Pasteur pipette was used to carefully pipette and remove the plasma mixture in the top layer, and then a new sterile Pasteur pipette was used to pipette the PBMCs, thereby obtaining isolated PBMCs. The isolated PBMCs were rinsed twice with PBS and horizontally centrifuged at 4° C., 1500 rpm for 10 min and finally resuspended with 1.5 mL PBS and counted by a cell counter (CountStar, CountStar Altair).

RNAs were drawn from the isolated PBMCs and reverse transcribed into cDNAs by a Reverse Transcription Kit (TaKaRa, 6210A). As the molecular form of an alpaca antibody has no light chain and has a heavy chain without CHI, which is different from that of a common antibody. Therefore, two fragments of different sizes were obtained by PCR using primers designing in front of the VH germline gene and in the CH2, and the smaller fragment of interest was recovered by gel extraction. Degenerate primers containing NcoI and NotI restriction sites were designed by aligning all the sequences of all V and J genes of the VHH antibodies, and then all the VHH genes were amplified by using the DNA fragment product recovered as the template. Finally, the gene fragment of the antibody of interest was inserted into the vector for phage display by double digestion and ligation, with the GIII gene being fused at the C-terminus of the VHH. The ligation product was recovered by a recovery kit (Omega, D6492-02) and finally transformed into competent E. coli SS320 (Lucigen, MC1061 F) by an electrotransformation apparatus (Bio-Rad, MicroPulser), the transformed E. coli SS320 were plated onto a 2-YT solid plate with ampicillin antibiotic (prepared with 1.5% tryptone, 1% yeast extract, 0.5% NaCl, and 1.5% agar by mass/volume (g/mL)). To calculate the library size, the clones formed on the plate from 1 μL bacterial solution after dilution were used to calculate the total number of all the clones formed by electrotransformation, thereby obtaining the library size. The library size of this immune library was $1 \times 10^9$ cfu.

Based on the library size, 50 ODs (1 OD=$5 \times 10^8$ cfu) of alpaca library bacteria were picked and added to a fresh 2-YT liquid medium, so that the initial OD value was 0.05. Cultures were placed at 37° C., 220 rpm and cultured to the log growth phase, and at this time VSCM13 helper phages in an amount 5 times the number of the bacteria were added and fully mixed to uniformity and allowed to stand for 30 min and then cultured at 220 rpm for 1 h, and then the obtained cultures were centrifuged at 10000 rpm for 5 min and had the medium changed to a C+/K+2-YT medium following discarding the supernatant and cultured at 30° C., 220 rpm overnight. On the following day, the resulting cultures were centrifuged at 13000 g for 10 min, and the phage corresponding to the alpaca library in the supernatant was precipitated by adding 20% PEG/NaCl (prepared with 20% PEG6000 and 2.5 M NaCl by volume concentration). The phage were used for phage screening following rinsing with PBS once.

Antibodies against human CLDN18.2 were screened from the phage displaying library by using the method of cell screening, with the human CLDN18.2-HEK293T cell lines as the screening antigens. The specific method was described as follows. Human CLDN18.2-HEK293T or human CLDN18.1-HEK293 was cultured in a T25 square culture flask. When the cultures were grown to a density of about 90% (with the optimal growth by then), the cultural supernatant was removed, and the cultures were rinsed with PBS (BasalMedia, B310KJ) once. Subsequently, 5 mL of 4% paraformaldehyde (Sangon Biotech (Shanghai) Co., Ltd., E672002-0500) was added for fixation for 1 h. Finally, the obtained cultures, after being rinsed twice with PBS, could be used as antigen materials for cell screening of phages. During screening, the phages corresponding to the alpaca library were first incubated with the fixed human CLDN18.1-HEK293 cell at room temperature for 1 h. Then, the phages in the supernatant were pipetted after adsorption and incubated with fixed human CLDN18.2-HEK293T cells for 2 h. After the cultures were rinsed twice with PBS, 3 mL of glycine-HCl (pH 2.0) was added and gently mixed to uniformity for 10 min in order to elute the phages that specifically binded to the target membrane protein CLDN18.2. Then the eluted supernatant was used to infect log phase SS320 bacterial cells (Lucigen, 60512-1) and allowed to stand for 30 min, and cultured at 220 rpm for 1 h. Subsequently, VSCM13 helper phages were added, allowed to stand for 30 min and then cultured at 220 rpm for 1 h, and then the obtained cultures were centrifuged and had the medium changed to a C/K 2-YT medium. The resulting phages were used for a second round of screening. The procedures were repeated as such and sequence analysis was performed on 10 clones randomly selected in each round. The results showed that after 3 rounds of screening, sequence enrichment was obvious after the third round of screening.

The clones of the third round of screening were picked and used to prepare a phage supernatant in a 96-well plate. Positive clones against CLDN18.2 recombinant protein were screened by phage ELISA, and then all the positive clones were picked for sequencing analysis. Subsequently, for the clone with the unique sequence, the phage supernatant was prepared and further verified at the level detected by flow cytometry, thereby obtaining candidate antibodies that specifically bind to human CLDN18.2 but not human CLDN18.1.

The specific method for verifying at the level detected by flow cytometry is as follows:

firstly, $1 \times 10^5$ of human CLDN18.2-HEK293T and human CLDN18.1-HEK293 cells were taken, respectively and centrifuged at a low speed of 500 g, and the supernatant was removed. After the cells were rinsed with the FACS buffer as described in 1.3.1, phages blocked with 10% FBS (Gibco, 15140-141) for 1 h were added and incubated at 4° C. for 1 h, and then rinsed twice with the FACS buffer and incubated at 4° C. for another 1 h following the addition of anti-M13 mouse monoclonal antibodies (Sino Biological, 11973-MM05T) at 1:50. Subsequently, the resulting cultures were rinsed twice with the FACS buffer and incubated at 4° C. for 1 h following the addition of a secondary antibody, APC-labeled anti-mouse Fc antibody (Jackson, 115136071). The obtained cultures were then rinsed twice with the FACS buffer and finally detected by a flow cytometry (Beckman, CytoFLEX AOO-1-1102).

The specific results are as shown in table 2 below:

TABLE 2

| Clone number | Mean fluorescence intensity for phages binding on hCLDN18.1-HEK293T cells | Mean fluorescence intensity for phages binding on hCLDN18.2-HEK293 cells | Ratio of mean fluorescence intensities of phages binding on hCLDN18.2-HEK293 and hCLDN18.1-HEK293T cells |
|---|---|---|---|
| A-2-4 | 4328 | 592000 | 137 |
| A18-1-50 | 6041 | 403000 | 67 |
| A18-1-70 | 6231 | 402000 | 65 |
| A18-1-64 | 3496 | 406000 | 116 |
| A18-1-78 | 3683 | 385000 | 105 |
| A18-1-48 | 3453 | 357000 | 103 |
| A293-82 | 4321 | 442000 | 102 |
| A18-1-75 | 3891 | 387000 | 99 |
| A18-1-6 | 1972 | 396000 | 201 |
| A18-1-44 | 3739 | 390000 | 104 |
| A18-1-62 | 2941 | 372000 | 126 |
| A18-1-45 | 4753 | 369000 | 78 |
| A-2-3 | 3255 | 570000 | 175 |
| A18-1-63 | 175 | 385000 | 2200 |
| A18-1-65 | 5894 | 428000 | 73 |
| A18-1-42 | 1010 | 396000 | 392 |
| A293-55 | 3344 | 392000 | 117 |
| A293-34 | 2434 | 454000 | 187 |

The above results indicated that the antibodies of the present disclosure could all specifically bind to human CLDN18.2.

The corresponding candidate antibodies were named after the clone number, respectively. Amino acid sequence of each candidate antibody is as shown in tables 3 and 4 below.

TABLE 3

CDR sequences of some of the exemplary antibodies (candidate antibodies) of the present disclosure

| Candidate Antibodies | CDR1 | | CDR2 | | CDR3 | |
|---|---|---|---|---|---|---|
| | SEQ ID NO. | Sequence | SEQ ID NO. | Sequence | SEQ ID NO. | Sequence |
| A-2-4 | 1 | GNIFRIDT | 2 | ISRGGTT | 3 | NAQAWDPGTFRYLEV |
| A18-1-50 | 1 | GNIFRIDT | 2 | ISRGGTT | 3 | NAQAWDPGTFRYLEV |
| A18-1-70 | 1 | GNIFRIDT | 2 | ISRGGTT | 3 | NAQAWDPGTFRYLEV |
| A18-1-64 | 1 | GNIFRIDT | 4 | ISRGGST | 5 | NAQAWDPGTIRYLEV |
| A18-1-78 | 1 | GNIFRIDT | 4 | ISRGGST | 5 | NAQAWDPGTIRYLEV |
| A18-1-48 | 1 | GNIFRIDT | 4 | ISRGGST | 5 | NAQAWDPGTIRYLEV |
| A293-82 | 1 | GNIFRIDT | 2 | ISRGGTT | 6 | NAQAWDVGTIRYLEV |
| A18-1-75 | 1 | GNIFRIDT | 2 | ISRGGTT | 6 | NAQAWDVGTIRYLEV |
| A18-1-6 | 30 | GSIFNIPV | 31 | ISTGGTT | 37 | NVLVISGIGSHLEV |
| A18-1-44 | 33 | GSIFNLPV | 31 | ISTGGTT | 37 | NVLVISGIGSHLEV |
| A18-1-62 | 34 | GTIFNIPV | 31 | ISTGGTT | 37 | NVLVISGIGSHLEV |
| A18-1-45 | 35 | GIIFNIPV | 31 | ISTGGTT | 62 | NVLVVSGIGSHLEV |
| A-2-3 | 33 | GSIFNLPV | 31 | ISTGGTT | 62 | NVLVVSGIGSHLEV |
| A18-1-63 | 30 | GSIFNIPV | 31 | ISTGGTT | 32 | NVLVVSGIGSTLEV |
| A18-1-65 | 36 | GTIFNLPV | 31 | ISTGGTT | 62 | NVLVVSGIGSHLEV |
| A18-1-42 | 38 | GSILHIPV | 31 | ISTGGTT | 62 | NVLVVSGIGSHLEV |
| A293-55 | 39 | GSIFHIVV | 41 | MSTGGTT | 37 | NVLVISGIGSHLEV |
| A293-34 | 40 | GTFFNIPV | 31 | ISTGGTT | 37 | NVLVISGIGSHLEV |

TABLE 4

Variable region sequences of some of the exemplary antibodies (candidate antibodies) of the present disclosure

| Candidate antibodies | Variable regions | |
|---|---|---|
| | Amino acid sequences | Nucleotide sequences |
| A-2-4 | EVQVQESGGGLVQAGTSLRLSCAASGNIFRIDTMGWYRQAPG KQRELVAGISRGGTTTYAHSVKERFTISRDNAKNTMYLQMNS LKSEDTAGYYCNAQAWDPGTFRYLEVWGQGTLVTVSA (SEQ ID NO: 7) | SEQ ID NO: 22 |
| A18-1-50 | EVQVQESGGGLVQPGGSLRLSCAASGNIFRIDTMGWYRQAPG KQRELVAGISRGGTTTYAHSVKERFTISRDNAKNTMYLQMNS LKSEDTAGYYCNAQAWDPGTFRYLEVWGQGTLVTVSA (SEQ ID NO: 8) | SEQ ID NO: 24 |
| A18-1-70 | QVQLVESGGGLVQPGGSLRLSCAASGNIFRIDTMGWYRQAPG KQRELVAGISRGGTTTYAHSVKERFTISRDNAKNTMYLQMNS LKSEDTAGYYCNAQAWDPGTFRYLEVWGQGTLVTVSA (SEQ ID NO: 9) | SEQ ID NO: 26 |

TABLE 4-continued

Variable region sequences of some of the exemplary antibodies
(candidate antibodies) of the present disclosure

| | Variable regions | |
|---|---|---|
| Candidate antibodies | Amino acid sequences | Nucleotide sequences |
| A18-1-64 | QVQLVESGGGLVQPGGSLRLSCAASGNIFRIDTMGWYRQAPG KQREFVAGISRGGSTNYAHSVKERFTISRDNAKNTMYLQMNS LKSEDTAGYYCNAQAWDPGTIRYLEVWGQGTLVTVSS (SEQ ID NO: 10) | SEQ ID NO: 25 |
| A18-1-78 | EVQLQESGGGLVQPGGSLRLSCAASGNIFRIDTMGWYRQAPG KQREFVAGISRGGSTNYAHSVKERFTISRDNAKNTMYLQMNS LKSEDTAGYYCNAQAWDPGTIRYLEVWGQGTLVTVSA (SEQ ID NO: 11) | SEQ ID NO: 28 |
| A18-1-48 | EVQLVESGGGLVQPGGSLRLSCAASGNIFRIDTMGWYRQAPG KQREFVAGISRGGSTNYAHSVKERFTISRDNAKNTMYLQMNS LKSEDTAGYYCNAQAWDPGTIRYLEVWGQGTLVTVSA (SEQ ID NO: 12) | SEQ ID NO: 23 |
| A293-82 | EVQVVESGGGLVQPGGSLRLSCAASGNIFRIDTMVWYRQAPG KQRELVAGISRGGTTNYAHSVKGRFTISRDNAKNTMYLQMNS LKSEDTATYYCNAQAWDVGTIRYLEVWGQGTLVTVSA (SEQ ID NO: 13) | SEQ ID NO: 29 |
| A18-1-75 | EVQLVESGGGLVQPGGSLRLSCAASGNIFRIDTMVWYRQAPG KQRELVAGISRGGTTNYAHSVKGRFTISRDNAKNTMYLQMNS LKSEDTATYYCNAQAWDVGTIRYLEVWGQGTLVTVSA (SEQ ID NO: 14) | SEQ ID NO: 27 |
| A18-1-6 | EVQVQESGGGLVQPGGSLRLSCAASGSIFNIPVMSWYRQAPG KQRELVAGISTGGTTNYGDSVKGRFTISRDNAKTTVYLQMNS LKPEDTAVYYCNVLVISGIGSHLEVWGQGTLVTVS (SEQ ID NO: 42) | SEQ ID NO: 56 |
| A18-1-44 | EVQLVESGGGLVQPGGSLRLSCAASGSIFNLPVMSWYRQAPG KQRELVAGISTGGTTNYGDSVKGRFTISRDNAKNTVYLQMNS LKPEDTAVYYCNVLVISGIGSHLEVWGQGTLVTVS (SEQ ID NO: 43) | SEQ ID NO: 54 |
| A18-1-62 | QVQLVESGGGLVQPGGSLRLSCAASGTIFNIPVMGWYRQAPG KQRELVAGISTGGTTNYGDSVKGRFTISRDNAKNTVYLQMNS LKPEDTAVYYCNVLVISGIGSHLEVWGQGTLVTVS (SEQ ID NO: 44) | SEQ ID NO: 57 |
| A18-1-45 | EVQLQESGGGLVQPGGSLRLSCAASGIIFNIPVMSWYRQAPGK QRELVAGISTGGTTNYGDSVKGRFTISRDNAKNTVYLQMNSL KPEDTAVYYCNVLVVSGIGSHLEVWGQGTLVTVS (SEQ ID NO: 45) | SEQ ID NO: 55 |
| A-2-3 | EVQLVESGGGLVQPGGSLRLSCAASGSIFNLPVMSWYRQAPG KQRELVAGISTGGTTNYGDSVKGRFTISRDNAKNTVYLQMNS LKPEDTAVYYCNVLVVSGIGSHLEVWGQGTLVTVS (SEQ ID NO: 46) | SEQ ID NO: 52 |
| A18-1-63 | QVQLQESGGGLVQPGGSLRLSCAASGSIFNIPVMGWYRQAPG KQRELVAGISTGGTTNYGDSVKGRFTISRDNAKNTVYLQMNS LKPEDTAVYYCNVLVVSGIGSTLEVWGQGTLVTVS (SEQ ID NO: 47) | SEQ ID NO: 58 |
| A18-1-65 | EVQLQESGGGLVQPGGSLRLSCAASGTIFNLPVMSWYRQAPG KQRELVAGISTGGTTNYGDSVKGRFTISRDNARNTVYLQMNS LKPEDTAVYYCNVLVVSGIGSHLEVWGQGTLVTVS (SEQ ID NO: 48) | SEQ ID NO: 59 |
| A18-1-42 | EVQVVESGGGLVQPGGSLRLSCAASGSILHIPVMSWYRQAPG KQRELVAGISTGGTTNYGDSVKGRFTISRDNAKNTVYLQMNS LKPEDTAAYYCNVLVVSGIGSHLEVWGQGTLVTVSS (SEQ ID NO: 49) | SEQ ID NO: 53 |
| A293-55 | QVQLVESGGGSVQPGGSLRLSCAASGSIFHIVVMGWYRQAPG KQRELVAGMSTGGTTNYGDSVKGRFTISRDNAKNTVYLQMN SLKPEDTAVYYCNVLVISGIGSHLEVWGQGTLVTVS (SEQ ID NO: 50) | SEQ ID NO: 61 |

TABLE 4-continued

| Variable region sequences of some of the exemplary antibodies (candidate antibodies) of the present disclosure | | |
|---|---|---|
| | Variable regions | |
| Candidate antibodies | Amino acid sequences | Nucleotide sequences |
| A293-34 | QVQLQESGGGLVQPGGSLRLSCAASGTFFNIPVMGWYRQAPG KQRELVAGISTGGTTNYGDSVKGRFTISRDNAKNTVYLQMNS LKPEDTAVYYCNVLVISGIGSHLEVWGQGTLVTVS (SEQ ID NO: 51) | SEQ ID NO: 60 |

Figure 2A:
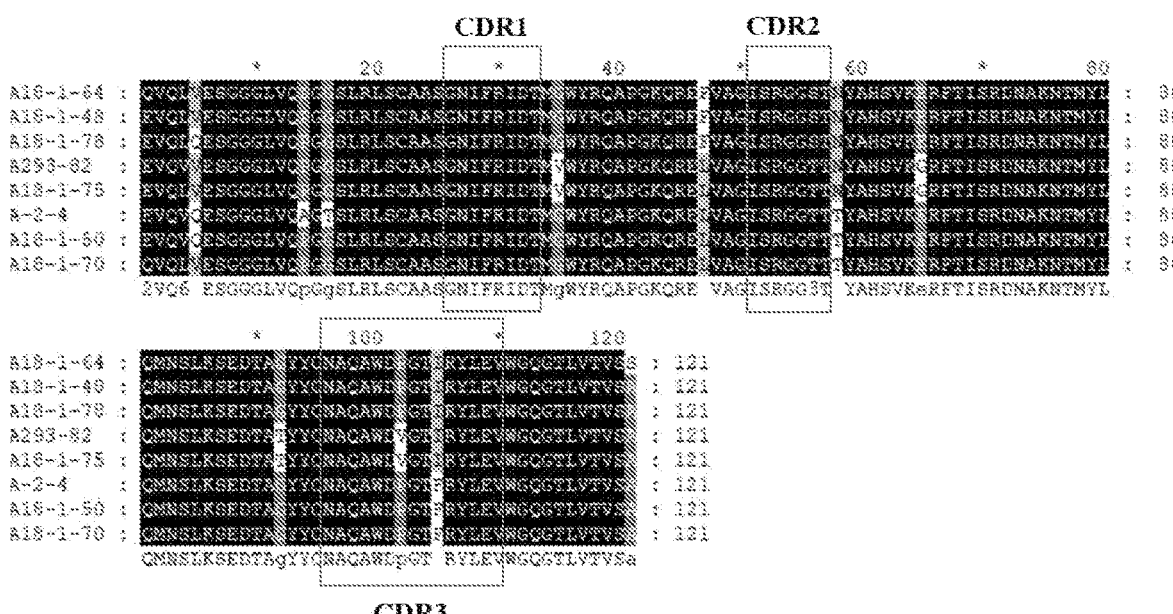
FIGS. 2a and 2b show the sequence comparison of a plurality of candidate antibodies, wherein the full-length sequences of the variable regions in the candidate antibodies and the CDR sequences thereof are shown, and the difference between the amino acid sequences of the candidate antibodies is indicated.
Figure 2B:
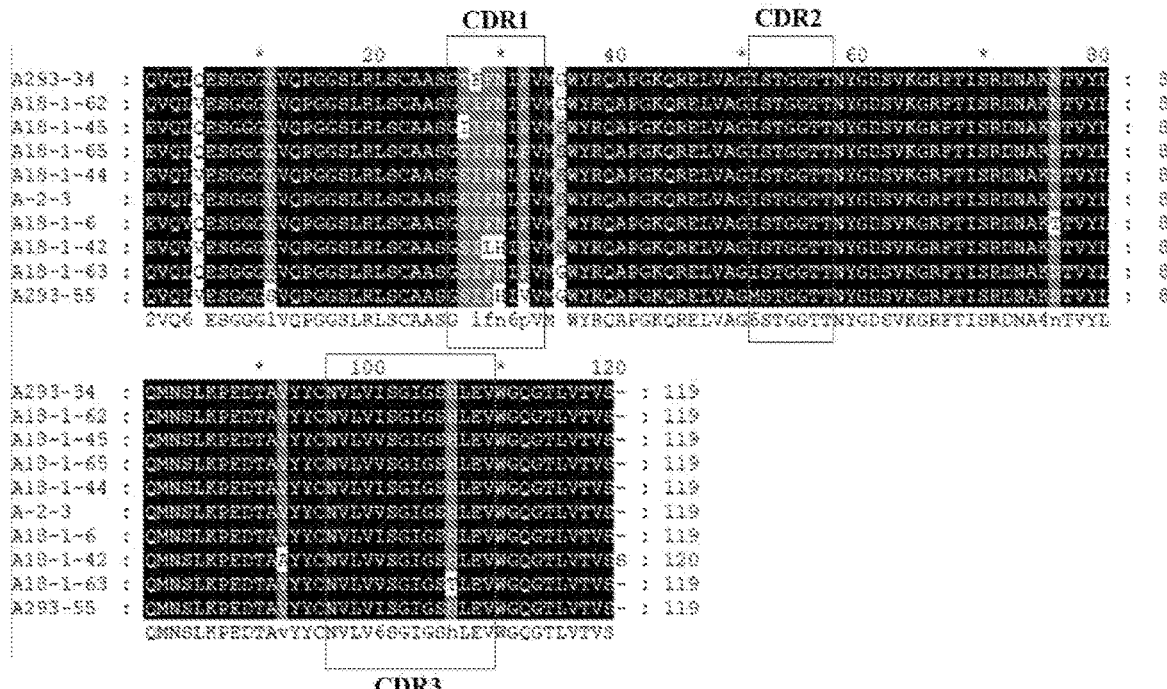

Amino acid sequences of multiple candidate antibodies obtained by screening were compared, and the results thereof are as shown in FIG. 2.

Identity comparison between variable region amino acid sequences of each candidate antibody is as shown in tables 5-1 and 5-2 below.

VKFNWYVDGVEVHNAKTKPREEQYN-STYRVVSVLTVLHQDWLNGKEYKCKVSNK ALPA-PIEKTISKAKGQPREPQVYTLPPSRDELTKNQVSLT-CLVKGFYPSDIAVEWESN GQPENNYKTTPPVLDSDGSFFLYSK-LTVDKSRWQQGNVFSCSVMHEALHNHYTQKS LSL-

TABLE 5-1

| Antibody similarity | A18-1-48 | A293-82 | A-2-4 | A18-1-70 | A18-1-64 | A18-1-78 | A18-1-75 | A18-1-50 |
|---|---|---|---|---|---|---|---|---|
| A18-1-48 | 100% | 98% | 97% | 92% | 93% | 91% | 93% | 95% |
| A293-82 | | 100% | 99% | 94% | 95% | 93% | 95% | 95% |
| A-2-4 | | | 100% | 93% | 94% | 94% | 95% | 95% |
| A18-1-70 | | | | 100% | 99% | 92% | 94% | 93% |
| A18-1-64 | | | | | 100% | 91% | 93% | 94% |
| A18-1-78 | | | | | | 100% | 98% | 95% |
| A18-1-75 | | | | | | | 100% | 97% |
| A18-1-50 | | | | | | | | 100% |

TABLE 5-2

| Antibody similarity | A18-1-65 | A-2-3 | A293-34 | A18-1-63 | A293-55 | A18-1-45 | A18-1-44 | A18-1-6 | A18-1-62 | A18-1-42 |
|---|---|---|---|---|---|---|---|---|---|---|
| A18-1-65 | 100% | 91% | 91% | 93% | 89% | 91% | 93% | 93% | 92% | 91% |
| A-2-3 | | 100% | 97% | 96% | 96% | 95% | 95% | 96% | 94% | 89% |
| A293-34 | | | 100% | 96% | 94% | 94% | 94% | 94% | 92% | 88% |
| A18-1-63 | | | | 100% | 96% | 94% | 96% | 94% | 94% | 89% |
| A293-55 | | | | | 100% | 94% | 94% | 94% | 94% | 88% |
| A18-1-45 | | | | | | 100% | 98% | 96% | 90% | 89% |
| A18-1-44 | | | | | | | 100% | 96% | 92% | 91% |
| A18-1-6 | | | | | | | | 100% | 92% | 92% |
| A18-1-62 | | | | | | | | | 100% | 90% |
| A18-1-42 | | | | | | | | | | 100% |

Example 4

Generation and Expression of Chimeric VHH-Fc (hIgG1) Antibody

CLDN18.2 is highly expressed in cancer (such as gastric cancer) cells. Antibody drugs against such tumor-related targets can kill tumors by the complement dependent cytotoxicity (CDC) and antibody-dependent cell-mediated cytotoxicity (ADCC). In this example, a chimeric antibody was designed on the basis of the candidate nanobodies obtained by screening in example 3 and expressed for subsequent CDC and ADCC experiments. Considering the particularity of the target, when the candidate nanobody gene was constructed into the plasmid pcDNA3.4 for transient transfection and expression (Thermofisher, A14697), a human IgG1 Fc fragment (EPKSCDKTHTCPPCPA-PELLGGPSVFLFPPKPKDTLMISRTPE-VTCVVVDVSHEDPE SPGK, SEQ ID NO: 20) was fused to the C-terminus of the candidate nanobody. This fragment included a linker region and the constant region of IgG1 for mediating effects such as ADCC and CDC. In this example, the candidate nanobody A-2-4 was selected and on the basis of the nanobody, the human IgG1 Fc fragment was fused thereto to obtain the chimeric antibody NA1-S (also referred to as "candidate antibody NA1-S", "antibody NA1-S" or "NA1-S antibody" in the present disclosure); the candidate nanobodies A18-1-63, A18-1-42 and A293-34 were selected and on the basis of each of these nanobodies, the human IgG1 Fc fragments were fused thereto to obtain chimeric antibodies NA3-S (also referred to as "candidate antibody NA3-S", "antibody NA3-S" or "NA3-S antibody" in the present disclosure, which was the chimeric antibody obtained by fusing the candidate nanobody A18-1-63 to the human IgG1 Fc), NA5-S (also referred to as "candidate antibody NA5-S", "antibody NA5-S" or "NA5-S antibody" in the present disclosure, which was the chimeric antibody obtained by fusing the candidate nanobody A18-1-42 to the human IgG1 Fc) and NA6-S (also referred to as "candidate antibody NA6-S", "antibody NA6-S" or "NA6-S antibody" in the present disclosure, which was the chimeric antibody obtained by fusing the candidate nanobody A293-34 to the human IgG1 Fc), respectively.

Antibodies NA1-S, NA3-S, NA5-S and NA6-S were expressed by using the ExpiCHO transient transfection and expression system (Gibco, A29133), and the specific method is as follows:

during the day of transfection, the cell density was confirmed to be about $7 \times 10^6$ to $1 \times 10^7$ viable cells/mL, and cell viability >98%, by then a 25 mL of preheated fresh ExpiCHO expression medium at 37° C. was used to adjust the cells to a final concentration of $6 \times 10^6$ cells/mL; 1 mL, pre-chilled OptiPRO™ SFM at 4° C. was used to dilute the plasmids of interest (25 µg in total) and meanwhile 920 µL OptiPRO™ SFM was used to dilute 80 µL ExpiFectamine™ CHO, and subsequently, the two were mixed and stirred to uniformity by gently pipetting to prepare an ExpiFectamine™ CHO/plasmid DNA mixture, which was incubated at room temperature for 1-5 min and then transferred to a cell suspension already prepared by slowly addition and meanwhile gentle shaking of the cell suspension and finally placed in a cell culture shaker and cultured at the condition of 37° C. and 8% $CO_2$.

ExpiCHO™ Enhancer and ExpiCHO™ Feed were added within 18-22 hours after transfection, and the shake flask was placed in a shaker at the condition of 32° C. and 5% $CO_2$ for further culture. At day 5 post-transfection, an equal volume of ExpiCHO™ Feed was slowly added and meanwhile the cell suspension was gently mixed to uniformity. At days 12-15 post-transfection, the supernatant in which cell expression occurred was centrifuged at a high speed (15000 g, 10 min), and the resulting supernatant was affinity-purified with Protein A (Millipore, P2545). Subsequently, 100 mM sodium acetate (pH 3.0) was used to elute the proteins of interest followed by neutralization with 1 M Tris-HCl, and finally the resulting proteins (i.e., antibodies NA1-S, NA3-S, NA5-S or NA6-S) were transferred into the PBS buffer by means of centrifugal filter (Millipore, UFC 901096).

Example 5

Specificity and Species-Cross Binding Activity of the Candidate Antibodies

Taking the candidate antibody NA1-S as an example, 0.25% EDTA-containing Trypsin (Gibco, 25200-072) was used to digest well-grown human CLDN18.2-HEK293T, HEK293T, HEK293, human CLDN18.1-HEK293, mouse CLDN18.2-HEK293 and mouse CLDN18.1-HEK293 cells. $1 \times 10^5$ cells and 10 µg/mL of the candidate antibody NA1-S were taken and incubated for 1 h, and additionally, the hIgG1 isotype antibody was used as a control. The cultures were rinsed twice with the FACS buffer and then incubated with 0.5 µg PE-labeled goat anti-human IgG-Fc secondary antibody (Abcam, ab98596) at 4° C. for 1 h. Subsequently, the resulting cultures were washed three times with the FACS buffer, and the binding of the candidate antibody on the cells was detected by a flow cytometry (Beckman, CytoFLEX AOO-1-1102). Specific binding and cross-specificity between species for candidate antibodies NA3-S, NA5-S and NA6-S were determined by using the same method as NA1-S.

Figure 3A:
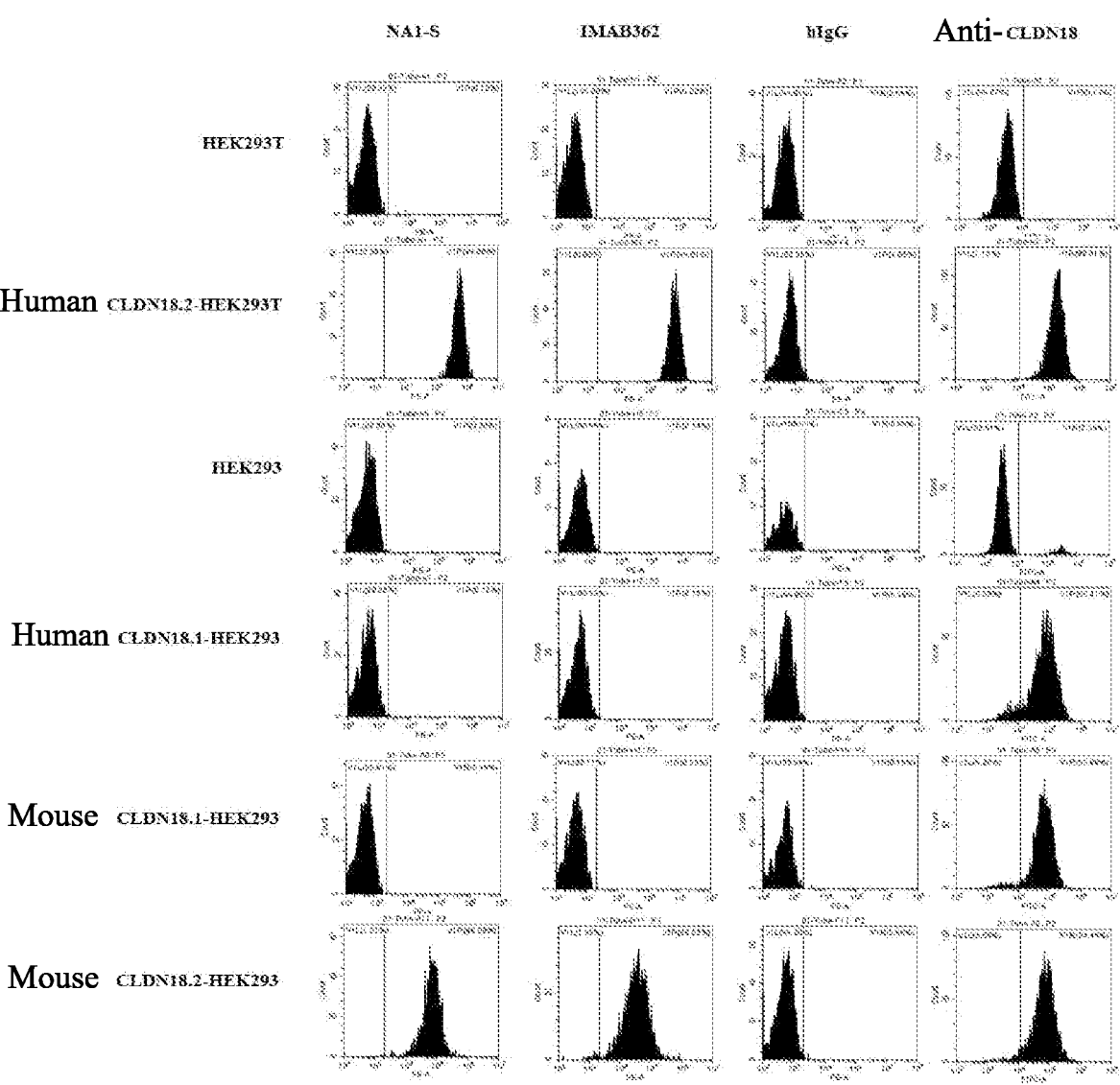
FIG. 3a shows the experimental results of the cross-binding of the candidate antibody NA1-S to human CLDN18.2-HEK293T, human CLDN18.1-HEK293, mouse CLDN18.2-HEK293, and mouse CLDN18.1-HEK293 cell lines.
Figure 3B:
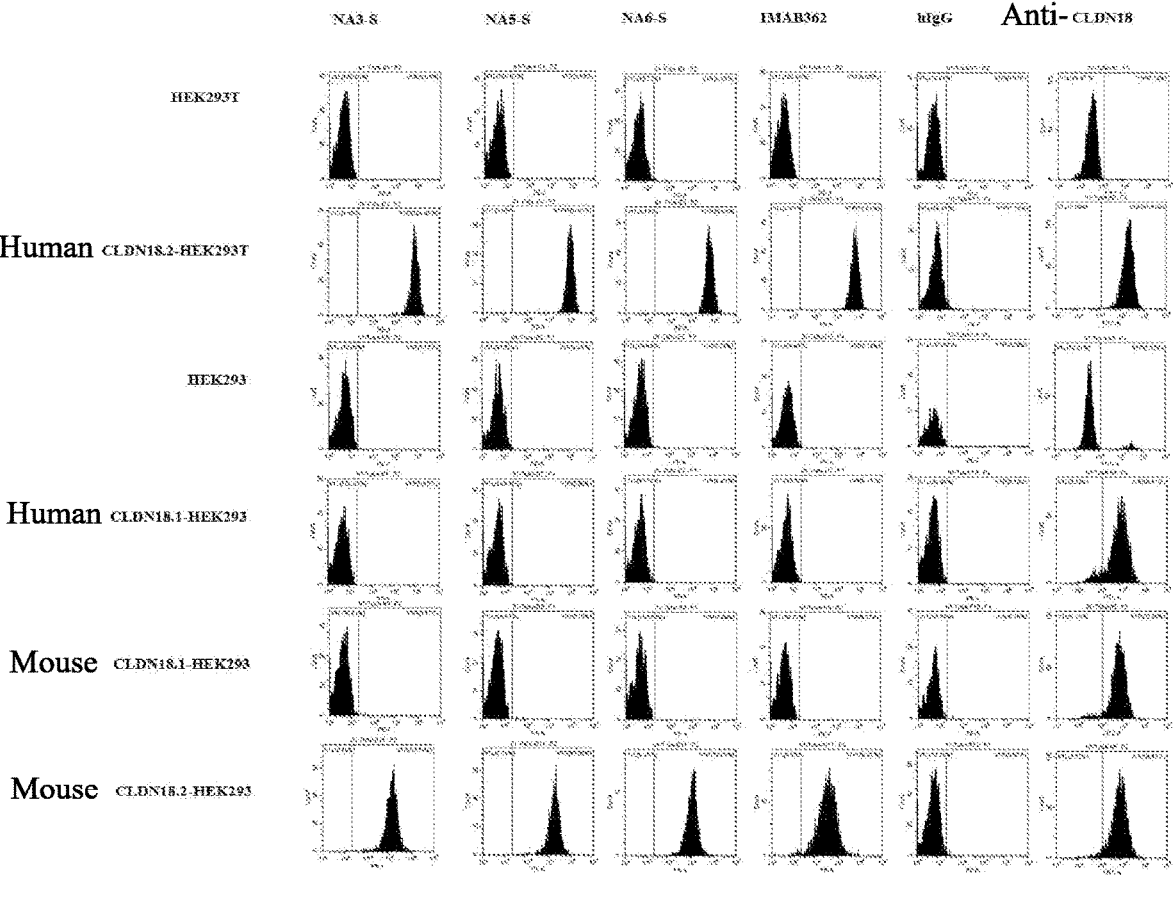
FIG. 3b shows the experimental results of the cross-binding of the candidate antibodies NA3-S, NA5-S, and NA6-S to human CLDN18.2-HEK293T, human CLDN18.1-HEK293, mouse CLDN18.2-HEK293, and mouse CLDN18.1-HEK293 cell lines.

Results from the flow cytometry detection (as shown in FIG. 3) showed that similar to the control antibody IMAB362, the candidate antibodies NA1-S (FIG. 3a), NA3-S, NA5-S and NA6-S (FIG. 3b) all specifically bind to human CLDN18.2-HEK293T and mouse CLDN18.2-HEK293 but did not bind to HEK293T, HEK293, human CLDN18.1-HEK293 and mouse CLDN18.1HEK293 cells. This illustrated that the candidate antibodies NA1-S, NA3-S, NA5-S and NA6-S could specifically bind to CLDN18.2 but did not bind to CLDN18.1, and cross-recognized human and mouse CLDN18.2.

Example 6

Comparison of Binding Ability of Candidate Antibodies on Human CLDN18.2-HEK293T Cell Line and Human CLDN18.2-KATOIII Tumor Cell Line Well-cultured human CLDN18.2-HEK293T cells were taken and incubated with diluted candidate antibodies NA1-S, NA3-S, NA5-S, and NA6-S after being subject to a 3-fold gradient dilution at 4° C. for 1 h. The resulting cultures were rinsed twice with the FACS buffer and incubated at 4° C. for 1 h following the addition of 0.5 µg PE-labeled goat anti-human IgG-Fc antibody (Abcam, ab98596). Subsequently, the obtained cultures were again rinsed twice with the FACS buffer and detected by a flow cytometry.

Figure 4A:
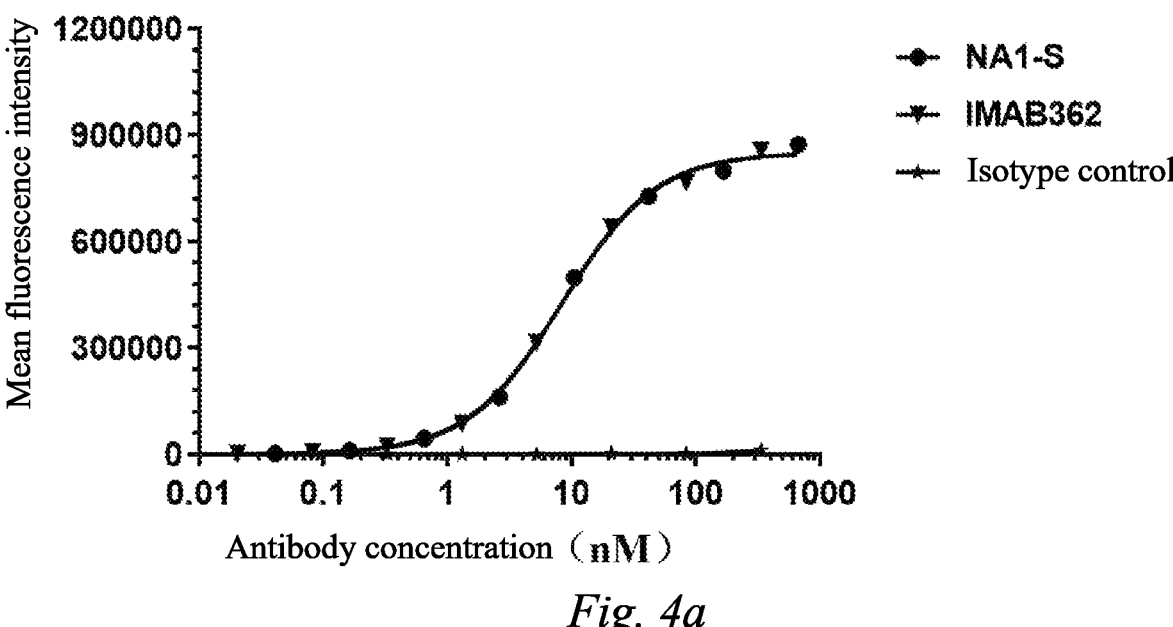
FIGS. 4a and 4b show the experimental results of the binding comparison between the candidate antibody NA1-S and control antibody at the cellular level.
Figure 5A:
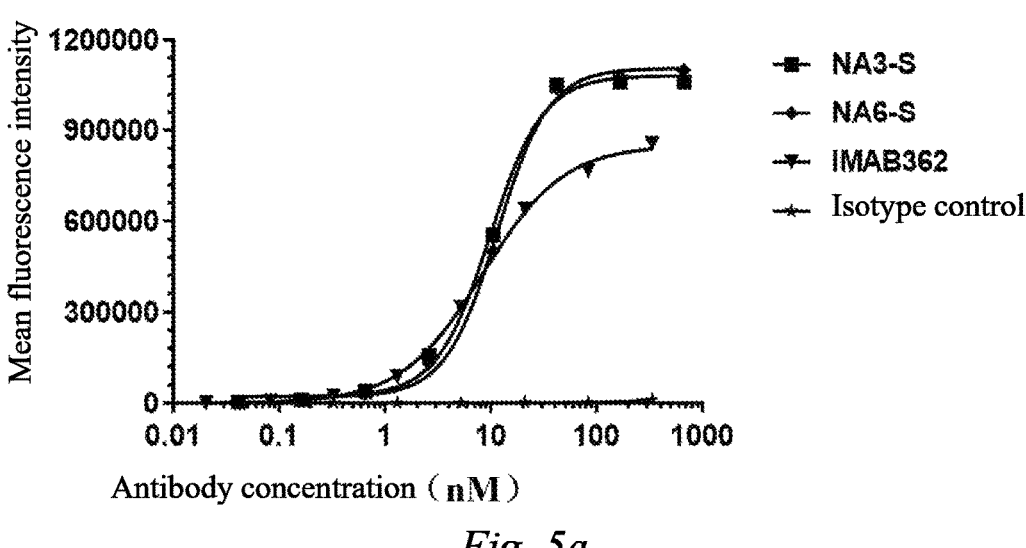
Figure 5B:
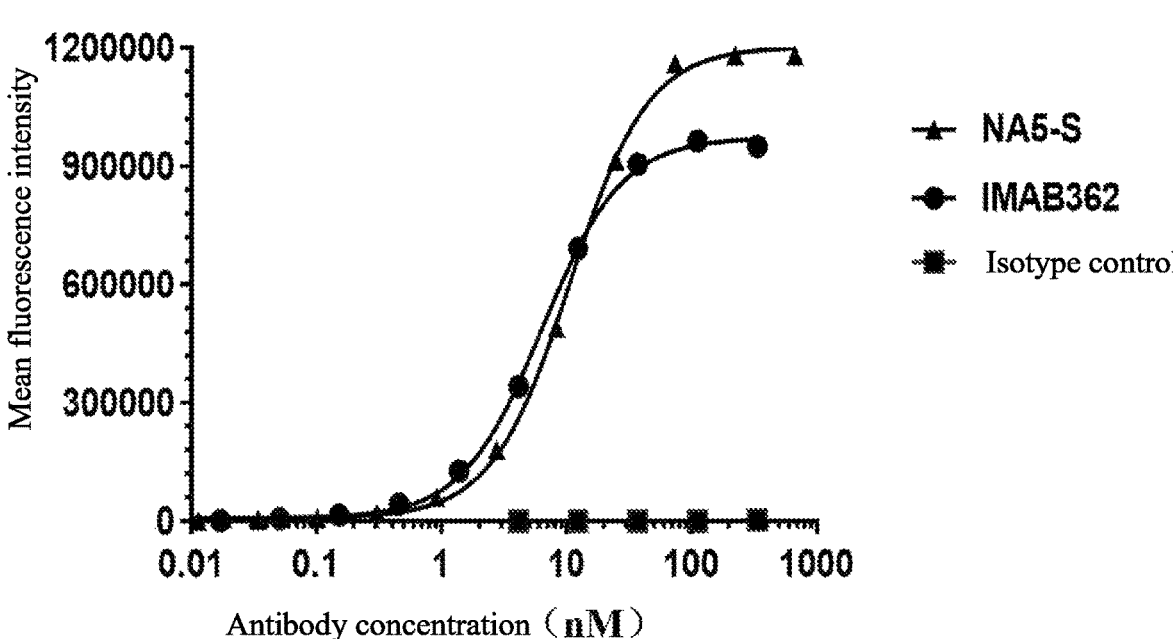

Results from the flow cytometry detection are as shown in FIG. 4a, FIG. 5a and FIG. 5b, and the results showed that, on human CLDN18.2-HEK293T cells, the candidate antibodies all showed comparable cell binding activity to the control antibody.

Figure 4B:
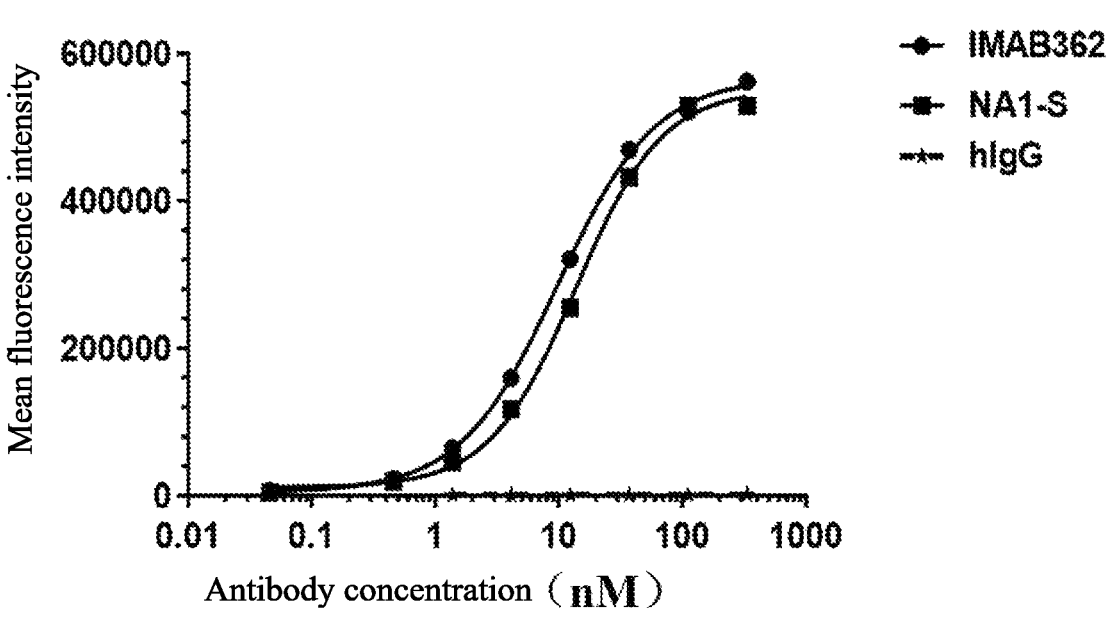
Figure 5C:
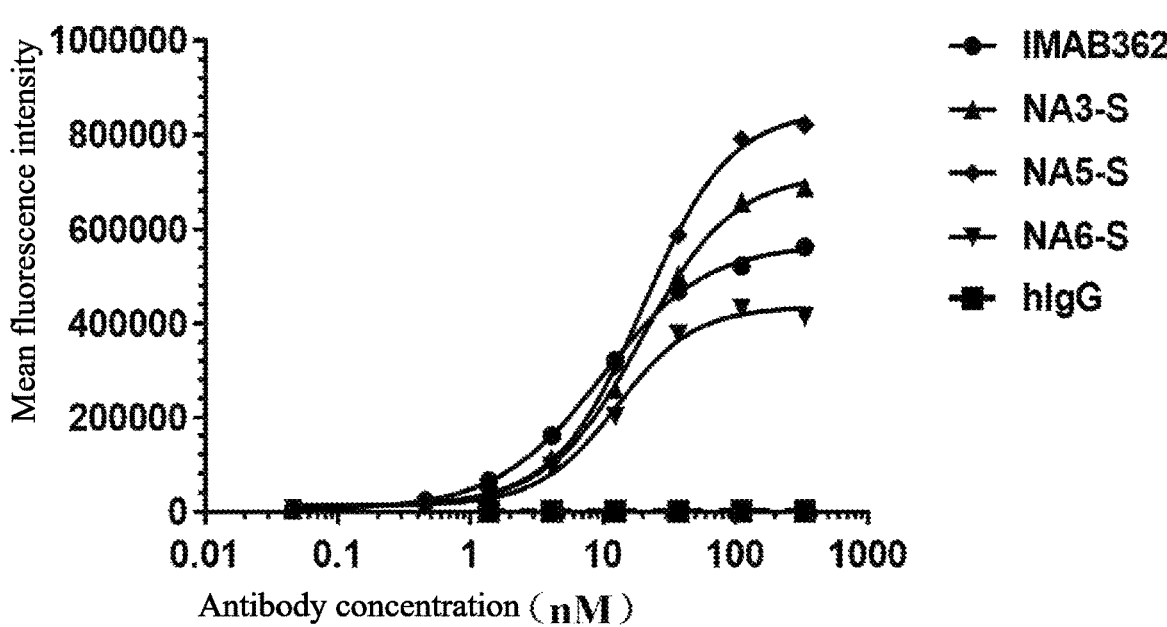

The binding capacity of the candidate antibodies NA1-S, NA3-S, NA5-S, and NA6-S on the human CLDN18.2-KATOIII tumor cell line was determined by using the same method. Results from the flow cytometry detection are as shown in FIG. 4b and FIG. 5c, and the results show that, on human CLDN18.2-KATOIII tumor cell line, the candidate antibodies all showed comparable cell binding activity to the control antibody.

Example 7

Complement Dependent Cytotoxicity (CDC) of Candidate Antibodies

The MTS method was used to determine the CDC cell killing effect of the candidate antibodies. Due to the inclusion of IgG1 Fc fragments, the candidate antibodies NA1-S, NA3-S, NA5-S, and NA6-S could kill cells by CDC. MTS reagent can be reduced to a colored compound by NADPH or NADH produced by viable cells. Therefore, the shading of the color represents the killing effect of antibody-mediated CDC. The specific operating method is as follows:

the candidate antibody NA1-S was taken as an example. Firstly, trypsin was used to digest the well-cultured human CLDN18.2-HEK293T cells, and then $5 \times 10^4$ cells were taken and mixed with 5-fold diluted rabbit serum, and 50 µL of the gradient-diluted candidate antibody NA1-S or control antibody IMAB362 was added, respectively and incubated at 37° C. for 3 h. Subsequently, 30 µL of the MTS reagent (Promega, G3580) was added and fully mixed to uniformity. The resulting cultures were placed in a constant temperature incubator at 37° C. with 5% $CO_2$ and cultured for 4 h, during which period the color of the medium was observed and the OD value at the wavelength of 492 nm was determined by using a microplate reader. 10% Triton X-100 plus target cells were used as the complete lysis control, the addition of target cells only were used as the blank negative control, and rabbit complement plus target cells were used as the background negative control.

Cell killing rate was calculated according to the formula below: cell killing rate (%)=(candidate antibody well OD value−background well OD value)/(complete lysis well OD value−blank well OD value)×100%.

Figure 6A:
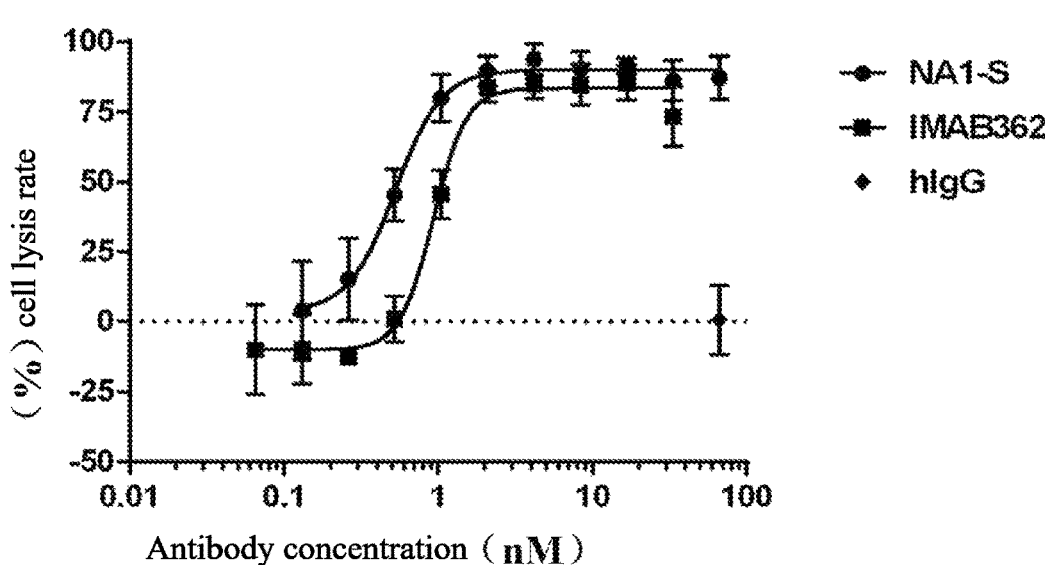
Figure 7A:
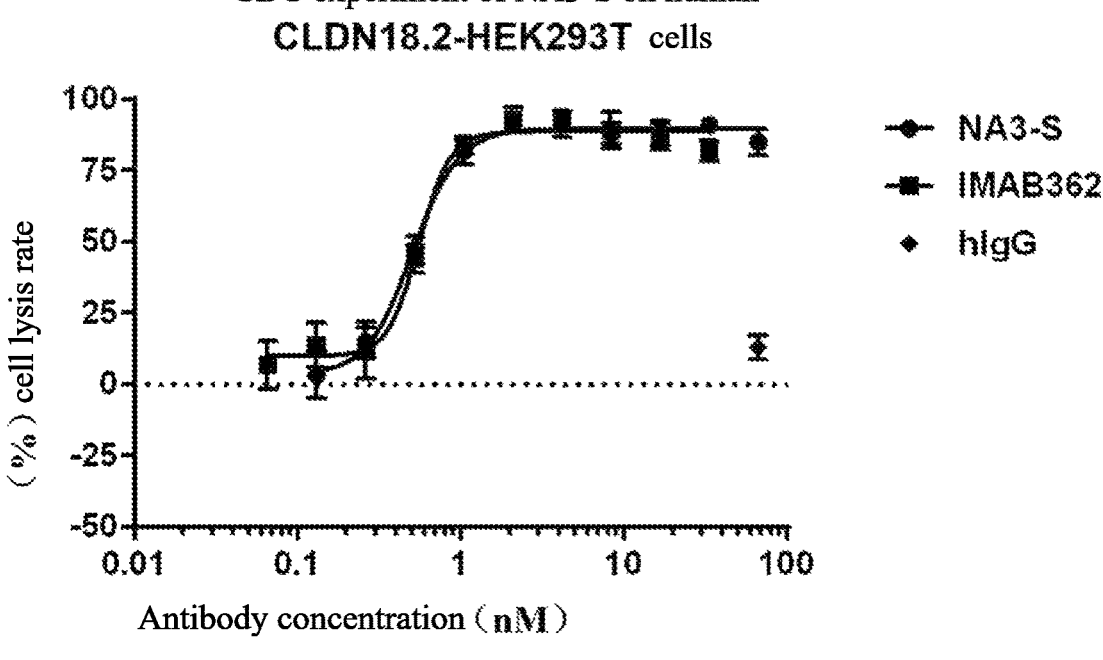
Figure 7B:
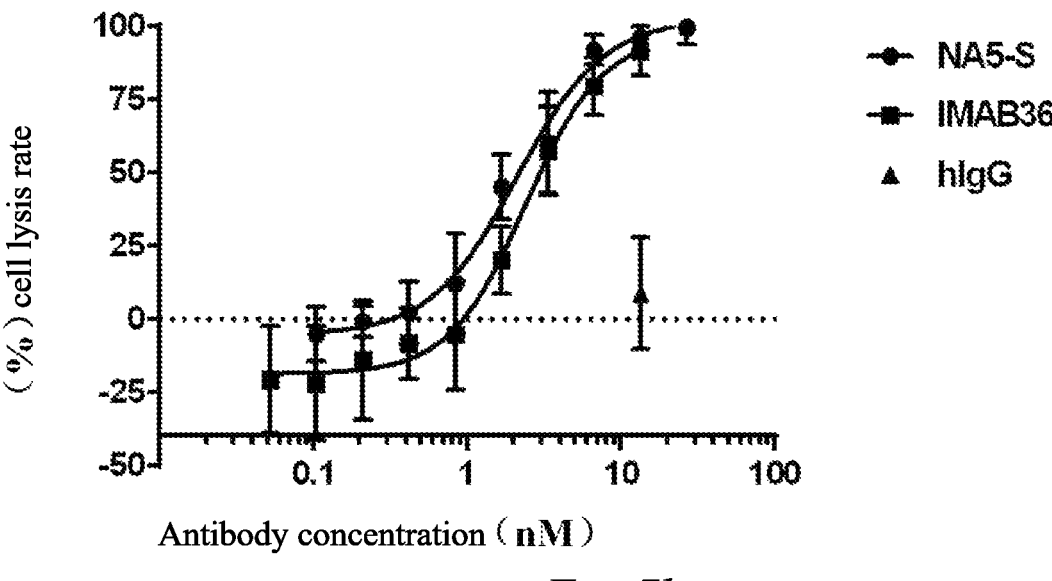
Figure 7C:
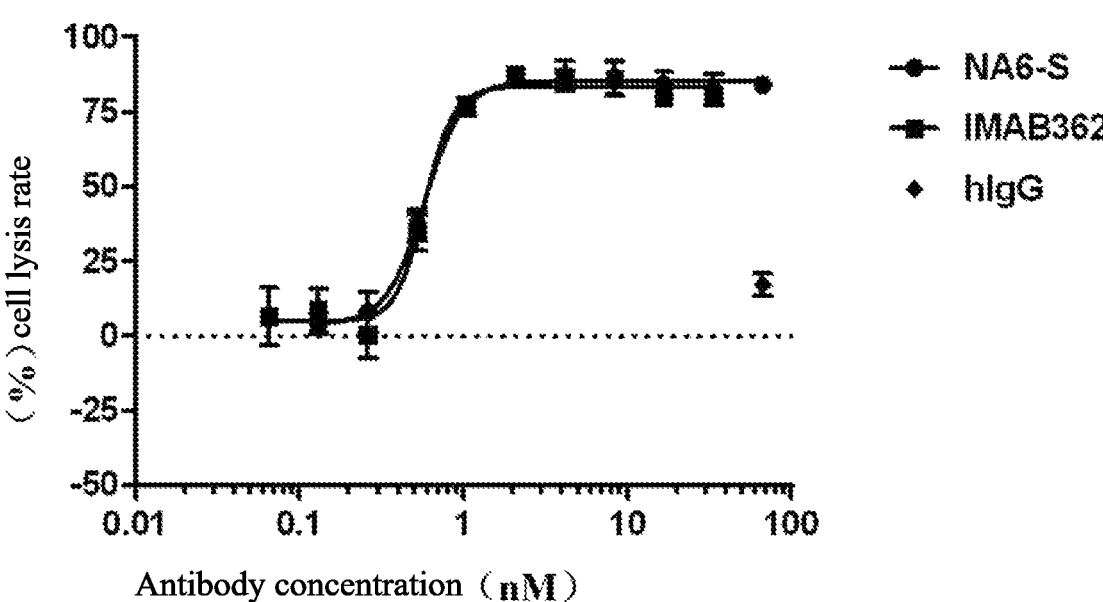

The results of CDC killing effect of the candidate antibody NA1-S on human CLDN18.2-HEK293T tumor cells are as shown in FIG. 6a. It could be seen from FIG. 6a that compared to the control antibody IMAB362, the candidate antibody NA1-S exhibited a stronger CDC cell killing effect at an equimolar concentration, the $EC_{50}$ of NA1-S was 0.5289 nM, whereas the $EC_{50}$ of IMAB362 was 0.936 nM. The CDC killing effects of the candidate antibodies NA3-S, NA5-S and NA6-S on human CLDN18.2-HEK293T cells were determined by using the same method, and the results thereof are as shown in FIGS. 7a-7c. It could be seen from FIGS. 7a-7c that compared to the control antibody IMAB362, the candidate antibodies NA3-S, NA5-S and NA6-S also exhibited comparable CDC cell killing effects at an equimolar concentration.

Figure 6B:
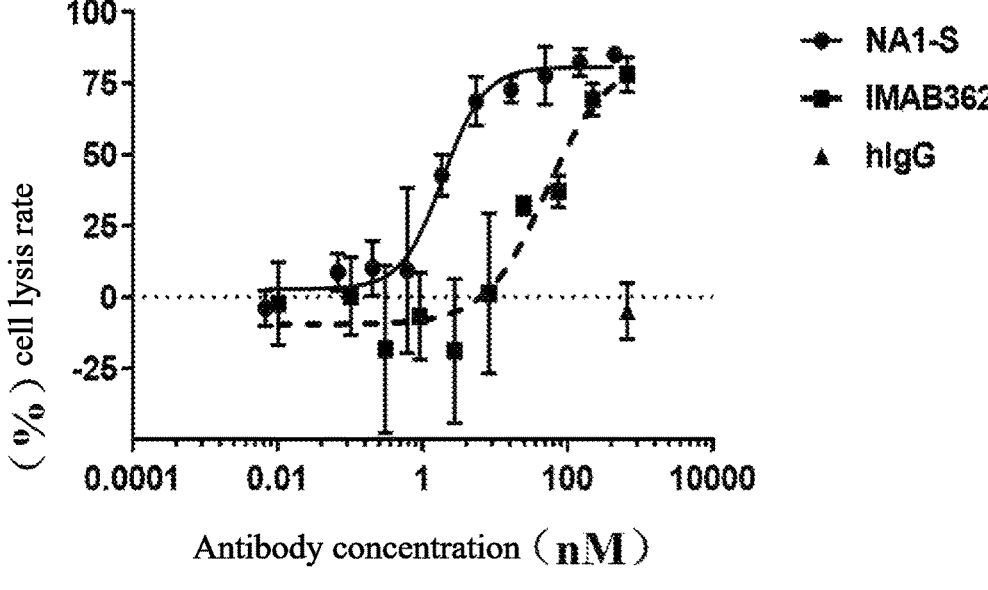
Figure 7D:
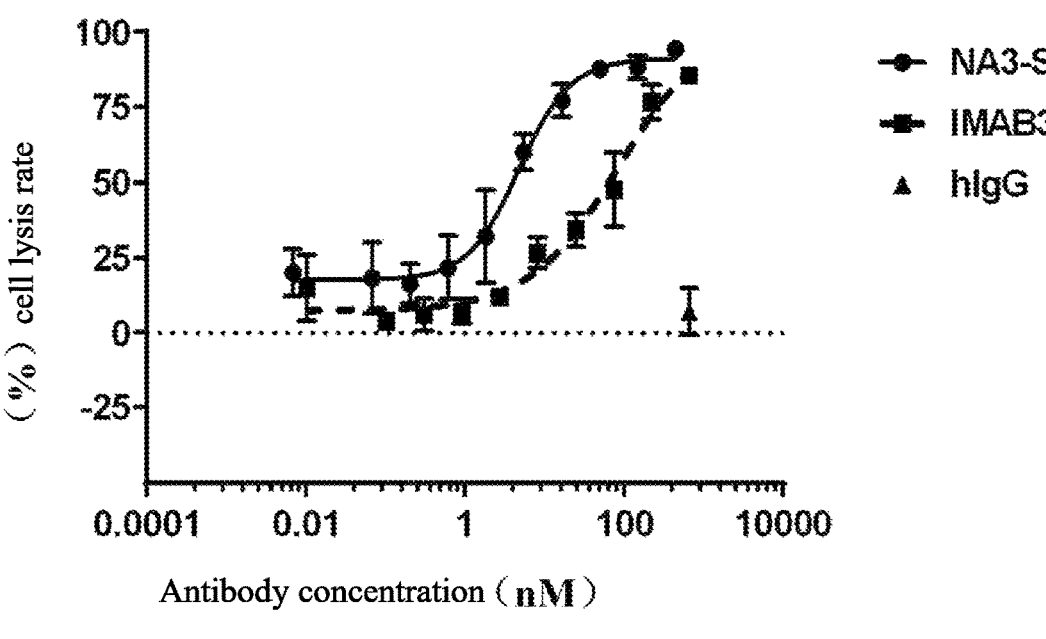

The CDC killing effect of the candidate antibody NA1-S on human CLDN18.2-KATOIII tumor cells was determined by using the same method, and the results thereof are as shown in FIG. 6b. It could be seen from FIG. 6b that compared to the control antibody IMAB362, NA1-S exhibited a stronger CDC cell killing effect at an equimolar concentration, wherein the EC50 of NA1-S was 1.91 nM, whereas the EC50 of IMAB362 was 50.86 nM. The CDC effects of the candidate antibodies NA3-S, NA5-S and NA6-S were determined by using the same method as NA1-S, and similar to NA1-S, the antibodies also had stronger CDC cell killing effects, compared to the control antibody IMAB362. For example, compared to the control antibody IMAB362, NA3-S exhibited a stronger CDC cell killing effect at an equimolar concentration, wherein the EC50 of the nanobody NA3-S was 4.831 nM, whereas the EC50 of IMAB362 was 85.83 nM (FIG. 7d).

Example 8

Antibody-Dependent Cell-Mediated Cytotoxicity (ADCC)

Lactate dehydrogenase (LDH) release method was used to detect the ADCC effect. The principle is that, the variable region of an antibody binds to a target antigen on a target cell and the Fc fragment of the antibody binds to the FcRIIIa (also known as CD16a) on a NK effector cell in PBMC, and then the NK cell will release perforin, granzymes, etc. to lyse the target cell. The release of lactate dehydrogenase in the cell supernatant can be detected with a LDH lactate dehydrogenase kit (Takara, MK401), thereby determining the degree of killing of the target cell by the NK cell. The specific operations are as follows:

50 μL of human CLDN18.2-HEK293T cells were added to each well of a 96-well cell culture plate at a density of 2× 105 per mL and placed in a 37° C. incubator and incubated overnight (16-20 h). 50 μL of gradient-diluted candidate antibodies NA1-S or NA3-S was added and mixed to uniformity and incubated in a 37° C. incubator for 20 min; then recovered human PBMC cells were added at $5×10^5$ cells per well (the ratio of effector cells/target cells being 50:1) and incubated in a 37° C. incubator for 4 h. Subsequently, the resulting cultures were centrifuged at 300 g to obtain the supernatant, and then LDH detection reagents were added and reacted for 60 min, and finally the OD value at the wavelength of 492 nm was determined by a microplate reader (Molecular Devices, SpectraMax190) and the detection results were analyzed. 10% Triton X-100 plus target cells were used as the complete lysis control, the addition of target cells only were used as the blank negative control, and PBMC plus target cells were used as the background negative control.

Cell killing rate was calculated according to the formula below: killing rate (%)=(candidate antibody well OD value−background well OD value)/(complete lysis well OD value−blank well OD value)×100%

Figure 8A:
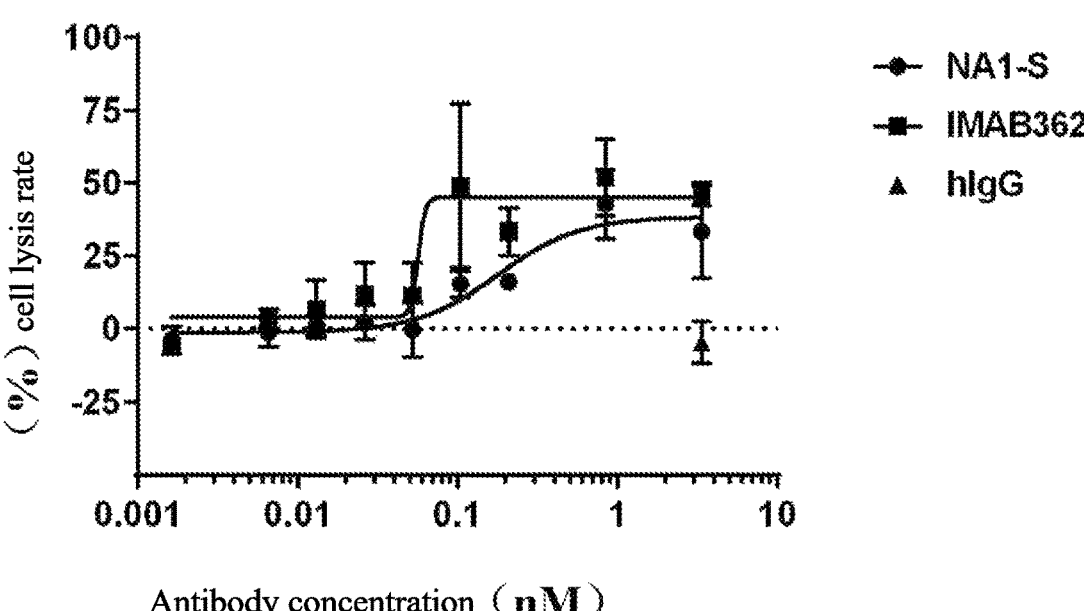

The results (FIGS. 8a and 8c) showed that the candidate antibodies NA1-S and NA3-S have cell killing activities equivalent to the control antibody IMAB362 at equimolar concentrations.

Figure 8B:
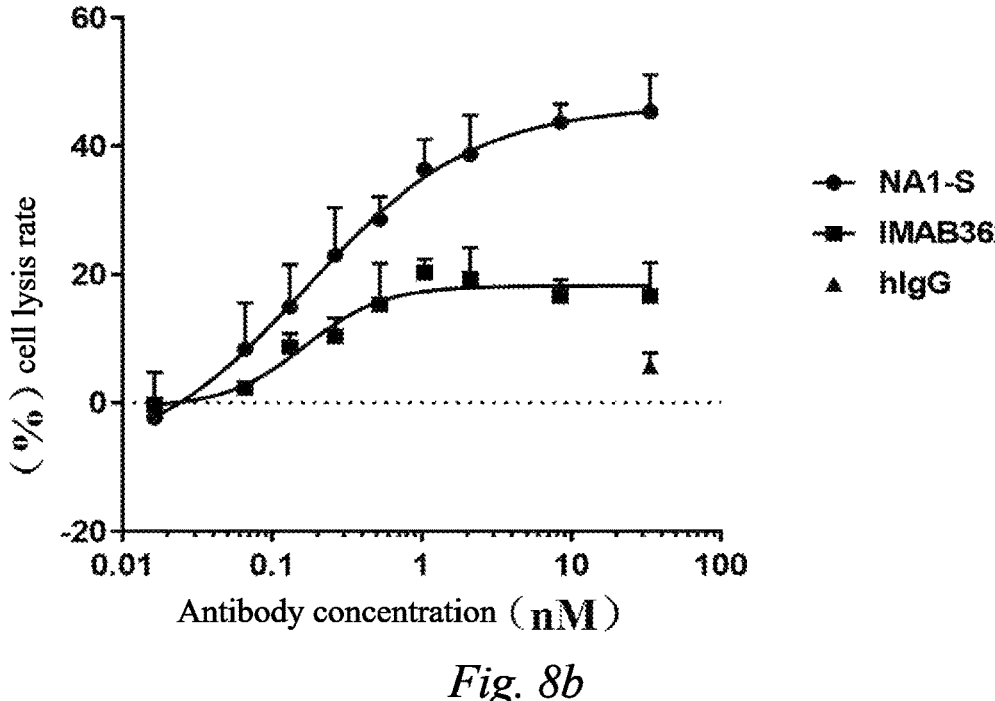
Figure 8C:
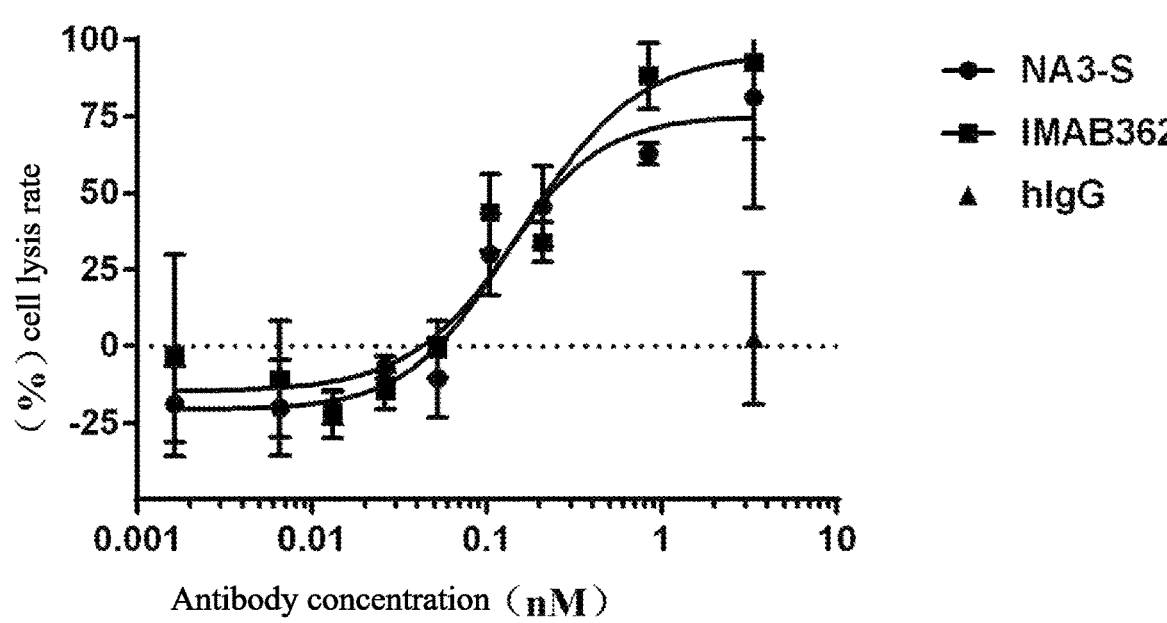
Figure 8D:
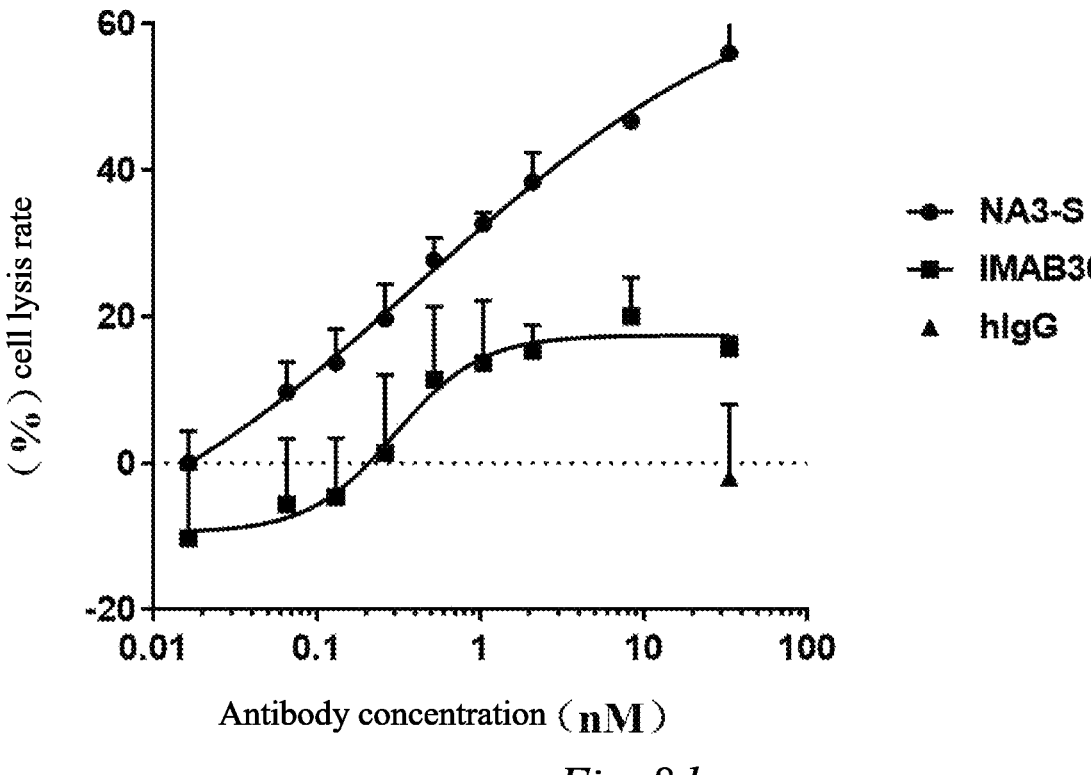

The ADCC killing effect of the candidate antibodies NA1-S or NA3-S on human CLDN18.2-KATOIII tumor cells was determined by using the same method, and the results were as shown in FIGS. 8b and 8d. The results from FIG. 8b showed that NA1-S exhibited a stronger ADCC cell killing effect than the control antibody IMAB362 at equimolar concentrations, wherein the killing efficiency of the candidate antibody was as high as 45%, whereas the killing efficiency of the control antibody IMAB362 was only 17%. The results from FIG. 8d showed that NA3-S also exhibited a stronger ADCC cell killing effect than the control antibody IMAB362 at equimolar concentrations, wherein the killing efficiency of the candidate antibody was nearly 50%, whereas the killing efficiency of the IMAB362 control antibody was only 20%-25%.

Example 9

In Vivo Tumor Inhibition Experiment (Using Human CLDN18.2-HEK293T as the Tumorigenic Cell Line)

6-8 weeks old, female SCID mice (body weight 24-26 g) were used in the experiment. The experimental mice were housed in an independent ventilated box with constant temperature and humidity. the rearing chamber has a temperature of 21° C.-24° C. and a humidity of 30%-53%.

$1×10^7$ human CLDN18.2-HEK293T cells were injected into the right axilla by subcutaneous injection. When the volume of the subcutaneous tumor mass reached 80-100 $mm^3$, the mouse samples with large differences in tumor volume were removed, and randomized grouping was carried out based on the tumor volume (8 mice in each group): PBS treatment group, IMAB362 antibody treatment group, and candidate antibody NA1-S treatment group, respectively. Antibody treatment began 6 days after cell inoculation (for the candidate antibody NA1-S, based on the molecular weight, a dose with a molar concentration equal to that of the IMAB362 antibody was adopted. When converted into a mass concentration, the doses were 2.5 mg/kg and 5 mg/kg, respectively), with twice weekly dosing of alternate intravenous injection and intraperitoneal injection, respectively. The length (mm) and width (mm) of the tumor were observed and recorded, and the tumor growth volume (V) thereof was calculated. The formula mode was: V=(length×width²)/2. The candidate antibody NA3-S was tested by using the same method. For the candidate antibody NA3-S, based on the molecular weight, a dose with a molar concentration equal to that of the IMAB362 antibody was adopted, when converted into a mass concentration, the doses were 5 mg/kg and 10 mg/kg, respectively.

Figure 9A:
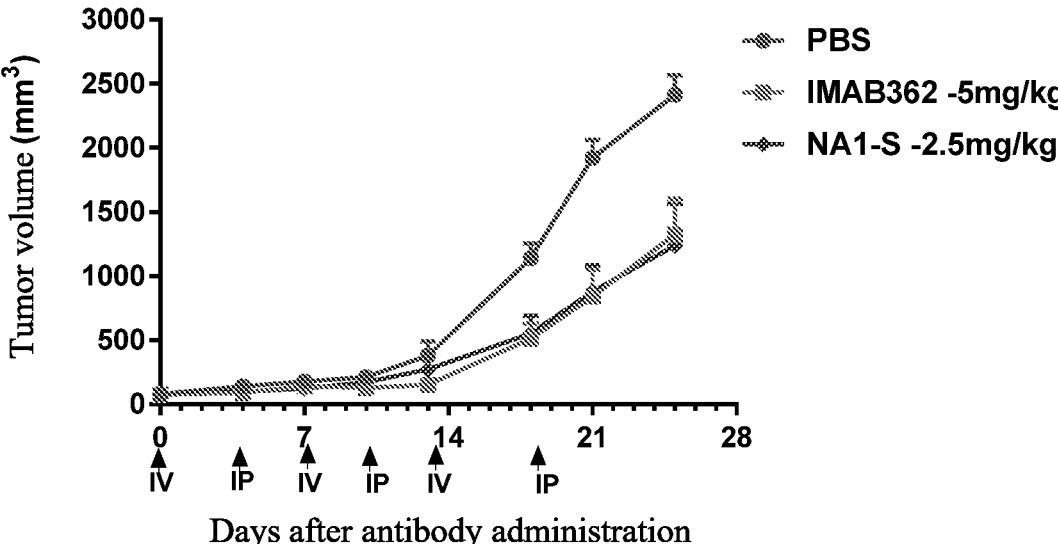
FIGS. 9a and 9b show the tumor inhibition effect of the candidate antibodies NA1-S and NA3-S in the human CLDN18.2-HEK293T xenograft model, wherein, mice used are immunodeficient (SCID) mice, the administration doses of NA1-S and IMAB362 are calculated according to the mass concentration, and the administration route used is tail vein and intraperitoneal crossover administration.
Figure 9B:
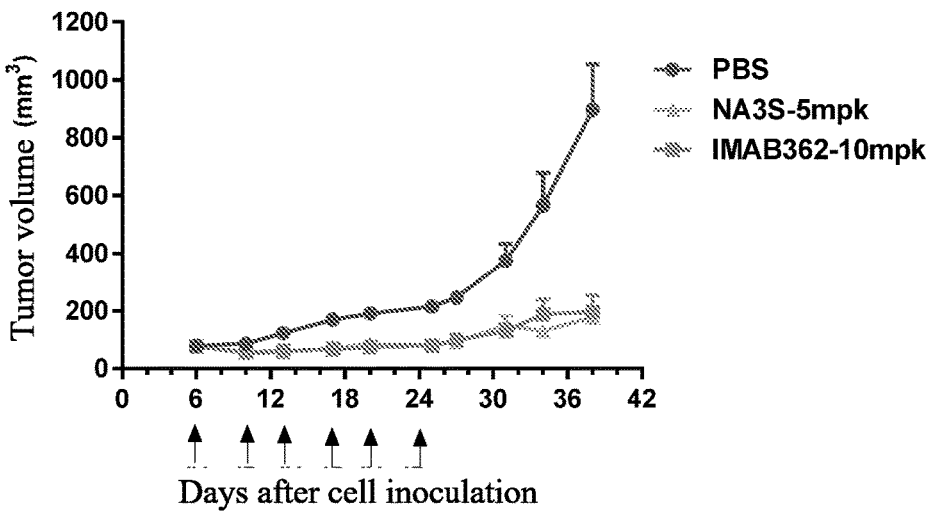

The tumor inhibition results of the antibodies are as shown in FIGS. 9a-9b, from which it could be seen that: compared to the control antibody IMAB362, the candidate antibody NA1-S at a dose being such a low mass concentration, was similar to the control antibody at high concentration in terms of tumor growth inhibition, and the tumor growth inhibition rate was about 55%. The candidate antibody NA3-S at a dose being a low mass concentration, was similar to the control antibody at high concentration in terms of tumor growth inhibition. The candidate antibody NA3-S and the control antibody could both achieve the almost complete inhibition of tumor growth.

Example 10

Determination of Binding Epitope of Candidate Antibodies on Human CLDN18.2

Candidate antibodies and the control antibody IMAB362 both specifically bind to CLDN18.2 but do not bind to CLDN18.1, and the extracellular regions of CLDN18.2 and CLDN18.1 only differ by 8 amino acids in the ECD1 region. Therefore, it is speculated that the antigen binding epitopes of the candidate antibodies and the control antibody IMAB362 are within the ECD1 region. In order to confirm whether the antigen binding positions of the candidate antibodies and IMAB362 are the same, this example adopts the method of competitive binding. The specific method is as follows:

CLDN18.2-HEK293T cells serially passaged 2-4 times and well-grown were used in the experiment. Following a centrifugation at 4° C., 300 g and the removing of the supernatant, the cells were resuspended with the FACS buffer and counted. This was followed by the adjustment of the cell density to $2\times10^6$ cells/mL and the addition to a new 96-well round-bottom plate at 100 μL per well. After a centrifugation at 4° C., 300 g, the supernatant was removed.

Taking the candidate antibody NA1-S as an example, an FACS buffer (1×PBS+2% FBS) was prepared and the competing antibody NA1-S (or IMAB362) was diluted in a gradient manner with the FACS buffer. The FACS buffer was also used to dilute the biotin-labeled IMAB362 (or NA1-S) protein to 13.4 nM. 100 μL of the gradient diluent and 100 μL of the biotin-labeled protein diluent were added to the 96-well plate, respectively and gently pipetted to uniformity with a multi-channel pipettor, and the 96-well plate was placed at 4° C. and incubated for 1 h. The incubated mixture of antibodies and cells was centrifuged at 4° C., 300 g and the supernatant was removed. Subsequently, 200 μL of the FACS buffer was added to each of the corresponding wells and the cells were resuspended and centrifuged at 4° C., 300 g and the supernatant was removed; and this step was repeated twice. The PE-labeled streptavidin (eBioscience, 12-4317-87) was diluted 1:200 by using the FACS buffer and added to the corresponding cells by using a multi-channel pipettor at 200 μL per well and gently pipetted to resuspend the cells. Subsequently, the cells were placed at 4° C. and incubated for 30 min protected from light. After completion of the incubation, the cells were centrifuged at 4° C., 300 g and the supernatant was removed. The FACS buffer was added to resuspend the cells. This step was repeated twice. Finally, the detection was performed by flow cytometry (Beckman, CytoFLEX AOO-1-1102).

Figure 10A:
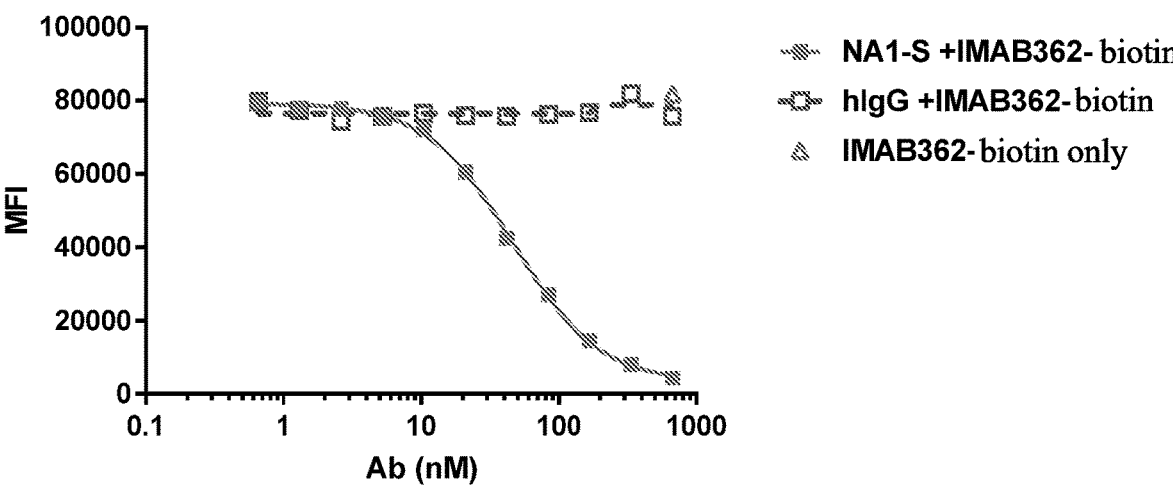

The results obtained from the flow cytometry are as shown in FIG. 10a: with the increase of the concentration of NA1-S, the binding of IMAB362-biotin on CLDN18.2-

Figure 10B:
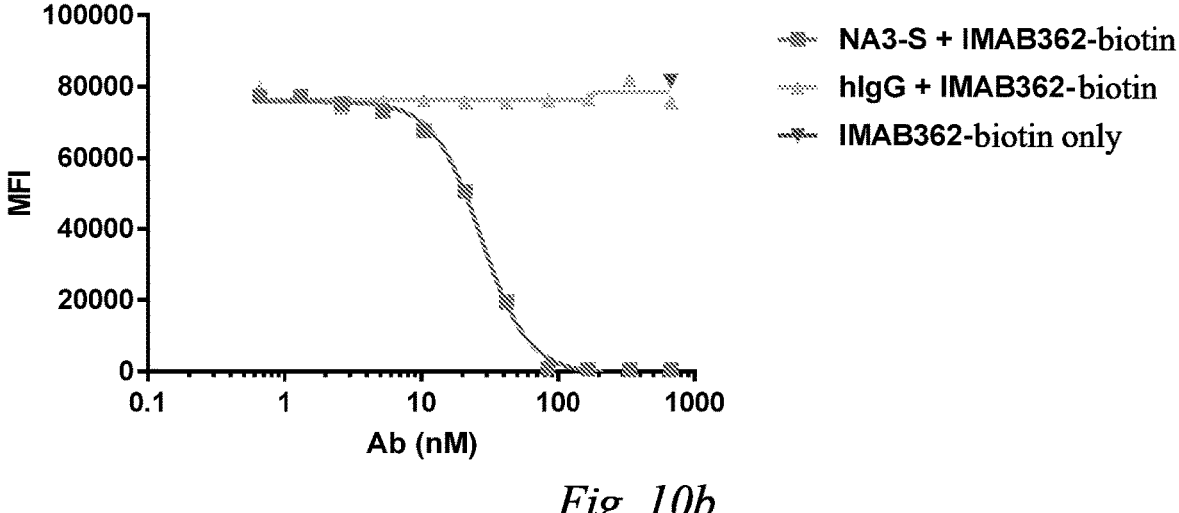
Figure 10C:
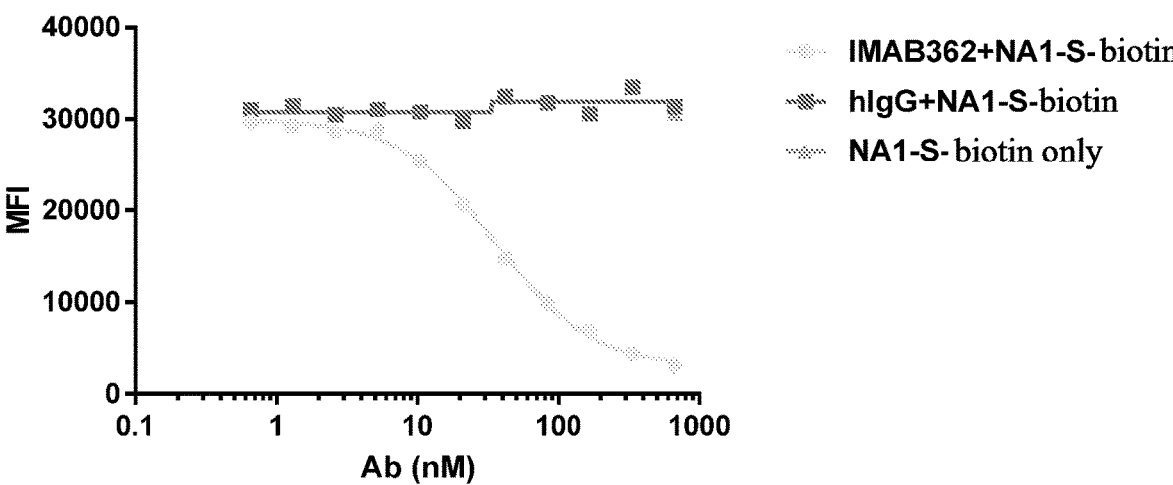
Figure 10D:
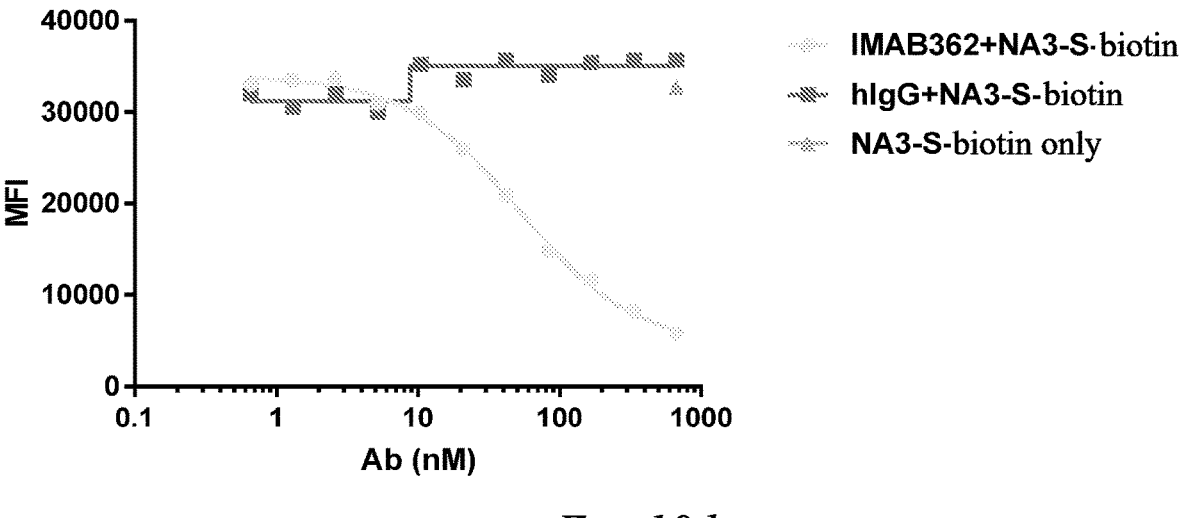

HEK293T cells decreased. Similarly, as shown in the results obtained from the flow cytometry of FIG. 10c, with the increase of the concentration of IMAB362, the binding of NA1-S-biotin on CLDN18.2-HEK293T cells decreased. All these indicated that NA1-S and IMAB362 binds to similar epitopes on CLDN 18.2. As shown in FIGS. 10b and 10d, the results of NA3-S are similar to those of NA1-S.

Figure 10E:
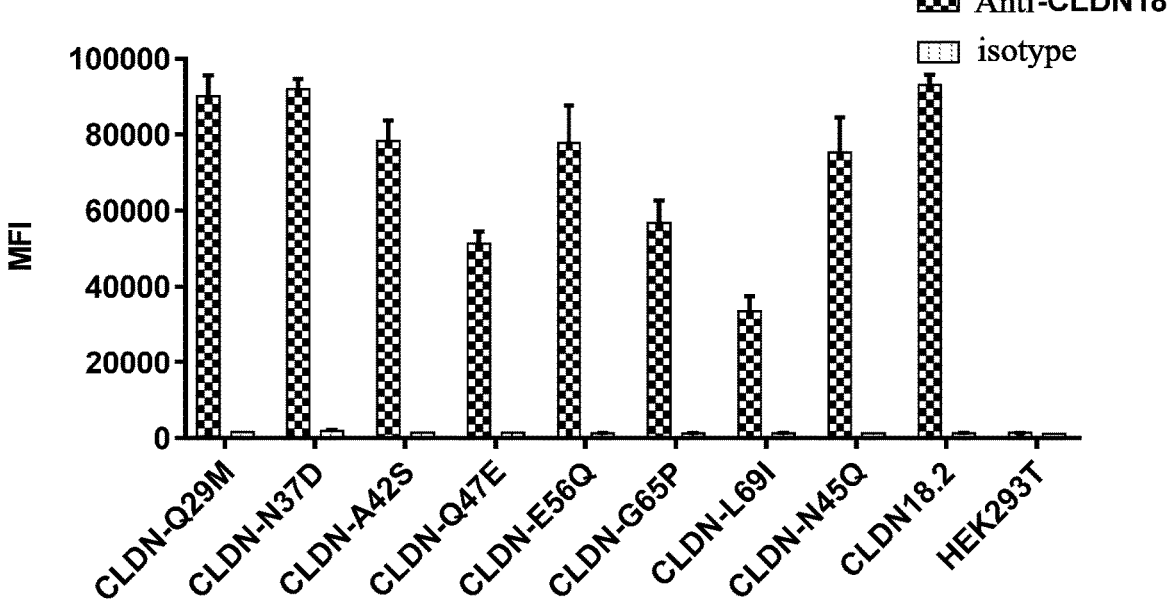
Figure 10F:
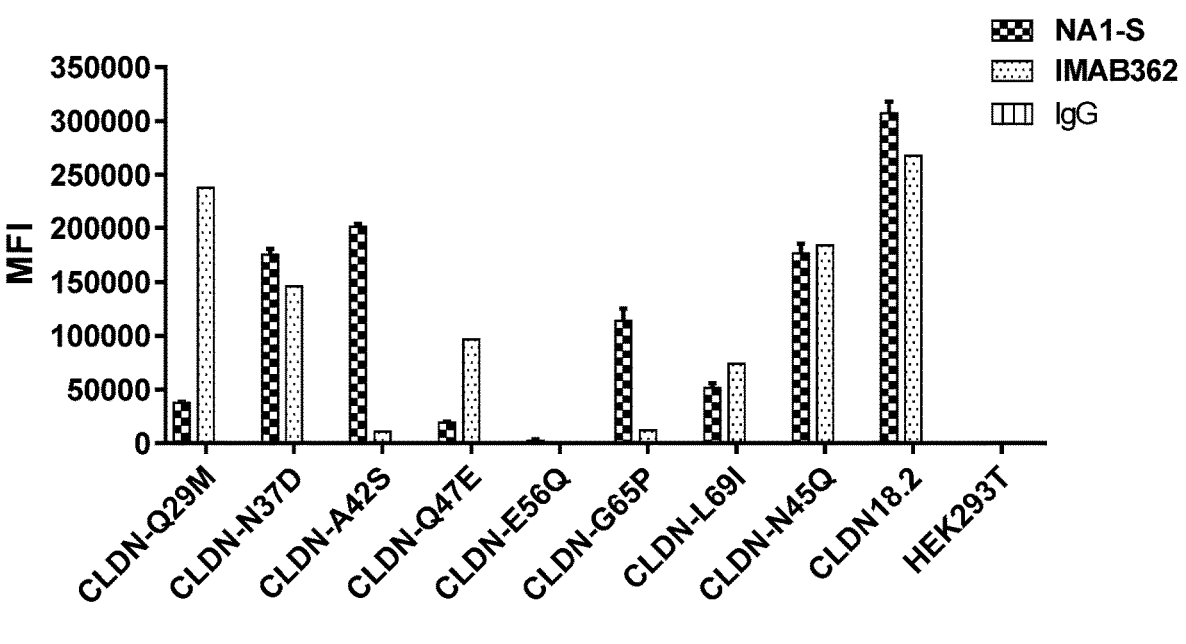
Figure 10G:
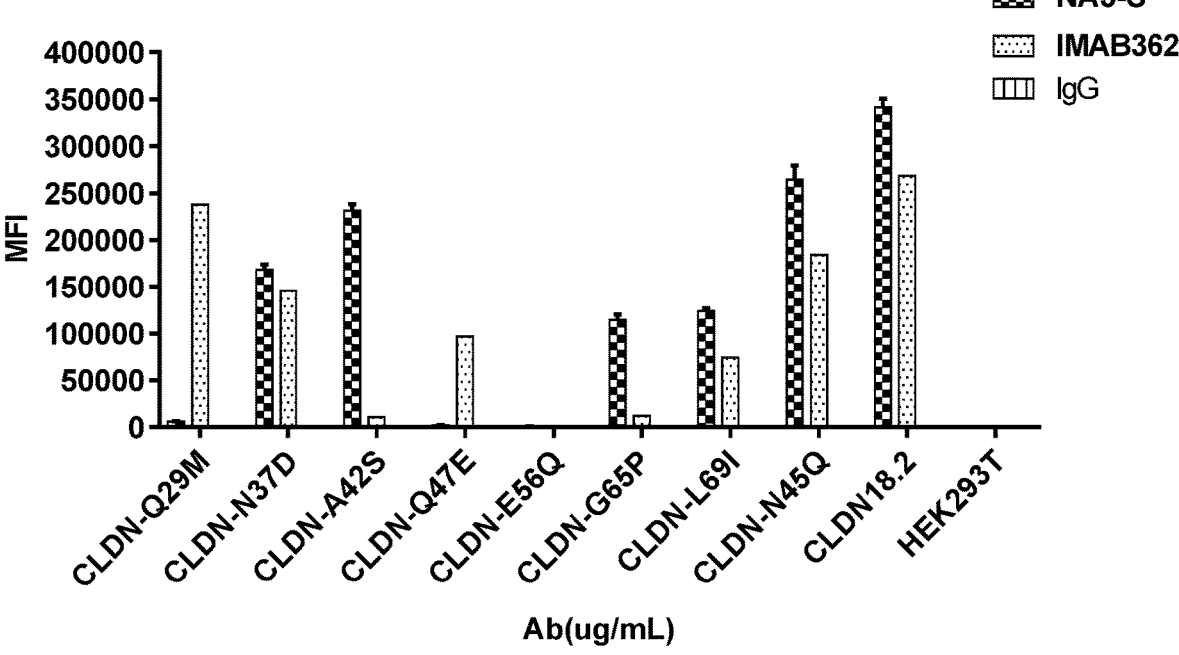
Figure 10H:
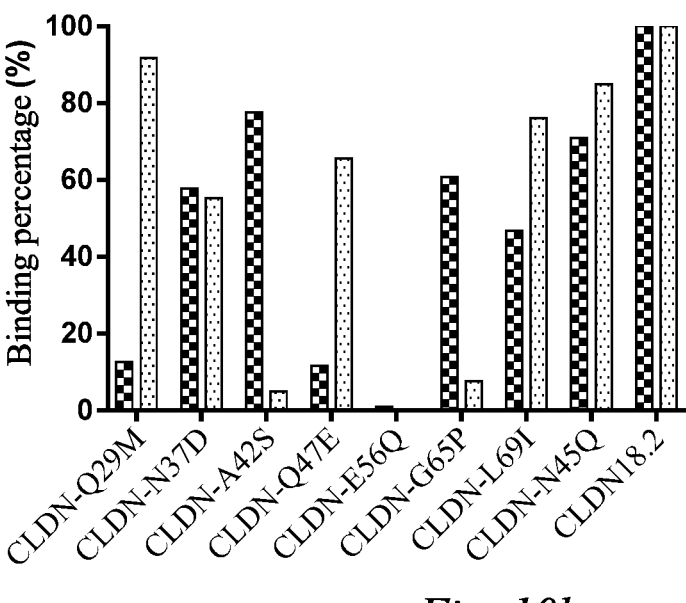
Figure 10H:
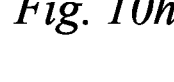
Figure 10I:
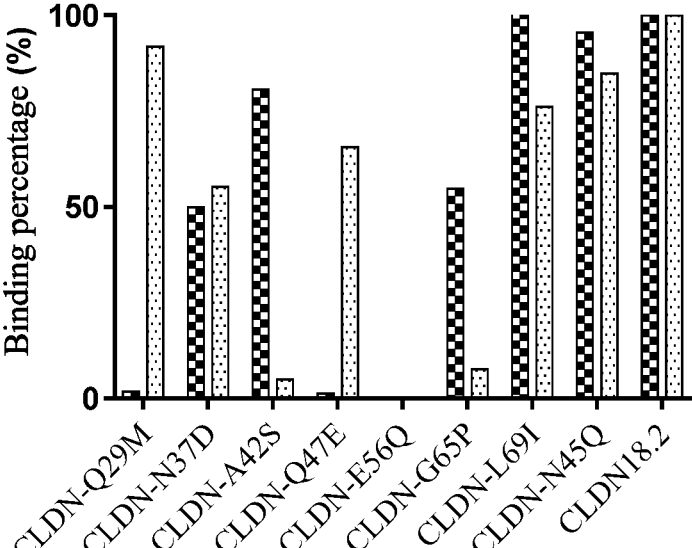

To further understand the amino acid positions on CLDN18.2 that are critical for NA1-S or NA3-S and IMAB362, 8 mutant HEK293T cell lines were constructed in this example based on the 8 amino acid differences between CLDN18.2 and CLDN18.1 in ECD1. The 8 different amino acids within CLDN18.2 were mutated to the corresponding amino acids in CLDN18.1, respectively and whether an amino acid is critical for antibody binding was determined by measuring the difference between the binding capacities of the tested antibodies on the wild type cell line and the mutant cell lines. The detailed method is as follows:

firstly, the expression of CLDN18.2 in the wild type and mutant huCLDN18.2-HEK293T cell lines was determined by using the method as described in 1.3.2. The cells were fixed and permeabilized according to the method in the instruction of the cell permeabilization kit (eBioscience, 88-8824-00), and the expression was determined according to the binding capacity of the anti-CLDN18 antibody [34H14L15] to the C-terminal intracellular segment of CLDN18. The results are shown in FIG. 10e, each mutant cell line and the wild type cell line have relatively high expression of CLDN18.2.

Based on this, with reference to the method in 1.3.1, the binding strength of the candidate antibodies NA1-S or NA3-S, and IMAB362 on CLDN18.2 wild type and mutant huCLDN18.2-HEK293T cell lines was determined. In addition, the binding strength of the candidate antibodies was divided by the expression level of each cell line and normalized by taking the binding of the candidate antibodies on the wild type cell line as 100% and the normalized results were used as the relative binding strength. As shown in FIGS. 10f-i, the three positions (Q29, Q47 and E56, respectively) on CLDN18.2 ECD1 were very crucial for the binding of NA1-S and NA3-S to human CLDN18.2-HEK293T, while A42, E56 and G65 were three amino acids crucial for IMAB362 binding to CLDN18.2.

Example 11

Candidate Antibody-Mediated Fab-ZAP Cell Killing Effect

CLDN18.2 is highly expressed in a variety of tumors, but in normal tissues, CLDN18.2 is specifically expressed in the tight junction structures of gastric epithelial cells. Therefore, CLDN18.2 may become an ideal ADC drug target. In this experiment, the internalization activity of an antibody was detected by antibody-mediated Fab-ZAP cytotoxicity, wherein the Fab-ZAP (Atsbio, IT-51-100) is a Fab fragment that is linked to the anti-Fc region of saporin, and saporin is a ribosome inhibitor that can inhibit protein synthesis and cause cell death. Following the incubation of the Fab-ZAP and the antibody of CLDN18.2, the antibody of CLDN18.2 would carry the Fab-ZAP when the antibody of CLDN18.2 was internalized, the Fab-ZAP entered the cell along with the antibody, thereby killing the cell. Then the cell activity was detected by MTS (Promega, G3580) so as to detect and compare the internalization activity of the candidate antibody and the control antibody. The specific method is as follows:

CLDN18.2-HEK293T cells in the log growth phase were taken and digested with trypsin (0.25% (w/v) Trypsin, 0.53 mM EDTA) until there was no adhesion between the cells. By then, the digestion was terminated with a complete medium. After the cells were fully mixed to uniformity, the cells were counted and the viability thereof was determined. The cells were adjusted to the density of $4\times10^4$ cells/mL and were added to a cell culture plate at 50 µL per well and incubated in a 37° C. cell incubator for 16 hours. In addition, a DMEM complete medium was used to dilute the Fab-ZAP to 2 µg/mL. The resulting solution was used as a diluent to further dilute the candidate antibodies NA1-S, NA3-S and the control antibody in a gradient manner. 50 µL the obtained diluent was taken using a multi-channel pipettor and added to the cell culture plate and mixed with CLDN18.2-HEK293T to uniformity by gently pipetting. The cell culture plate was added to a 37° C. cell incubator for further 72 hours incubation. Then, 20 µL MTS was added to each well using a multi-channel pipettor, pipetted to uniformity and incubated at 37° C. for 2-4 hours, and finally, after the cell plate was centrifuged in a benchtop centrifuge at 1000 rpm for 5 minutes, the data was read in a microplate reader (Molecular Devices, SpectraMax 190) at detection wavelength of 492 nm.

Figure 11A:
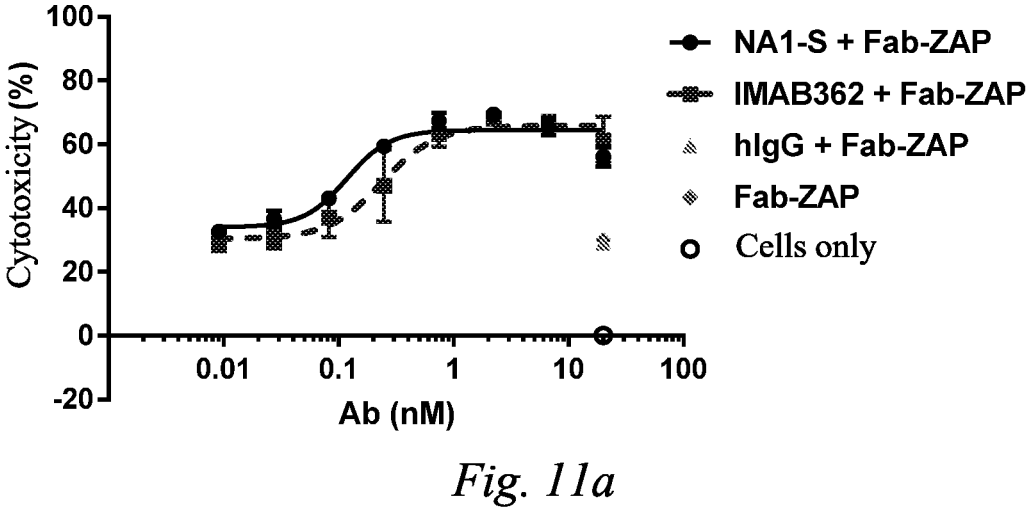
FIGS. 11a-11b show the cell killing efficiency of NA1-S (FIG. 11a) or NA3-S (FIG. 11b), and IMAB362 on CLDN18.2-HEK293T in the presence of Fab-ZAP, wherein hIgG and Fab-ZAP are used as the control in the test, and when incubated with cells for a long period of time, Fab-ZAP also has certain cytotoxic effects on the cells.
Figure 11B:
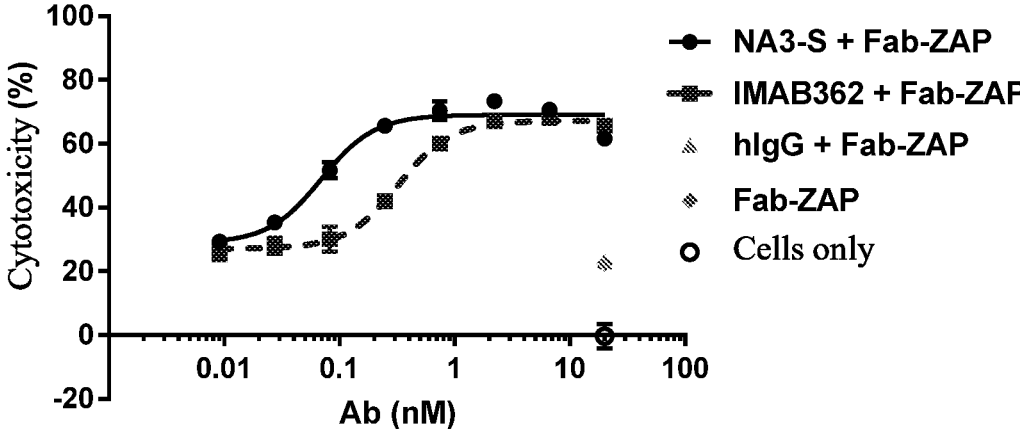

The results are as shown in FIGS. 11a-11b, compared to the control antibody IMAB362, the candidate antibodies NA1-S and NA3-S could more effectively kill the target cell CLDN18.2-HEK293T by the Fab-ZAP, the IC50s of NA1-S and IMAB362 were 0.1 nM and 0.24 nM, respectively, and the IC50s of NA3-S and IMAB362 were 0.07 nM and 0.32 nM, respectively. This fully demonstrates that the candidate antibodies can enter cells through CLDN18.2, they are superior to the control antibody IMAB362, and have the potential to be used in the development of antibody-drug conjugate (ADC).

Example 12

Humanization of Candidate Antibody NA3-S

Compared to mouse antibodies, alpaca-derived nano-antibodies share higher homology to human antibodies, but their structures are special. Therefore, in the NA3-S humanization design process, the germline gene closest to human was selected. Moreover, during reverse mutation, the maintaining of the structures of the antibodies was given consideration, and a series of humanized antibodies were finally designed. Among them, NA3S-H1 is the optimum molecule, and the antibody sequences thereof are as shown in the table below.

| | CDR1 | | CDR2 | | CDR3 |
|---|---|---|---|---|---|
| SEQ ID NO. | Sequence | SEQ ID NO. | Sequence | SEQ ID NO. | Sequence |
| 30 | GSIFNIPV | 31 | ISTGGTT | 32 | NVLVVSGIGSTLEV |

Variable region sequence (SEQ ID NO: 63):

```
QVQLVESGGGLVQPGGSLRLSCAASGSIFNIPVMGWYRQAPGKQRELVA
GISTGGTTNYGDSVKGRFTISRDNAKNTVYLQMNSLKPEDTAVYYCNVL
VVSGIGSTLEVWGQGTLVTVSS
```

The V (the position 5) and S (the last position) italicizing and bolding are humanization positions. The nucleotide sequence encoding the variable region sequence is as shown in SEQ ID NO: 64.

In order to investigate whether the affinity of NA3-S did not decrease after humanization, the method described in 1.3.1 was used to compare the binding capacities of NA3-S and NA3S-H1 on CLDN18.2-HEK293T cells. The results are as shown in FIG. 12: the humanized molecule NA3S-H1 and the parent antibody NA3-S had similar affinity and were both better than the control antibody IMAB362.

Example 13

Binding Specificity of Candidate Antibody NA3S-H1 at High Concentrations

The candidate antibody binding regions, ECD1s of CLDN18.2 and CLDN18.1 have only 8 amino acids different, and CLDN18.1 is expressed in lung epithelial cells. Therefore, if the antibody drug non-specifically binds to CLDN18.1, severe lung lesion or toxicity would be caused, thereby limiting the clinical application of the antibody drug. Therefore, in this example, different concentrations of the antibody (including the high concentration of 100 µg/mL) were used to incubate with CLDN18.1-HEK293 in vitro. The method was as described in 1.3.1. The antibody at different concentrations and target cells CLDN18.1-HEK293 were incubated at 4° C. for 1 h and then rinsed three times with the FACS buffer mentioned above. 0.5 µg (0.5 mg/ml) of PE-labelled goat anti-human IgG Fc antibody (Abcam, ab98596) was added and incubated at 4° C. for another 1 h. Subsequently, the cultures were rinsed with the FACS buffer for three times, and then 200 µL FACS buffer was added to the cells and the cells were resuspended, and finally, the cells were detected by a flow cytometry (Beckman, CytoFLEX AOO-1-1102). The binding strength and the positive rate of cell binding were recorded.

The results are as shown in FIG. 13a: in terms of binding strength, the binding signal of NA3S-H1 and the control antibody IMAB362 on CLDN18.1-HEK293 did not increase with the increase of concentrations and was almost the same as the binding strength of the isotype control. Furthermore, in terms of the positive rate of cell binding in FIG. 13b, even at the high concentration of 100 µg/mL, the positive rates for NA3S-H1 and IMAB362 were very weak (being between 0.04%-0.18%), wherein the positive rates for the three replicates of NA3S-H1 were 0.145%, 0.17% and 0.173%, the positive rates for the three replicates of IMAB362 were 0.042%, 0.128% and 0.041%, and the positive rates for the three replicates of the isotype control hIgG1 were 0.063%, 0.233% and 0.115%. By combining the results of FIGS. 13a and 13b, it could be seen that NA3S-H1 and the control antibody IMAB362 did not bind to CLDN18.1-HEK293 cells, and could both specifically bind to CLDN18.2 but did not bind to CLDN18.1.

Example 14

Complement Dependent Cytotoxicity (CDC) of
Candidate Antibody NA3S-H1

In this example, the complement dependent cytotoxicity of the humanized molecule NA3S-H1 and the control antibody IMAB362 were compared. The determination was performed with reference to the method in example 7. To put it simply, $5\times10^4$ CLDN18.2-KATOIII cells were taken and mixed with 5-fold diluted rabbit serum, and then 50 μL of the gradient-diluted candidate antibody NA3S-H1 or control antibody IMAB362 was added, respectively and incubated at 37° C. for 3 h. Then, 30 μL of the MTS reagent (Promega, G3580) was added and fully mixed to uniformity. The resulting cultures were placed in a constant temperature incubator at 37° C. with 5% $CO_2$ and cultured for 4 h, during which period the color of the medium was observed and finally the OD value at the wavelength of 492 nm was determined by using a microplate reader; 10% Triton X-100 plus target cells were used as the complete lysis control, the addition of target cells only were used as the blank negative control, and rabbit complement plus target cells were used as the background negative control, all of which were used to calculate the cell killing effect of the antibody.

The results are as shown in FIG. 14, compared to the control antibody IMAB362, NA3S-H1 had a stronger CDC cell killing effect, wherein the EC50 of NA3S-H1 was 10.41 nM, whereas the EC50 of IMAB362 was 149.4 nM.

Example 15

Humanized Antibody NA3S-H1 Mediated NK Cell
Cytotoxicity (ADCC)

In this example, the cytotoxicity mediated by the humanized antibody NA3S-H1 and the control antibody was compared by using the method as described in example 8. After the incubation of the gradient-diluted candidate antibody with target cells and human PBMC cells in a fixed ratio for 4 h, a method of using a LDH lactate dehydrogenase kit (Takara, MK401) was used to detect the release of lactate dehydrogenase in the cell supernatant at the wavelength of 492 nm, thereby determining the killing effect of the NK cells on the target cells mediated by the antibody.

FIGS. 15*a* and 15*b* show the cell killing effect of the NK cells on CLDN18.2-KATOIII or CLDN18.2-HEK293T mediated by the antibody. The results indicated that the ADCC effects mediated by the candidate antibody NA3S-H1 and the control antibody IMAB362 were close.

Those skilled in the art will further appreciate that the present invention may be embodied in other specific forms without departing from the spirit or central features thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A CLDN18.2 binding molecule, which is a VHH single domain antibody or a VHH-Fc antibody, wherein the VHH comprises a CDR1, a CDR2 and a CDR3 selected from the following groups, wherein:

(a) the CDR1 has the amino acid sequence as shown in SEQ ID NO: 30, the CDR2 has the amino acid sequence as shown in SEQ ID NO: 31, and the CDR3 has the amino acid sequence as shown in SEQ ID NO: 32;

(b) the CDR1 has the amino acid sequence as shown in SEQ ID NO: 1, the CDR2 has the amino acid sequence as shown in SEQ ID NO: 2, and the CDR3 has the amino acid sequence as shown in SEQ ID NO: 3;

(c) the CDR1 has the amino acid sequence as shown in SEQ ID NO: 1, the CDR2 has the amino acid sequence as shown in SEQ ID NO: 2, and the CDR3 has the amino acid sequence as shown in SEQ ID NO: 6;

(d) the CDR1 has the amino acid sequence as shown in SEQ ID NO: 1, the CDR2 has the amino acid sequence as shown in SEQ ID NO: 4, and the CDR3 has the amino acid sequence as shown in SEQ ID NO: 5;

(e) the CDR1 has the amino acid sequence as shown in SEQ ID NO: 30, the CDR2 has the amino acid sequence as shown in SEQ ID NO: 31, and the CDR3 has the amino acid sequence as shown in SEQ ID NO: 37;

(f) the CDR1 has the amino acid sequence as shown in SEQ ID NO: 33, the CDR2 has the amino acid sequence as shown in SEQ ID NO: 31, and the CDR3 has the amino acid sequence as shown in SEQ ID NO: 62;

(g) the CDR1 has the amino acid sequence as shown in SEQ ID NO: 33, the CDR2 has the amino acid sequence as shown in SEQ ID NO: 31, and the CDR3 has the amino acid sequence as shown in SEQ ID NO: 37;

(h) the CDR1 has the amino acid sequence as shown in SEQ ID NO: 34, the CDR2 has the amino acid sequence as shown in SEQ ID NO: 31, and the CDR3 has the amino acid sequence as shown in SEQ ID NO: 37;

(i) the CDR1 has the amino acid sequence as shown in SEQ ID NO: 35, the CDR2 has the amino acid sequence as shown in SEQ ID NO: 31, and the CDR3 has the amino acid sequence as shown in SEQ ID NO: 62;

(j) the CDR1 has the amino acid sequence as shown in SEQ ID NO: 36, the CDR2 has the amino acid sequence as shown in SEQ ID NO: 31, and the CDR3 has the amino acid sequence as shown in SEQ ID NO: 62;

(k) the CDR1 has the amino acid sequence as shown in SEQ ID NO: 38, the CDR2 has the amino acid sequence as shown in SEQ ID NO: 31, and the CDR3 has the amino acid sequence as shown in SEQ ID NO: 62;

(l) the CDR1 has the amino acid sequence as shown in SEQ ID NO: 39, the CDR2 has the amino acid sequence as shown in SEQ ID NO: 41, and the CDR3 has the amino acid sequence as shown in SEQ ID NO: 37; or (m) the CDR1 has the amino acid sequence as shown in SEQ ID NO: 40, the CDR2 has the amino acid sequence as shown in SEQ ID NO: 31, and the CDR3 has the amino acid sequence as shown in SEQ ID NO: 37.

2. The CLDN18.2 binding molecule of claim 1, wherein the VHH comprises any one selected from the following groups:

(a) the amino acid sequence of SEQ ID NO: 7, or an amino acid sequence at least 80%, 85%, 90%, or 95% identical to SEQ ID NO: 7; and (b) the amino acid sequence shown in SEQ ID NO: 47, or an amino acid sequence at least 80%, 85%, 90%, or 95% identical to SEQ ID NO: 47.

3. The CLDN18.2 binding molecule of claim 1, wherein the VHH comprises or consists of any one of the following sequences: SEQ ID NOs: 7, 8, 9, 10, 11, 12, 13, 14, 42, 43, 44, 45, 46, 47, 48, 49, 50, 51 and 63.

4. The CLDN18.2 binding molecule of claim 1, wherein the CLDN18.2 binding molecule is a chimeric antibody comprising a VHH from camelid and an Fc domain of human IgG1 or IgG4, or a humanized antibody comprising a VHH obtained by humanizing a VHH from camelid and an Fc domain of human IgG1 or IgG4.

5. An isolated nucleic acid molecule, comprising a nucleic acid sequence encoding the CLDN18.2 binding molecule as defined in claim 1.

6. An expression vector, comprising the isolated nucleic acid molecule of claim 5.

7. A host cell, comprising the expression vector of claim 6.

8. A pharmaceutical composition, comprising the CLDN18.2 binding molecule as defined in claim 1 and a pharmaceutically acceptable carrier.

9. A method for preparing the CLDN18.2 binding molecule as defined in claim 1, comprising the steps of:

(1) culturing a host cell comprising an expression vector (s) encoding the CLDN18.2 binding molecule; and (2) isolating the CLDN18.2 binding molecule from the culture supernatant.

10. A method for treating a cancer associated with CLDN18.2 in a subject, comprising: administering a therapeutically effective amount of the CLDN18.2 binding molecule as defined in claim 1 to the subject, wherein the cancer is selected from gastric cancer, pancreatic cancer and cancer of the esophagogastric junction.

11. The method of claim 10, wherein the cancer is gastric cancer.

12. A kit for treating or diagnosing a condition associated with CLDN18.2, comprising a container, wherein the container comprises the CLDN18.2 binding molecule as defined in claim 1.

* * * * *